United States Patent
Chilov et al.

(10) Patent No.: US 9,695,182 B2
(45) Date of Patent: Jul. 4, 2017

(54) CHEMICAL COMPOUNDS (DERIVATIVES) AND THEIR APPLICATION FOR THE TREATMENT OF ONCOLOGICAL DISEASES

(71) Applicants: LIMITED LIABILITY COMPANY "NATIONAL PHARMACEUTICAL TECHNOLOGIES", Moscow (RU); LIMITED LIABILITY COMPANY "PHARMENTERPRISES", Moscow (RU)

(72) Inventors: Germes Grigorievich Chilov, Domodedovo (RU); Oleg Valentinovich Stroganov, Kostroma (RU); Viktor Sergeevich Stroilov, Moscow (RU); Fedor Nikolaevich Novikov, Nizhny Novgorod (RU); Aleksey Alexandrovich Zeifman, Moscow (RU); Ilya Yurievich Titov, Moscow (RU)

(73) Assignees: LIMITED LIABILITY COMPANY "NATIONAL PHARMACEUTICAL TECHNOLOGIES", Moscow (RU); LIMITED LIABILITY COMPANY "PHARMENTERPRISES", Moscow (RU)

( * ) Notice: Subject to any disclaimer, the term of this patent is extended or adjusted under 35 U.S.C. 154(b) by 0 days.

(21) Appl. No.: 14/912,473

(22) PCT Filed: Jun. 30, 2014

(86) PCT No.: PCT/RU2014/000478
§ 371 (c)(1),
(2) Date: Feb. 17, 2016

(87) PCT Pub. No.: WO2015/047133
PCT Pub. Date: Apr. 2, 2015

(65) Prior Publication Data
US 2016/0200729 A1 Jul. 14, 2016

(30) Foreign Application Priority Data
Sep. 26, 2013 (RU) .................. 2013143520

(51) Int. Cl.
*C07D 487/04* (2006.01)
*A61K 31/5025* (2006.01)

(52) U.S. Cl.
CPC .................. *C07D 487/04* (2013.01)

(58) Field of Classification Search
None
See application file for complete search history.

(56) References Cited

U.S. PATENT DOCUMENTS 2,942,001 A  6/1960  Druey et al.

FOREIGN PATENT DOCUMENTS

| RU | 2 374 248 C2 | 11/2009 |
|---|---|---|
| WO | WO 01/51492 A1 | 7/2001 |
| WO | WO 2004/076412 A2 | 9/2004 |
| WO | WO 2005/016894 A1 | 2/2005 |
| WO | WO 2005/009389 A2 | 3/2005 |
| WO | WO 2005/080393 A1 | 9/2005 |
| WO | WO 2005/097765 A1 | 10/2005 |
| WO | WO 2007/066187 A2 | 6/2007 |
| WO | WO 2007/130468 A2 | 11/2007 |
| WO | WO 2008/100463 A1 | 8/2008 |
| WO | WO 2012/048259 A2 | 4/2012 |

OTHER PUBLICATIONS

Bernas, T., et al; "Reduction of a tetrazolium salt, CTC, by intact HepG2 human hepatoma cells: subcellular localisation of reducing systems"; *Biochimica et Biophysica Acta*, 1451, pp. 73-81 (1999).
Falini, B., et al; "Lymphomas Expressing ALK Fusion Protein(s) Other Than NPM-ALK"; *Blood*, vol. 94, No. 10, pp. 3509-3515 (1999).
Karaman, M.W., et al; "A quantitative analysis of kinase inhibitor selectivity"; *Nature Biotechnology*, vol. 26, No. 1, pp. 127-132 (2008).
Bhagwat, S.S.; "Kinase inhibitors for the treatment of inflammatory and autoimmune disorders"; *Purinergic Signalling*, vol. 5, pp. 107-115 (2009).
Duyster, J., et al; "Translocations involving anaplastic lymphoma kinase (ALK)"; *Oncogene*; vol. 20, pp. 5623-5637 (2001).
Pao, W., et al; "New driver mutations in non-small-cell lung cancer"; *Lancet Oncol.*, vol. 12, pp. 175-180 (2011).
Shaw, A.T., et al; "Targeting Anaplastic Lymphoma Kinase in Lung Cancer"; *Clinical Cancer Research*; vol. 17, pp. 2081-2086 (2011), Published OnlineFirst Feb. 2, 2011.

(Continued)

*Primary Examiner* — Emily Bernhardt
(74) *Attorney, Agent, or Firm* — Nixon & Vanderhye P.C.

(57) ABSTRACT

Compounds of formula I, in which $L^A$, $L^B$, $L^C$, ring A, ring B, $R^A$, $R^B$, $R^C$, $R^D$, $R^E$ and $R^F$ are defined in the description, and which are protein kinases inhibitors. The invention also relates to pharmaceutical compositions containing said compounds and also to the use of those compounds for treatment and/or prevention of diseases related with aberrant protein kinase activity.

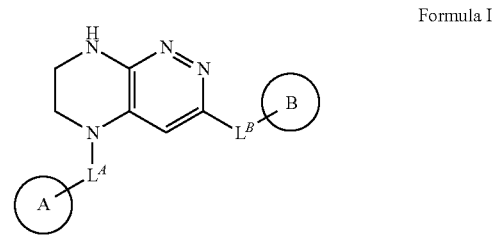

Formula I

6 Claims, No Drawings

(56) References Cited

OTHER PUBLICATIONS

Kutok, J.L., et al; "Molecular Biology of Anaplastic Lymphoma Kinase-Positive Anaplastic Large-Cell Lymphoma"; *Journal of Clinical Oncology*, vol. 20, No. 17, pp. 3691-3702 (2001).
Morris, S.W., et al; Review, "ALK+ CD30+ Lymphomas: A Distinct Molecular Genetic Subtype of Non-Hodgkin's Lymphoma"; *British Journal of Haematology*, vol. 113, pp. 275-295 (2001).
Bai, Ren-Yuan, et al; "Nucleophosmin-anaplastic lymphoma kinase associated with anaplastic large-cell lymphoma activates the phosphatidylinositol 3-kinase/Akt antiapoptotic signaling pathway"; *Blood*, vol. 96, No. 13, pp. 4319-4327 (2000).
Christensen, J.G., et al; "Cytoreductive antitumor activity of PF-2341066, a novel inhibitor o fanaplastic lymphoma kinase and c-Met, in experimental models of anaplastic large-cell lymphoma"; *Molecular Cancer Therapeutics*; vol. 6, pp. 3314-3322 (2007).
Di Maio, M., et al; "Meta-Analysis of Single-Agent Chemotherapy Compared With Combination Chemotherapy as Second-Line Treatment of Advanced Non-Small-Cell Lung Cancer"; *Journal of Clinical Oncology*; vol. 27, No. 11, pp. 1836-1843 (2009).
Kwak, E.L., et al; "Anaplastic Lymphoma Kinase Inhibition in Non-Small-Cell Lung Cancer"; *The New England Journal of Medicine*; vol. 363, No. 18, pp. 1693-1703 (2010).
Choi, Y.L., et al; "EML4-ALK Mutations in Lung Cancer That Confer Resistance to ALK Inhibitors"; *The New England Journal of Medicine*; vol. 363, pp. 1734-1739 (2010).
Sasaki, T., et al; "The Neuroblastoma-Associated F1174L ALK Mutation Causes Resistance to an ALK Kinase Inhibitor in ALK-Translocated Cancers"; *Cancer Research*, vol. 70, pp. 10038-10043 (2010).
Doebele, R.C., et al; "Mechanisms of Resistance to Crizotinib in Patients with ALK Gene Rearranged Non—Small Cell Lung Cancer"; *Clinical Cancer Research*; vol. 18, pp. 1472-1482; Published OnlineFirst Jan. 10, 2012.
Shaw, A.T., et al; "Effect of crizotinib on overall survival in patients with advanced non-small-cell lung cancer harbouring ALK gene rearrangement: a retrospective analysis"; *Lancet Oncology*, vol. 12, pp. 1004-1012 (2011).
Costa, D.B., et al; "CSF Concentration of the Anaplastic Lymphoma Kinase Inhibitor Crizotinib"; *Journal of Clinical Oncology*; vol. 29, No. 15, pp. e443-e445 (May 20, 2011).
Weisberg, E. et al; "Inhibition of mutant FLT3 receptors in leukemia cells by the small molecule tyrosine kinase inhibitor PKC412"; *Cancer Cell*, vol. 1, pp. 433-443 (2002).
Berge, S.M., et al; "Pharmaceutical Salts"; *Journal of Pharmaceutical Sciences*; vol. 66, No. 1, pp. 1-19 (1977).
Katritzky, A.R., et al; "Handbook of Heterocyclic Chemistry"; Second Edition 2000, pp. 1-741 (Book-1).
Ausubel, F.M., et al; "Current Protocols in Molecular Biology"; John Wiley and Sons, Dec. 4, 2013, pp. 1-2000 (Book 2a).
Ausubel, F.M., et al; "Current Protocols in Molecular Biology"; John Wiley and Sons, Dec. 4, 2013, pp. 2001-4000 (Book 2b).
Ausubel, F.M., et al; "Current Protocols in Molecular Biology"; John Wiley and Sons, Dec. 4, 2013, pp. 4001-4755 (Book 2c).
Zhang, I., et al; "Targeting brain metastases in ALK-rearranged non-small-cell lung cancer"; *The Lancet Oncology*; vol. 16, No. 13, pp. e510-e521 (2015).
Roskoski, Jr. R., et al; "Anaplastic lymphoma kinase (ALK): Structure, oncogenic activation, and pharmacological inhibition"; *Pharmacological Research*, vol. 68, pp. 68-94 (2013).
Mologni, L.; "Inhibitors of the anaplastic lymphoma kinase"; *Expert Opinion on Investigational Drugs*; vol. 21, No. 7, pp. 985-994 (2012).
Milkiewicz, Karen L., et al; "Synthesis and structure-activity relationships of 1,2,3,4-tetrahydropyrido[2,3-b]pyrazines as potent and selective inhibitors of the anaplastic lymphoma kinase"; *Bioorganic & Medicinal Chemistry*; vol. 18, pp. 4351-4362 (2010).
Predvoditeleva, G.S., et al; "Pyridazinoquinoxalines. III. Synthesis of dihydropyridazino[3,4b]quinoxalines Containing Chlorine in the Pyridazine Ring"; *Khimiko-Farmatsevticheskii Zhurnal*, vol. 7(5), pp. 13-16 (1973) with English Translation.

CHEMICAL COMPOUNDS (DERIVATIVES) AND THEIR APPLICATION FOR THE TREATMENT OF ONCOLOGICAL DISEASES

This application is the U.S. national phase of International Application No. PCT/RU2014/000478 filed Jun. 30, 2014 which designated the U.S. and claims priority to Russian Patent Application No. 2013143520 filed Sep. 26, 2013, the entire contents of each of which are hereby incorporated by reference.

FIELD OF THE INVENTION

This invention refers to organic chemistry, pharmacology and medicine and relates to the therapy of oncological, chronic inflammatory and other diseases with new families of chemical compounds having increased efficacy in the inhibition of therapeutically significant kinases, in particular, ALK-kinase and its mutants, as well as the increased selectivity and bioavailability.

BACKGROUND OF THE INVENTION

The protein kinases represent an important family of proteins involved in the regulation of key cellular processes, violation of activity of which can lead to oncological, chronic inflammatory diseases, diseases of the central nervous system, etc. The list of kinases, the therapeutic significance of which to date has preclinical or clinical validation, includes: ABL1, ALK, AKT, AKT2, AURKA, BRAF, BCR-ABL, BLK, BRK, C-KIT, C-MET, C-SRC, CAMK2B, CDK1, CDK2, CDK3, CDK4, CDK5, CDK6, CDK7, CDK8, CDK9, CRAF1, CHEK1, CHEK2, CLK1, CLK3, CSF1R, CSK, CSNK1G2, CSNK1G3, CSNK2A1, DAPK1, DAPK2, DAPK3, EGFR, EPHA2, EPHA3, EPHA5, ERBB2, ERBB3, ERBB4, ERK, ERK2, ERK3, FES, FGFR1, FGFR2, FGFR3, FGFR4, FGFR5, FGR, FLT-1, FYN, GSK3B, HCK, IGF1R, INSR, ITK, JAK1, JAK2, JAK3, JNK1, JNK2, JNK3, KIT, LCK, LOK, MAP3K5, MAPKAPK2, MARK1, MEK1, MEK2, MET, MKNK2, MST1, NEK2, P38α, P38δ, P38γ, PAK1, PAK4, PAK6, PAK7, PDPK1, PDGFR, PIK3CG, PIM1, PIM2, PKC, PLK1, PLK4, PRKCQ, PRKR, PTK2, PTK2B, RET, ROCK1, ROS1, RPS6KA1, SLK, SRC, SRPK1, STK16, SYK, TAK1, TGFBR1, TIE, TIE2, TNK2, TRK, VEGFR2, WEE1, ZAP70 (Karaman, M. W. et. al., *Nat Biotechnol,* 2008, 26, 127-32; Bhagwat, S. S., *Purinergic Signal,* 2009, 5, 107-15). This list is constantly growing with the advent of new experimental data.

The promising approach for the treatment of diseases associated with the aberrant activity of protein kinases includes the use of low-molecular chemical compounds for the inhibition of their activity. Examples of such inhibitors approved for use in clinical practice, are: Imatinib, Nilotinib, Dasatinib, Sunitinib, Sorafenib, Lapatinib, Gefitinib, Erlotinib, Crizotinib. A large number of drug candidate kinase inhibitors are currently at the stage of clinical trials and preclinical development.

Anaplastic Lymphoma Kinase, ALK—is a transmembrane receptor tyrosine kinase that belongs to the family of insulin receptors. ALK kinase is most strongly expressed in the brain of the newborn, suggesting a possible role of ALK in brain development (Duyster, J. et. al., *Oncogene,* 2001, 20, 5623-37).

Aberrant activity of Anaplastic Lymphoma Kinase is a cause of many oncological diseases. For example, the cause of 3-6% of non-small cell lung cancer (NSCLC) is chromosomal translocation activating the formation of a chimeric protein consisting of the EML4 protein and ALK intracellular domain (Pao, W. et. al., *Lancet Oncol,* 2011, 12, 175-80; Shaw, A. T. et. al., *Clin Cancer Res,* 2011, 17, 2081-6). Other chromosomal translocation leads to the formation of the NPM-ALK chimeric protein, and causes about 60% of the cases of anaplastic large cell lymphoma (ALCL) (Kutok, J. L. et. al., *J Clin Oncol,* 2002, 20, 3691-702). Constitutive tyrosine kinase activity of the chimeric proteins, EML4-ALK in the case of NSCLC, or NPM-ALK in the case of ALCL, causes activation of downstream signaling pathways responsible for the cell division and protection from apoptosis and eventually leading to cell oncotransformation (Falini, B. et. al., *Blood,* 1999, 94, 3509-15; Morris, S. W. et. al., *Br J Haematol,* 2001, 113, 275-95; Bai, R. Y. et. al., *Blood,* 2000, 96, 4319-27). ALK-positive carcinomata are oncogene-dependent: blocking the enzyme activity using ALK inhibitors leads to cell cycle arrest and apoptosis of cancer cells (Christensen, J. G. et. al., *Mol Cancer Ther,* 2007, 6, 3314-22).

The ALK inhibition is a promising strategy to combat ALK-positive forms of non-small cell lung cancer, anaplastic large cell lymphoma, and other oncological diseases, the cause of which lies in a constitutive activity of ALK. Clinical trials of ALK inhibitor Crizotinib in patients with advanced NSCLC showed that the life expectancy of patients increased by 9 months and more (Di Maio, M. et. al., *J Clin Oncol,* 2009, 27, 1836-43) even to 2 years (Kwak, E. L. et. al., *N Engl J Med,* 2010, 363, 1693-703). To date there are numerous known ALK inhibitors, including indazole isoquinolines (WO 2005/009389), thiazole and oxazole amides (WO 2005/097765), pyrrolopyrimidines (WO 2005/080393), pyrimidinediamines (WO 2005/016894), aminopyridines and aminopyrazines (WO 2004/076412; WO 2007/066187), piridopyrazines (WO 2007/130468).

The use of low-molecular inhibitors of ALK in therapeutic practice has revealed a number of serious problems with their efficiency. Firstly, the problems are associated with low activity of inhibitors toward ALK mutated forms, which may eventually appear in patients. For example, it is known that the kinase domain of the EML4-ALK gene product, the target of non-small cell lung cancer, is susceptible to occurrence of mutations that determine resistance to Crizotinib (mutations L1196M, C1156Y, G1269A and F1174L) (Choi, Y. L. et. al., *N Engl J Med,* 2010, 363, 1734-9; Sasaki, T. et. al., *Cancer Res,* 2010, 70, 10038-43). The frequency of such mutations reaches 30% (Doebele, R. C. et. al., *Clin Cancer Res,* 2012). Secondly, increase in life expectancy of patients promotes the likelihood of brain metastases formation: on an average metastases occur in 50% of patients for 2 years of treatment (Shaw, A. T. et. al., *Lancet Oncol,* 2011, 12, 1004-12). Practically Crizotinib does not penetrate through the blood-brain barrier and therefore does not affect the brain metastases despite the fact that the primary tumor in the lung of the same patient may continue to decline (Costa, D. B. et. al., *J Clin Oncol,* 2011, 29, e443-5). Thus, development of new compounds capable of inhibiting the kinase mutant forms, and of penetrating through the blood-brain barrier is practically very important task.

This invention relates to new families of chemical compounds having increased efficacy in the inhibition of protein kinases and their mutants, and promising for use in the treatment of oncological, chronic inflammatory and other diseases.

SUMMARY OF THE INVENTION

The task (technical result) of the present invention is to provide new chemical compounds having increased efficacy in the inhibition of protein kinases, in particular ALK-kinase, and their mutant forms, as well as increased selectivity and bioavailability, and promising for the use in treatment of oncological, chronic inflammatory and other diseases, in particular tumors of the central nervous system—due to the ability of new compounds to penetrate through the blood-brain barrier.

1. OVERVIEW OF INVENTION COMPOUNDS 1.1. The present invention relates to compounds of general formula I,

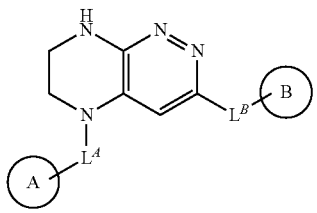

Formula I their tautomers, isomers or enantiomers or their pharmaceutically acceptable salts, solvates or hydrates, where:

$L^A$ represents $CH_2$ or $CH(CH_3)$;

$L^B$ represents covalent chemical bond, $OC_{0-3}$-alkyl, $SC_{0-3}$-alkyl, $NHC(O)C_{0-3}$-alkyl, $C(O)NHC_{0-3}$-alkyl, $C(O)C_{0-3}$-alkyl, $NHC_{0-3}$-alkyl, $CH_2O$, $CH_2S$, $CH_2C(O)NH$ or $CH_2NH$;

cycle A represents phenyl or a 5-6 membered heteroaryl containing 0-3 N atoms and 0-1 O or S atoms, and optionally substituted with by 1-4 groups of $R^A$;

$R^A$ is selected independently and represents halogen, partially or completely halogenated $C_{1-5}$-alkyl, $C_{2-5}$-alkenyl, $C_{2-5}$-alkynyl, $(CH_2)_mO(CH_2)_nH$, $(CH_2)_mNH(CH_2)_nH$, $(CH_2)_mC(O)O(CH_2)_nH$, $(CH_2)_mOC(O)(CH_2)_nH$, $(CH_2)_mC(O)NH(CH_2)_nH$, $(CH_2)_mNHC(O)(CH_2)_nH$, CN, $P(O)(R^F)_2$, $P(O)_2(R^F)$, $P(O)_2OH$, $SR^E$, $S(O)R^E$, $S(O)_2R^E$ or $S(O)_2OH$;

cycle B represents phenyl, $C_{3-8}$ cycloalkyl, 4-8-membered saturated or partially saturated heterocycle containing 0-3 N atoms, and 0-1 O or S atoms; or a 5-6 membered heteroaryl ring containing 0-3 N atoms, and 0-1 O or S atoms; cycle B optionally comprises 1-5 substituents of $R^B$;

$R^B$ is selected independently and represents halogen, $L^C$-$R^C$, $L^C$-H, partially or completely halogenated $C_{1-5}$-alkyl, $C_{2-5}$-alkenyl, $C_{2-5}$-alkynyl or CN; alternatively, two adjacent groups of $R^B$, together with the atoms to which they are attached, may form a 5-, 6- or 7-membered saturated, partially saturated or unsaturated ring, containing 0-3 heteroatoms selected from N, O, S, S(O), $S(O)_2$ and $R^C$ or $R^D$ optionally substituted with 1-4 substituents;

$L^C$ represents covalent chemical bond, $C_{1-3}$-alkyl, $(CH_2)_mO(CH_2)_n$, $(CH_2)_mNH(CH_2)_n$, $(CH_2)_mC(O)(CH_2)_n$, $(CH_2)_mC(O)O(CH_2)_n$, $(CH_2)_mOC(O)(CH_2)_n$, $(CH_2)_mC(O)NH(CH_2)_n$ or $(CH_2)_mNHC(O)(CH_2)_n$;

$R^C$ is selected independently and represents phenyl, $C_{1-6}$-alkyl, $C_{3-7}$ cycloalkyl or 3-7 membered heteroalicyclyl containing 0-3 N atoms, 0-2 O atoms and 0-2 S atoms; $R^C$ optionally contains 1-5 substituents of $R^D$ or $CH_2R^D$;

$R^D$ is selected independently and represents halogen, $(CH_2)_mCH_3$, $(CH_2)_mO(CH_2)_nH$, $(CH_2)_mC(O)NH(CH_2)_nH$, $(CH_2)_mC(O)(CH_2)_nH$, $(CH_2)_mNH_2$, $NHR^F$, $N(R^F)_2$ or 3-7 membered heteroalicyclyl containing 0-3 N atoms, 0-2 O atoms, 0-2 S atoms, and $R^F$ optionally containing 1-3 substituents;

$R^E$ is selected independently and represents $C_{1-3}$-alkyl, $NHC_{1-3}$-alkyl or $N(C_{1-3}$-alkyl$)_2$;

$R^F$ is selected independently and represents $C_{1-3}$-alkyl;

m and n are selected independently from 0, 1, 2, 3;

2. FEATURED CLASSES OF THE INVENTION IMPLEMENTATION

A separate subclass of compounds of interest includes compounds of formula I, where:

$L^A$ represents $CH_2$ or $CH(CH_3)$;

$L^B$ represents covalent chemical bond, $OC_{0-3}$-alkyl, $SC_{0-3}$-alkyl, $NHC(O)C_{0-3}$-alkyl, $C(O)NHC_{0-3}$-alkyl, $C(O)C_{0-3}$-alkyl, $NHC_{0-3}$-alkyl, $CH_2O$, $CH_2S$, $CH_2C(O)NH$ or $CH_2NH$;

cycle A represents phenyl, optionally substituted with by 1-3 groups of $R^A$;

$R^A$ represents halogen, partially or completely halogenated $C_{1-3}$-alkyl, $S(O)C_{1-3}$-alkyl, $S(O)_2C_{1-3}$-alkyl, $S(O)NHC_{1-3}$-alkyl, $S(O)_2NHC_{1-3}$-alkyl, $S(O)N(C_{1-3}$-alkyl$)_2$, $S(O)_2N(C_{1-3}$-alkyl$)_2$ or $P(O)(C_{1-3}$-alkyl$)_2$;

cycle B represents phenyl, $C_{3-7}$ cycloalkyl, 4-6-membered saturated or partially saturated heterocycle containing 0-3 N atoms, and 0-1 O or S atoms; or a 5-6 membered heteroaryl ring containing 0-3 N atoms, and 0-1 O or S atoms; cycle B optionally comprises 1-5 substituents of $R^B$;

$R^B$ is selected independently and represents $L^C$-$R^C$, $L^C$-H, halogen or partially or completely halogenated $C_{1-3}$-alkyl; alternatively, two adjacent groups of $R^B$, together with the atoms to which they are attached, may form a 5-, 6- or 7-membered saturated, partially saturated or unsaturated ring, containing 0-3 heteroatoms selected from N, O, S, and $R^C$ or $R^D$ optionally substituted with 1-4 substituents;

$L^C$ represents covalent chemical bond, $C_{1-3}$-alkyl, $(CH_2)_mC(O)(CH_2)_n$, $(CH_2)_mC(O)NH(CH_2)_n$ or $(CH_2)_mO(CH_2)_n$;

$R^C$ is selected independently and represents phenyl, $C_{1-6}$-alkyl, or 4-6 membered heteroalicyclyl containing 0-2 N atoms, 0-1 O atom; $R^C$ optionally contains 1-5 substituents of $R^D$ or $CH_2R^D$;

$R^D$ is selected independently and represents $(CH_2)_mCH_3$, $(CH_2)_mO(CH_2)_nH$, $(CH_2)_mC(O)NH(CH_2)_nH$, $(CH_2)_mC(O)(CH_2)_nH$, $(CH_2)_mNH_2$, $N(R^F)_2$ or 4-6 membered heteroalicyclyl containing 0-2 of N atom, 0-1 of O atom; $R^D$ optionally contains 1-3 substituents of $C_{1-3}$-alkyl;

m and n are independently selected from 0, 1, 2, 3.

Another subclass of compounds of interest includes compounds of formula I, where:

$L^A$ represents $CH_2$ or $CH(CH_3)$;

$L^B$ represents covalent chemical bond, $C(O)NH$ or NH;

cycle A represents phenyl, optionally substituted with 1-3 groups of $R^A$;

$R^A$ represents Cl, F, $CF_3$ or $OCH_3$;

cycle B represents phenyl; 5-membered heteroaryl ring containing 1-3 of N atom; 5-membered heteroaryl ring containing 1-2 N atoms and 1 O atom and 6-membered heteroaryl ring containing 1-3 N atoms; cycle B optionally comprises 1-3 substituents of $R^B$;

$R^B$ is selected independently and represents $L^C$-$R^C$ or $L^C$-H;

$L^C$ represents covalent chemical bond, $CH_2$, C(O), C(O)NH, $CH_2C(O)NH$, $C(O)NHCH_2$, $C(O)NH(CH_2)_2$ or $OCH_2$;

$R^C$ is selected independently and represents phenyl, $C_{1-3}$-alkyl or 4-6 membered heteroalicyclyl containing 0-2 N atoms and 0-1 O atom; $R^C$ optionally contains 1-3 substituents of $R^D$ or $CH_2R^D$;

$R^D$ is selected independently and represents $CH_3$, $OCH_3$, OH, $CH_2C(O)NH_2$, $C(O)CH_3$, $N(R^F)_2$ or 4-6 membered heteroalicyclyl containing 0-2 N atoms, 0-1 O atom, and $R^D$ optionally contains 1-3 substituents of $R^F$;

$R^F$ represents $CH_3$.

Next subclass of compounds of interest includes compounds of formula I, where $L^B$ represents a covalent chemical bond, NH or C(O)NH.

Additionally, a subclass of compounds of interest also includes compounds of formula I, where cycle A is phenyl ring.

2.1. A separate subclass of compounds of interest includes compounds of formula I, where cycle B represents phenyl.

Another subclass of compounds of interest includes compounds of formula I, where cycle B represents $C_{3-7}$ cycloalkyl.

Another subclass of compounds of interest includes compounds of formula I, where cycle B represents 4-6-membered saturated or partially saturated heterocycle containing 0-3 N atoms, and 0-1 O or S atom.

Another subclass of compounds of interest includes compounds of formula I, where cycle B represents 5-6 membered heteroaryl ring containing 0-3 N atoms, and 0-1 O or S atoms.

2.2. A separate class of compounds of interest includes compounds of formula I, where $L^B$ linker is $NHC_{0-3}$-alkyl or $CH_2NH$. The following compounds are illustrative examples of this class:

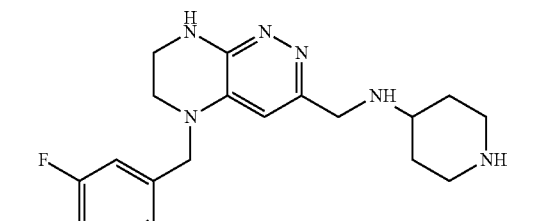

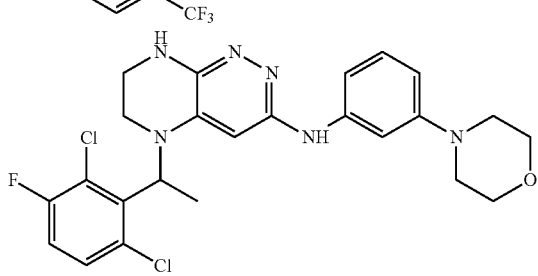

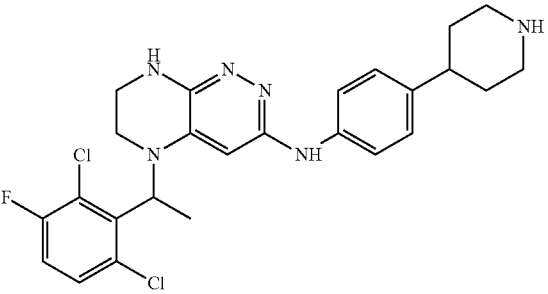

2.3. Another class of compounds of interest includes compounds of formula I, where $L^B$ linker is $C(O)C_{0-3}$-alkyl. The following compounds are illustrative examples of this class:

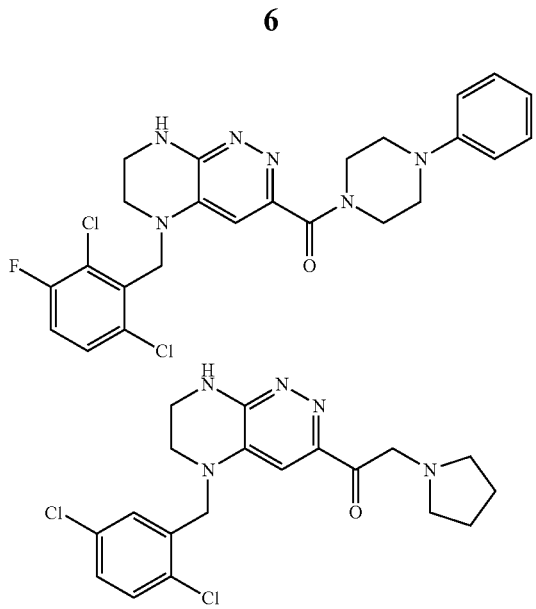

2.4. Another class of compounds of interest includes compounds of formula I, where $L^B$ linker is $C(O)NHC_{0-3}$-alkyl. The following compounds are illustrative examples of this class:

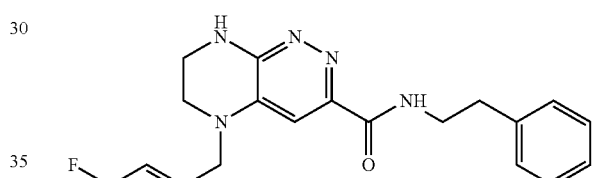

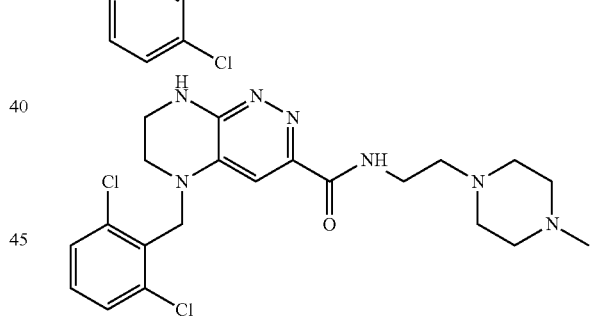

2.5. One more class of compounds of interest includes compounds of formula I, where $L^B$ linker represents $OC_{0-3}$-alkyl, $SC_{0-3}$-alkyl, $CH_2O$ or $CH_2S$. The following compounds are illustrative examples of this class:

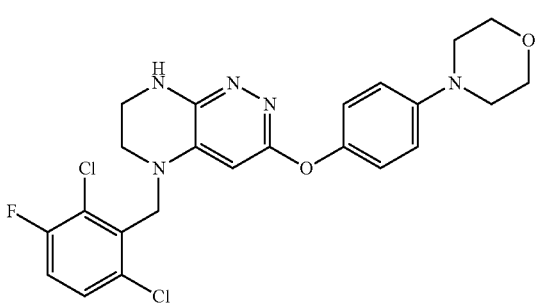

-continued

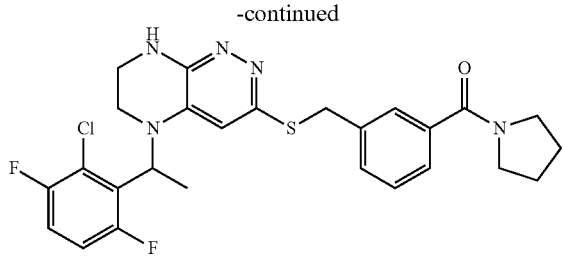

2.6. One more class of compounds of interest includes compounds of formula I, where $L^B$ linker represents NHC(O)$C_{0-3}$-alkyl or $CH_2C(O)NH$. The following compounds are illustrative examples of this class:

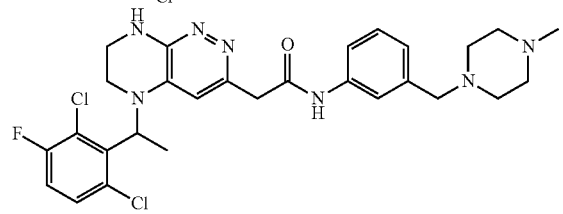

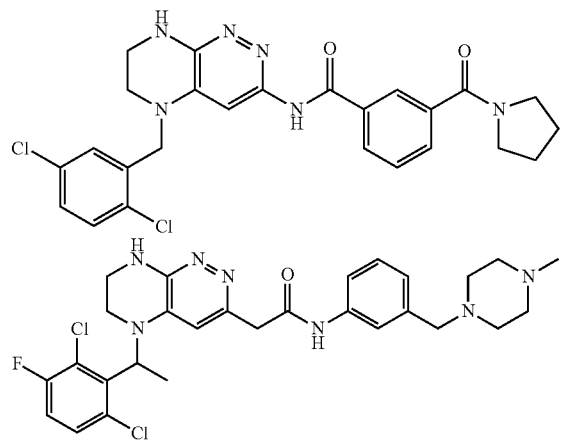

2.7. Another preferred embodiment of the invention includes compounds of formula I, where $L^B$ linker represents covalent chemical bond. This subclass of compounds is illustrated by the formula IA:

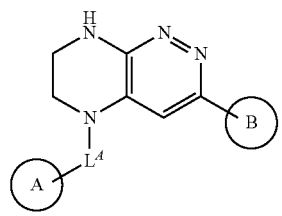

Formula IA 2.8. One of the preferred embodiment of the invention includes compounds of formulas I, IA and other classes and subclasses of the invention, where cycle B represents phenyl, optionally substituted with 1-5 substituents of RB. Illustrative examples of phenyl group with RB substituents are presented below:

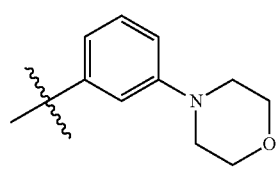

-continued

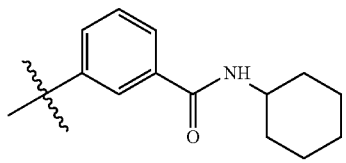
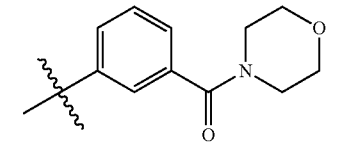
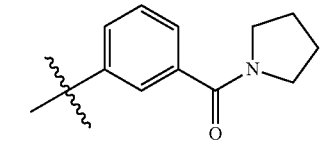
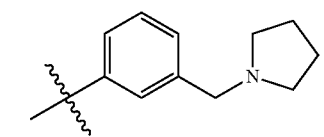
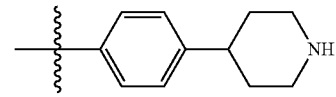
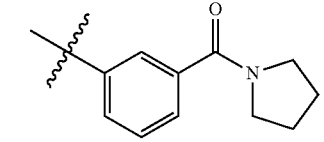
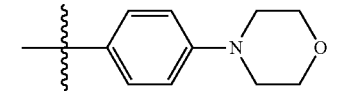
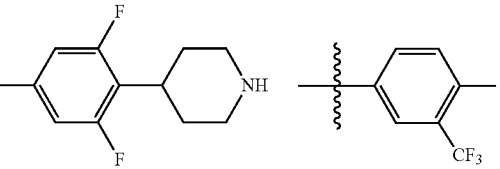
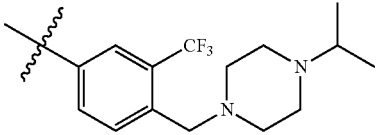
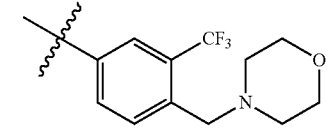
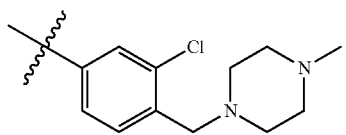
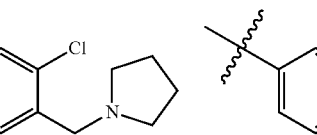

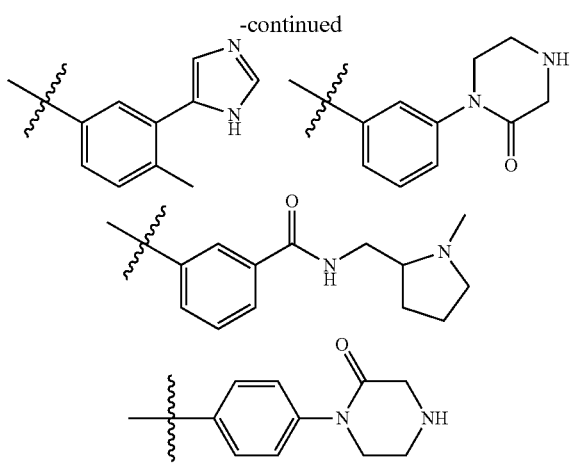

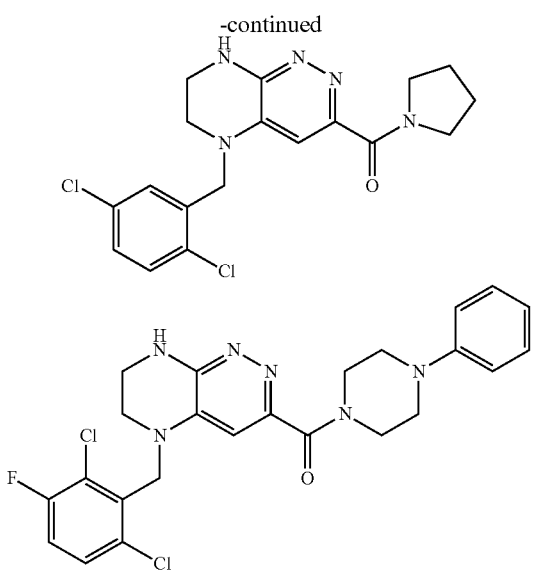

2.9. Another embodiment of the includes compounds of formulas I, IA and other classes and subclasses of the invention, where cycle B represents $C_{3-7}$ cycloalkyl, optionally substituted with 1-5 substituents of $R^B$. The following compounds are non-limiting examples of this embodiment:

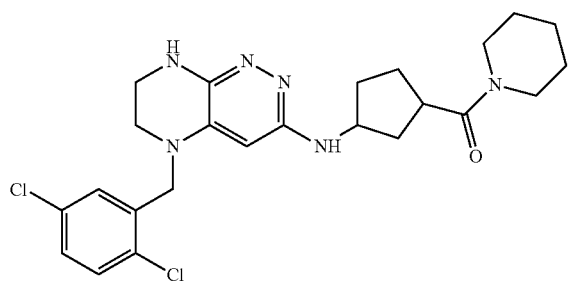

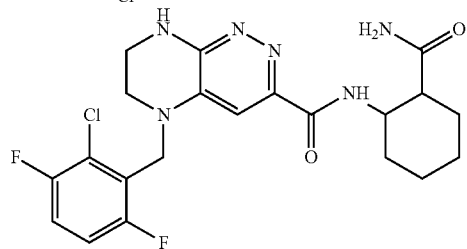

2.10. Another embodiment of the invention includes compounds of formula I and IA, where cycle B represents 4-6-membered saturated or partially saturated heterocycle containing C atoms, 0-3 N atoms, and 0-1 O or S atoms; optionally substituted with 1-5 substituents of $R^B$. The following compounds are non-limiting examples of this class:

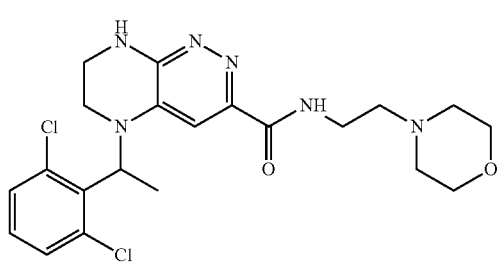

2.11. A separate preferred embodiment of the invention includes compounds of formulas I, IA and other classes and subclasses of the invention, where cycle B represents 5- or 6-membered heteroaryl rind, containing 0-3 N atoms, and 0-1 O or S atoms; optionally substituted with 1-4 substituents of $R^B$.

2.12. An embodiment of particular interest includes compounds of formulas I, IA and other subclasses of the invention, where cycle B represents 5-membered heteroaryl ring, containing C atoms and 1-3 N atoms, and optionally substituted with 1-3 substituents of $R^B$. The compounds with the following B rings are non-limiting examples of this class:

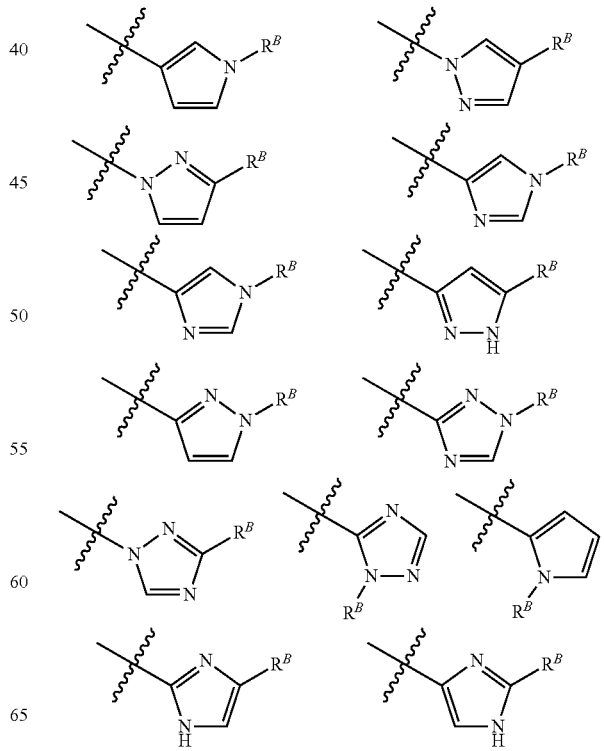

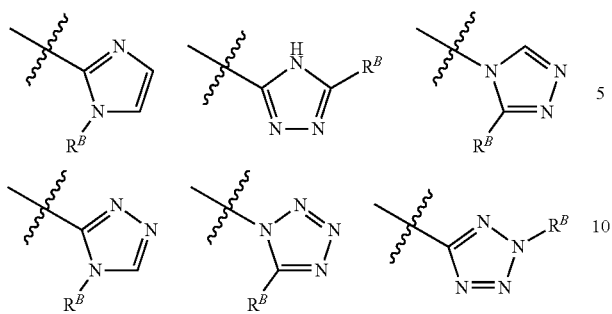

The non-limiting examples of the above-indicated variants of cycle B, substituted with $R^B$, appear as follows:

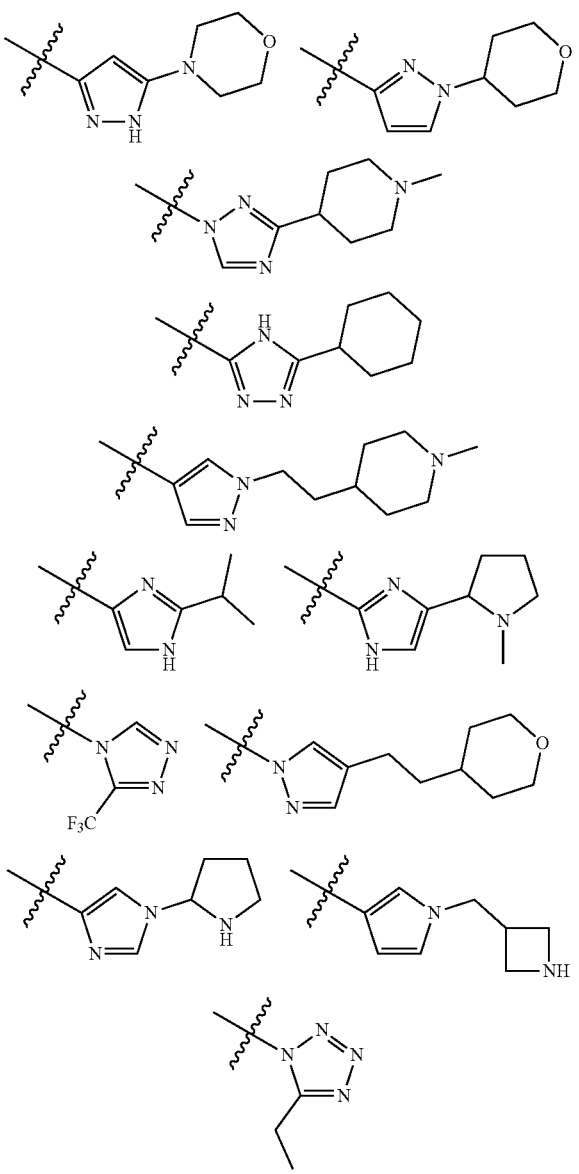

The non-limiting examples of this class of compounds have the following formulas:

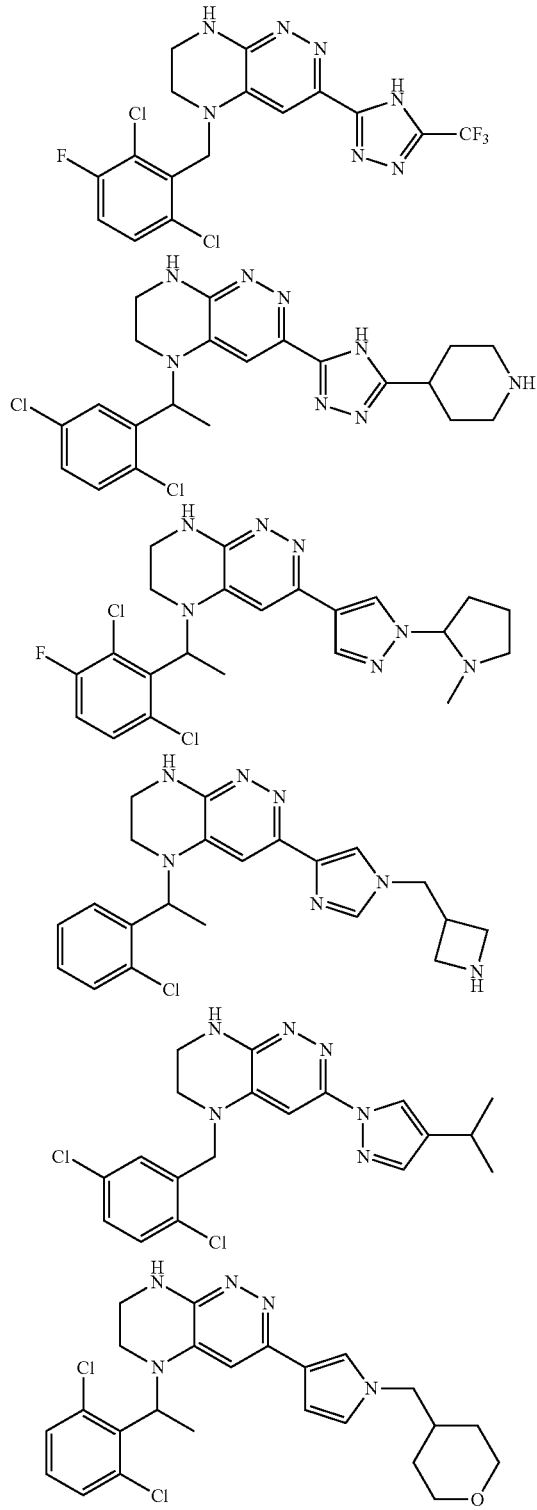

2.13. Another subclass of the invention of particular interest includes compounds of formulas I, IA and other classes and subclasses of the invention, where cycle B represents 5-membered heteroaryl ring, containing C atoms, 1-2 N atoms, and 1 O atom, optionally substituted with 1-3 substituents of $R^B$. The compounds with the following B rings are non-limiting examples of this class:

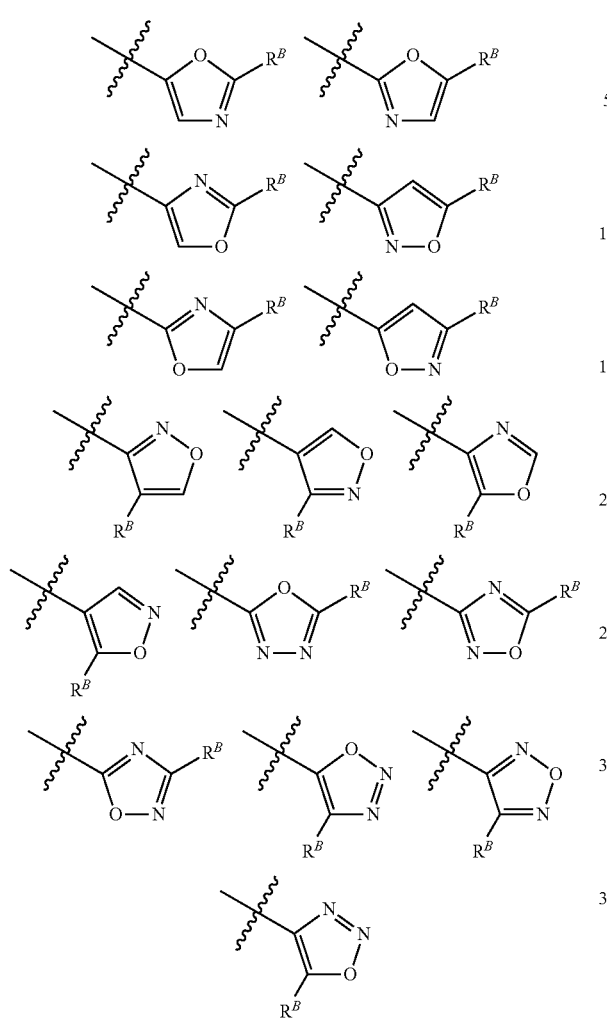
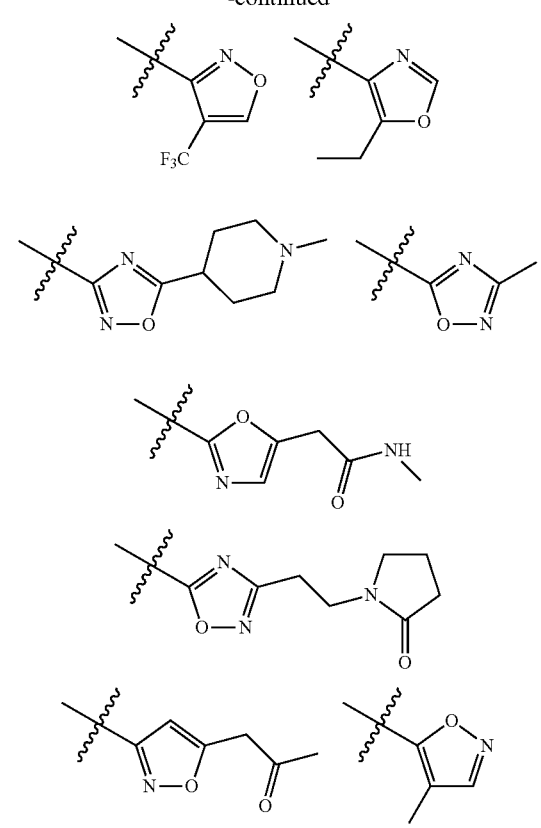
The non-limiting illustrative examples of the above-indicated variants of cycle B, substituted with RB, appear as follows:
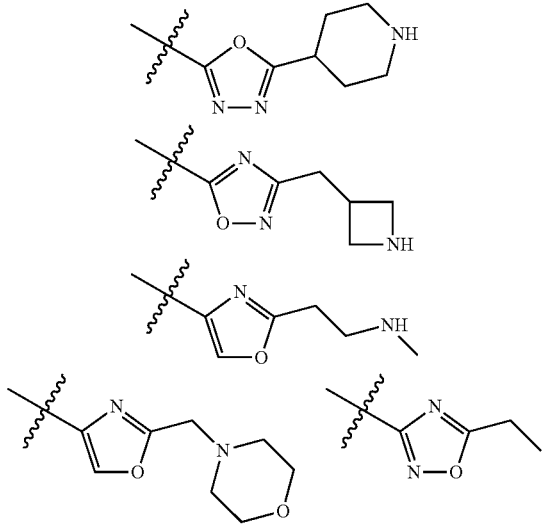
The non-limiting illustrative examples of this class of compounds have the following formulas:
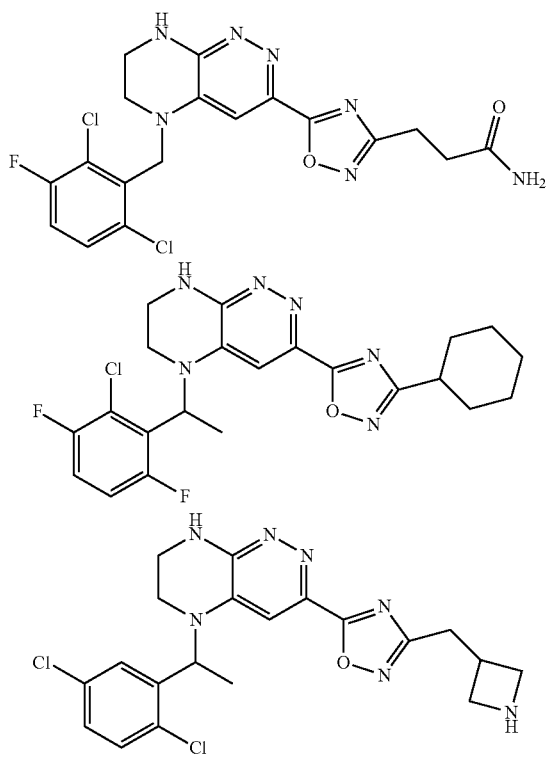

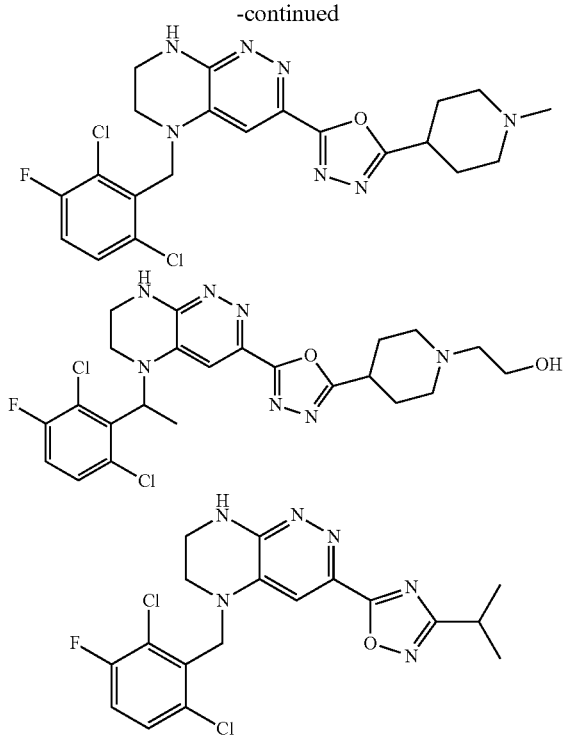

2.14. A separate variant of the previous embodiment of particular interest includes compounds of formulas I, IA and other classes and subclasses of the invention, where cycle B represents 6-membered heteroaryl ring, containing 1-3 N atoms, and optionally substituted with 1-3 substituents of $R^B$. The compounds containing the following structures of cycle B are non-limiting examples of this class:

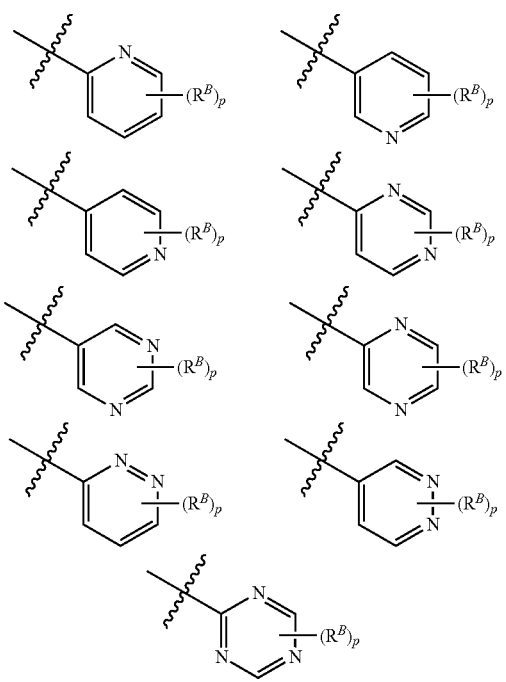

where p is selected from 0, 1, 2, 3.

The non-limiting illustrative examples of the above-indicated variants of cycle B, substituted with $R^B$, appear as follows:

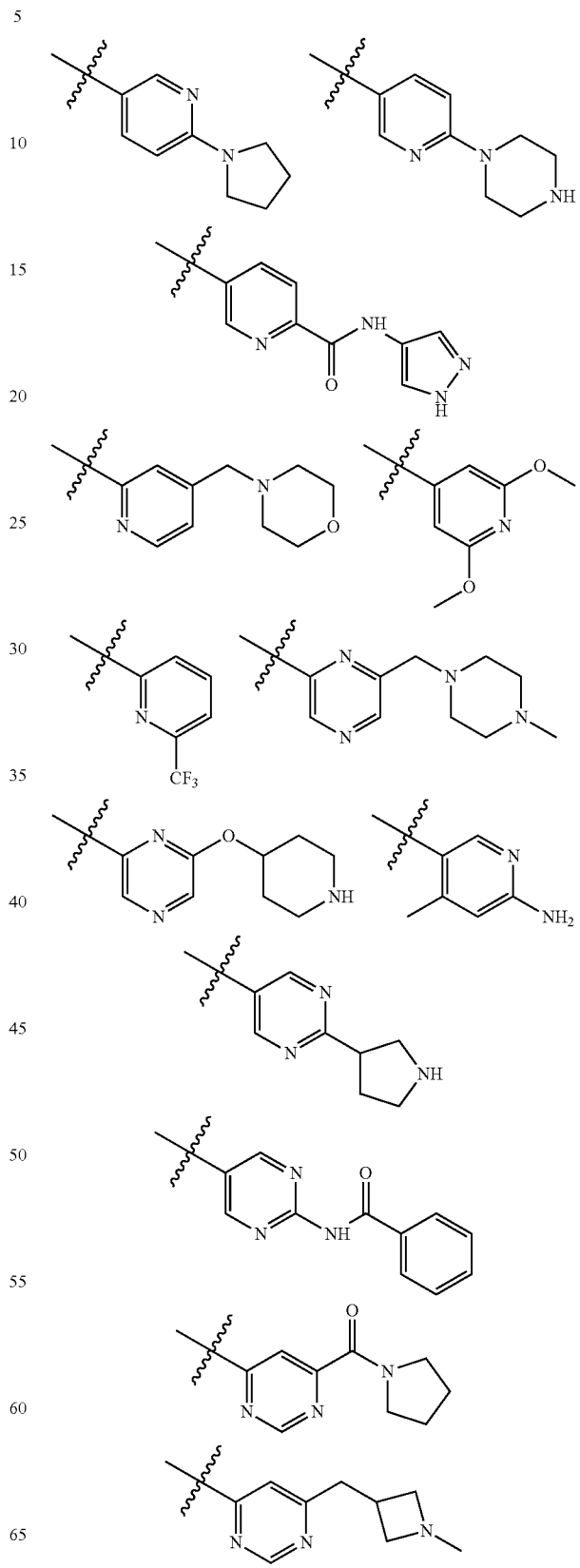

17
-continued

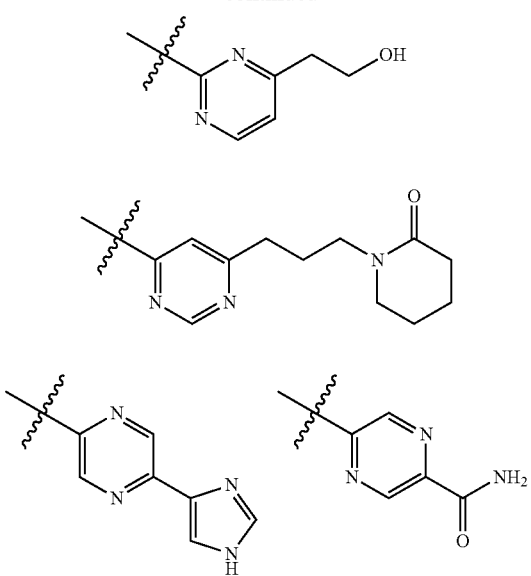

The non-limiting illustrative examples of this class of compounds have the following formulas:

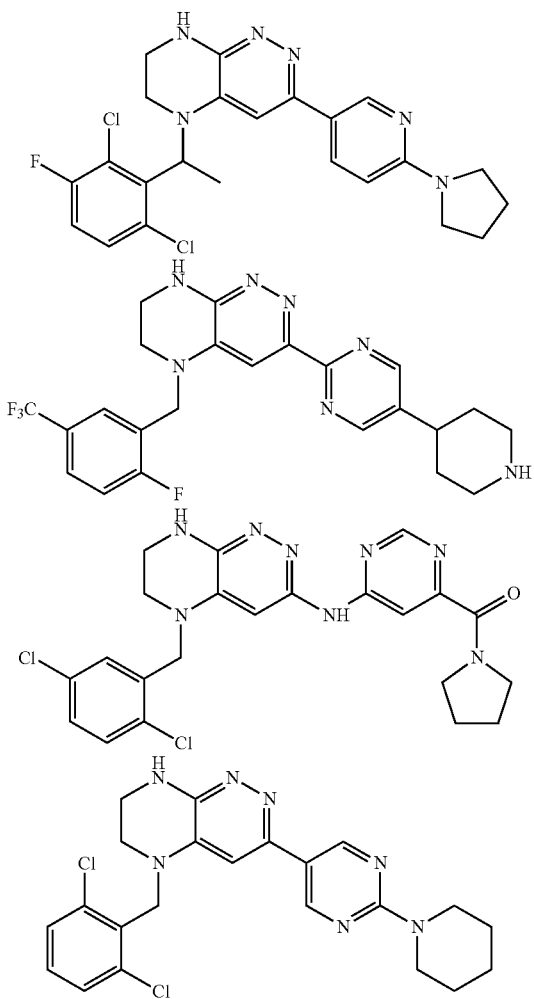

18
-continued

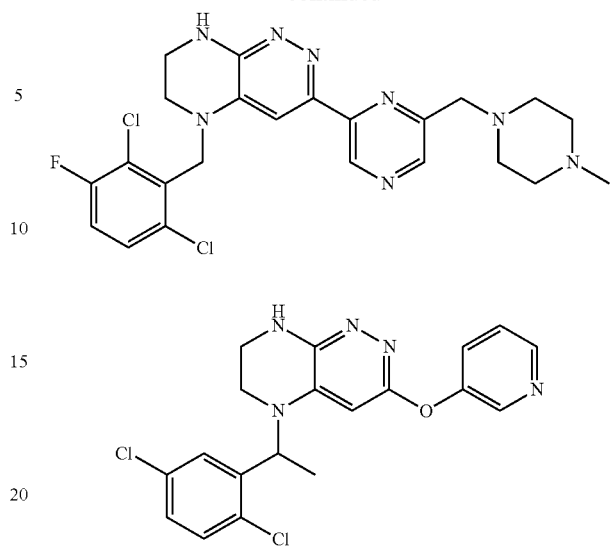

2.15. One of the embodiments of the invention includes compounds of formulas I and IA, where cycle A represents phenyl, optionally substituted with 1-3 groups of $R^A$.

2.16. A subclass of compounds of formulas I and IA or belonging to the other above-indicated subclasses, where $R^A$ group represents halogen, partially or completely halogenated —$C_{1-3}$-alkyl, —O—$C_{1-3}$-alkyl, $S(O)C_{1-3}$-alkyl, $S(O)_2 C_{1-3}$-alkyl, $S(O)NHC_{1-3}$-alkyl, $S(O)_2NHC_{1-3}$-alkyl, $S(O)N(C_{1-3}$-alkyl$)_2$, $S(O)_2N(C_{1-3}$-alkyl$)_2$ or $P(O)(C_{1-3}$-alkyl$)_2$ is of particular interest.

2.17. A subclass of compounds of formulas I and IA or belonging to the other above-indicated subclasses, where $R^A$ group represents Cl, F, $CF_3$ or $OCH_3$ is of particular interest.

2.18. A subclass of compounds of formulas I and IA, where cycle A represents phenyl, and cycle B represents 5-6-membered heteroaryl is of particular interest. The non-limiting illustrative examples of such compounds includes compounds of formulas, given below:

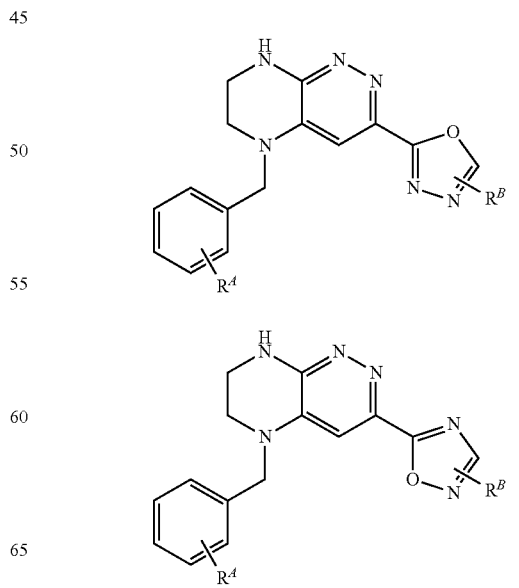

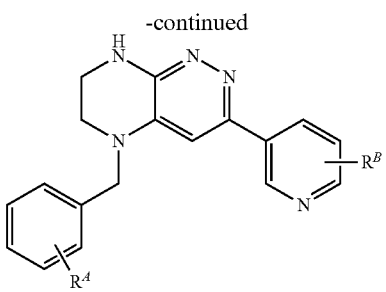

2.19. A subclass of compounds of formula I, where cycle A represents phenyl, $L^B$ linker represents C(O)NH, and cycle B represents phenyl, is of particular interest.

2.20. A subclass of compounds of formula I, where cycle A represents phenyl, $L^B$ linker represents NH, and cycle B represents phenyl, is of particular interest.

Compounds of the present invention of particular interest have one or more of the following characteristics:
- molecular weight less than 1000, preferably less than 750, and most preferably less than 650 g/mol (not including the weight of any co-crystallizing or solvating agents, and counterions in the case of salt); or
- inhibitory activity relative to native or mutant (especially clinically significant mutant) kinases, especially to kinases ALK, MET, ROS1, EGFR or other kinases of interest, with $IC_{50}$ value of 1 μM or less (produced by any scientifically sound experiment of determining kinase inhibition), preferably with $IC_{50}$ of 500 nM or less, and optimally with $IC_{50}$ of 250 nM or less; or inhibitory activity relative to a given kinase with $IC_{50}$ of at least 100 times less than the corresponding $IC_{50}$ values for other kinases of interest; or
- cytotoxic or cytostatic effect relative to tumor cells, specific in vitro, or in animal studies using a scientifically acceptable model (preferred compounds which inhibit the growth of culture cells Ba/F3 NPM-ALK, Ba/F3 EML4-ALK, Karpas 299, SU-DHL-1, NCI-H3122 or NCI-H2228 with efficiency exceeding the efficiency of Crizotinib, preferably with an efficiency of at least twice as better than of Crizotinib, and most preferably with an efficiency of at least 10 times better than of Crizotinib).

Also provided is a method for the treatment and/or prevention of a disease associated with aberrant activity of protein kinases, said method comprising administering of pharmaceutical formulation containing a compound of invention.

In particular, such a disease may include cancer of the lung, bone, pancreas, skin, head and neck, cutaneous or intraocular melanoma, uterine cancer, cancer of ovary, rectum, anal canal, stomach, kidney, breast, carcinoma of the fallopian tubes, mucosa, and cervical cancer, cancer of vagina, vulva, Hodgkin's lymphoma, cancer of the esophagus, small intestine, endocrine system, thyroid, parathyroid, adrenal gland, sarcoma of soft tissues, cancer of the urethra, penis, prostate, chronic or acute myeloid leukemia, lymphocytic lymphomas, bladder cancer, cancer of kidney or ureter, carcinoma of the renal epithelium, renal pelvic carcinoma, rhabdomyosarcoma, neoplastic formations in the central nervous system, primary CNS lymphoma, spinal cord tumor, brain stem glioma, pituitary adenoma, and combinations thereof.

Such disease may also represent a non-small cell lung cancer, anaplastic large cell lymphoma, diffuse B-cell lymphoma, inflammatory myofibroblastic tumor, neuroblastoma, rhabdomyosarcoma, anaplastic thyroid cancer, glioblastoma multiforme, cholangiocarcinoma, adenocarcinoma of the stomach, chronic myelomonocytic leukemia, Ewing's sarcoma, inflammatory carcinoma of breast, carcinoma of papillary renal epithelium, squamous cell carcinoma.

In addition, the invention provides pharmaceutical formulations comprising at least one compound, which is the subject of the invention, either salt, hydrate or other solvate thereof, and at least one pharmaceutically acceptable carrier, adjuvant, diluent and/or excipient. Such formulations are designed for the treatment and/or prevention of a disease associated with the aberrant activity of protein kinases, and can be administered to a subject in need, in order to inhibit the growth, development or metastasis of cancer tumors, including solid tumors (for example, prostate cancer, colon cancer, pancreas, ovarian, breast, esophageal, non-small cell lung cancer (NSCLC), tumor diseases of the brain, including glioblastoma and neuroblastoma; cancer diseases of soft tissues, including rhabdomyosarcoma, etc.), various forms of lymphoma such as non-Hodgkin's lymphoma (NHL) known as anaplastic large cell lymphoma (ALCL), various forms of leukemia and other forms of cancer, including those resistant to treatment with Crizotinib or other kinase inhibitors, and generally for the treatment and prevention of diseases or adverse conditions of the body caused by one or more kinases that are inhibited by the compounds of the invention.

The present invention also relates to a method of treatment of cancer, which, according to the present invention, comprises administering (as a monotherapy or in combination with one or more anti-cancer agents, one or more agents to mitigate the adverse events, radiation, etc.) a therapeutically effective amount of the compound being the subject of the invention to a human or animal body in need of stopping, slowing, or reversing the growth, development or spread of cancer, including solid tumors and other forms of cancer, such as leukemia. Such administration represents a method of treatment and prevention of the disease caused by one or more kinases inhibited by one of the disclosed compounds or their pharmacologically acceptable derivatives. "Administration" of a compound of the present invention includes delivery to the recipient of the compound described in the present invention, prodrug, or other pharmacologically acceptable derivative of such a compound, using any acceptable agents or routes of administration for the body, as described herein. As a rule, the compound is administered to a patient once or several times a week, for example, daily, every other day, 5 days a week, etc. Oral and intravenous administrations are of particular interest.

The invention also includes the preparation of compounds of any of formulas I, IA, or any of other compounds of the present invention.

In addition, the invention also includes the use of a compound of the invention or its pharmacologically acceptable derivative in the manufactore of a medicinal product for the treatment of both acute and chronic forms of cancer (including lymphoma and solid tumors, primary or metastatic, including the types of cancer mentioned herein, and including types of cancer resistant or tolerant to one or more modes of treatment). The compounds of invention can be useful in the manufacture of anticancer drugs. The compounds of the present invention may also be useful in the manufactore of the medicinal products to attenuate or prevent various disorders by inhibiting one or more kinases, including but not limited to kinases such as ALK, EGFR, MET, ROS1.

The invention also encompasses a composition comprising compounds of the invention, including compounds of any of the described classes or subclasses, in particular any of the formulas mentioned above, among others, preferably in a therapeutically effective amount, in conjunction with at least one therapeutically acceptable carrier, adjuvant or diluent.

The compounds of the present invention may also be used as standards and reagents for the characterization of various kinases, including, but not limited to, ALK, EGFR, MET, ROS1 kinases, as well as for studying the role of kinases in biological and pathological phenomena; for the study of intracellular pathways of signal transduction, carried out by such kinases, for the comparative evaluation of new kinase inhibitors; and for studying various types of cancer in models of cell lines and in animals.

3. DEFINITIONS

The following definitions apply herein unless otherwise specified. Furthermore, unless otherwise indicated, all occurrences of the functional groups are selected independently. This is indicated by the use of the prime symbol for the given definition, the two occurrences can be the same or different (for example, R, R', R"; Y, Y', Y" and etc.).

3.1. The term "aliphatic" means herein both saturated and unsaturated (but not aromatic) straight (i.e., unbranched), branched, cyclic or polycyclic non-aromatic hydrocarbon chain, a residue, which may be optionally substituted with one or more functional groups. Unless otherwise explicitly specified, alkyl, other aliphatic, alkoxy and acyl groups generally contain 1-8 (i.e., $C_{1-8}$), and in most cases 1-6 ($C_{1-6}$) adjacent aliphatic carbon atoms. As an example, such aliphatic groups include methyl, ethyl, isopropyl, cyclopropyl, methylene, methylcyclopropyl, cyclobutylmethyl, cyclopentyl derivatives, etc., which may contain one or more substituents. The term "aliphatic" is thus intended to include alkyl, alkenyl, alkynyl, cycloalkyl and cycloalkenyl fragments.

The term "alkyl" means herein both unbranched and branched, cyclic or polycyclic alkyl groups. Similar conformities apply to other generic terms such as "alkenyl", "alkynyl", etc. Furthermore, "alkyl", "alkenyl", "alkynyl" and the like groups may be either substituted or unsubstituted.

3.2. The term "alkyl" refers herein to groups usually having one to eight, preferably one to six carbon atoms. For example, "alkyl" may refer to methyl, ethyl, n-propyl, isopropyl, isohexyl, cyclohexyl, and etc. As an illustration, substituted alkyl groups include, but are not limited to, the following groups: fluoromethyl, difluoromethyl, trifluoromethyl, benzyl, substituted benzyl, phenethyl, substituted phenethyl, etc. The term $C_{1-6}$ alkyl means alkyl containing from 1 to 6 carbon atoms and includes $C_1$, $C_2$, $C_3$, $C_4$, $C_5$ и $C_6$-alkyl groups.

3.3. The term "alkoxy" refers to the alkyl groups as defined above, which are attached to the molecule via a bridging oxygen atom. For example, the term "alkoxy" means —O-alkyl, wherein the alkyl group contains from 1 to 8 carbon atoms in a linear (unbranched) or branched chain or in the form of ring. As an illustration, alkoxy groups include, but are not limited to, the following groups: methoxy, ethoxy, n-propoxy, n-butoxy, tert-butoxy, etc.

3.4. The term "haloalkyl" includes branched and linear saturated hydrocarbon chains wherein one or more hydrogen atoms are substituted with halogen. Examples of haloalkyl groups include, but are not limited to, the following groups: trifluoromethyl, trichloromethyl, pentafluoroethyl, —C(CF$_3$)$_2$CH$_3$, etc.

3.5. The term "alkenyl" refers to groups usually having from two to eight, more typically from two to six carbon atoms and including linear and branched hydrocarbon chains or rings, and having one or more double carbon-carbon bonds and arranged at any stable point in the ring or chain. For example, "alkenyl" may mean, but not limited to, the following groups: prop-2-enyl, but-2-enyl, but-3-enyl and etc. The term "alkynyl" refers to groups usually having from two to eight, more typically from two to six carbon atoms and including linear and branched hydrocarbon chains or rings and one or more triple carbon-carbon bonds. For example, "alkynyl" may mean, but not limited to, the following groups: prop-2-enyl, but-2-enyl, but-3-enyl, hex-2-enyl, hex-5-enyl, etc.

3.6. The term "cycloalkyl" refers to groups having from three to 12, typically from three to ten carbon atoms in a mono-, di- or polycyclic (i.e., ring) structure. As an illustration, cycloalkyls include, but are not limited to, the following radicals: cyclopropyl, cyclobutyl, cyclopentyl, and etc., which, as in the case of other aliphatic, heteroaliphatic or heterocyclic substituents, may be substituted. The terms "cycloalkyl" and "carbocycle" are equivalent. The term "cycloalkenyl" refers to alkenyl groups having from three to 13, usually from 5 to 8 carbon atoms in a mono- or polycyclic structure containing one or more unsaturated double carbon-carbon bond. For example, "cycloalkenyl" may mean, but is not limited to, the following groups: cyclopentenyl, cyclohexane, etc.

3.7. The term "heteroaliphatic" herein means aliphatic substituents, which comprise atom of oxygen, sulfur, nitrogen, phosphorus or silicon in place of one or more carbon atoms. Heteroaliphatic substituents may be unbranched, branched or cyclic, as well as include acyclic units such as CH$_3$OCH$_2$CH$_2$O—, as well as heterocycles such as morpholino, pyrrolidinyl, etc.

3.8. The term "heterocycle", "heterocyclyl" or "heterocyclic" used herein means non-aromatic cyclic systems having from five to fourteen, usually from five to ten cycle Atoms in which there are one or more carbon cycles, usually from one to four in which there is substitution with a heteroatom such as N, O or S. Examples of heterocyclic rings include, but are not limited to, the following: tetrahydrofuran-2-yl, tetrahydrofuran-3-yl, tetrahydrothiophen-2-yl, morpholine-2-yl, thiomorpholine-4-yl, piperazin-1-yl, piperazin-2-yl, phthalimidine-1-yl, benzoxolanil, etc. In addition, the term "heterocycle" or "heterocyclic" in the sense as used herein, covers the groups in which a non-aromatic ring containing a heteroatom is connected with one or more aromatic or non-aromatic rings, such as indolinyl, chromanyl, and etc., in which radical atom or a point of attachment is placed at a non-aromatic ring containing a heteroatom. The terms "heterocycle", "heterocyclyl" or "heterocyclic" also apply to rings, saturated or partially unsaturated, which may be substituted.

3.9. The term "aryl", used alone or as part of a larger unit, such as "aralkyl", "aralkoxy", or "aryloxyalkyl", refers to groups containing an aromatic ring, or polycyclic aromatic systems having from six to fourteen carbon atoms. Examples of usable cyclic aryl groups include, but are not limited to, groups such as phenyl, naphthyl, phenanthryl, anthryl, phenanthryl and the like, as well as naphth-1-yl, naphth-2-yl, anthracen-1-yl and anthracen-2-yl. Furthermore, the term "aryl", as used herein, includes groups in which an aromatic ring is connected to one or more non-aromatic rings, such as indanyl, phenanthridinyl or tetrahydronaphthyl, where the radical atom or joint place belong to aromatic ring.

3.10. The term "heteroaryl" as used herein means stable heterocyclic and polyheterocyclic aromatic moieties having 5-14 cycle Atoms. The heteroaryl group may be substituted or unsubstituted and may contain one or more rings. Possible substituents include, without limitation, any of the previously mentioned substituents. Examples of typical heteroaryl rings include five- and six-membered monocyclic groups such as thienyl, pyrrolyl, imidazolyl, pyrazolyl, pyridyl, pyrimidinyl, pyridazinyl, triazinyl, etc.; and polycyclic heterocyclic groups such as benzo[b]thienyl, naphtho [2,3-b]thienyl, thianthrenyl, isobenzofuranyl, chromenyl, isoindolyl, benzimidazole, pteridinyl, etc. (see e.g. A. R Katritzky, Handbook of Heterocyclic Chemistry). Furthermore, heteroaryl groups include groups in which the heteroaromatic ring is connected to one or more aromatic or non-aromatic rings, and the radical atom or point of attachment belong to heteroaromatic ring. Examples include tetrahydroquinolinyl, tetrahydroisoquinolinyl, and pyrido [3,4-d]pyrimidinyl. The term "heteroaryl" also includes rings with possible substituents. The term "heteroaryl" may be used equivalently to terms "heteroaryl ring" or "heteroaromatic".

3.11. The aryl group (including the aryl portion of aralkyl, aralkoxy or aryloxialkyl-groups and etc.) or heteroaryl group (including the heteroaryl portion of heteroaralkyl or heteroaralkoxy units and etc.) may contain one or more substituents. Examples of suitable substituents on the unsaturated carbon atom of the aryl or heteroaryl group include halogen (F, Cl, Br or I), alkyl, alkenyl, alkynyl, —CN, —R, —OR, —S(O)$_p$R (where p is selected from 0, 1, 2), —SO$_2$NRR', —NRR', —(CO)YR, —O(CO)YR, —NR(CO)YR', —S(CO)YR, where each occurrence of Y represents independent —O—, —S—, —NR— or covalent chemical bond; consequently, —YR includes —R, —OR, —SR и —NRR', and —(CO)YR includes —C(=O)R, —C(=O)OR, and —C(=O)NRR'. Additional substituents include —YC(=NR)NR'R", —COCOR, —COMCOR (where M—aliphatic group containing 1-4 carbon atoms), —YP(=O)(Y'R)(Y"R'), —NO$_2$, —NRSO$_2$R' and —NRSO$_2$NR'R". For further illustration, substituents, where Y is —NR thus include, among others, —NRC(=O) R', —NRC(=O)NR'R", —NRC(=O)OR' and —NRC (=NH)NR'R". Substituents R, R' and R" include hydrogen, alkyl, alkenyl, alkynyl, cycloalkyl, cycloalkenyl, aryl, heteroaryl, heterocycle. It should be noted that the substituents R may in turn be substituted or unsubstituted. Thus, the substituent R includes, but is not limited to, haloalkyl and halogenaryl groups (such as chloromethyl, trichloromethyl or halophenyl); alkoxyalkyl and alkoxyaryl groups (such as methoxyethyl, mono-, di- and trialkoxyphenyl; methylenedioxyphenyl or ethylenedioxyphenyl); alkylamino groups. In addition, illustrative examples include 1,2-methylenedioxy, 1,2-ethylenedioxy, protected OH (such as acyloxy), phenyl, substituted phenyl, —O-phenyl, —O-(substituted) phenyl,-benzyl, -substituted benzyl, —O-phenethyl, —O-(substituted) phenethyl, etc. Moreover, examples of the substituents include amino, alkylamino, dialkylamino groups, aminocarbonyl, halogen, alkyl, alkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy and haloalkyl groups.

Aliphatic, heteroaliphatic or non-aromatic heterocyclic group may also contain one or more substituents. Examples of suitable substituents of such groups include all the above-indicated substituents for carbon atoms of an aryl or heteroaryl group, and in addition include the following substituents for the saturated carbon atom: =O, =S, =NR, =NNRR', =NNHC(O)R, =NNHCOR, or =NNHSO$_2$R, where R represents hydrogen, alkyl, alkenyl, alkynyl, cycloalkyl, aryl, heteroaryl, heterocycle. Illustrative examples of substituents of the aliphatic, heteroaliphatic or heterocyclic group include amino, alkamino, dialkamino, aminocarbonyl, halogen, alkyl, alkylaminocarbonyl, dialkylaminocarbonyl, alkylaminocarbonyloxy, alkoxy, nitro, cyano, carboxy, alkoxycarbonyl, alkylcarbonyl, hydroxy, haloalkoxy, or haloalkyl groups.

Illustrative examples of the substituents on the nitrogen atom of an aromatic or non-aromatic heterocycle include R, —NRR', —C(=O)R, —C(=O)OR, —C(=O)NRR', —C(=NR)NR'R", —COCOR, —COMCOR (where M—aliphatic group containing 1-4 carbon atoms), —CN, —NRSO$_2$R' and —NRSO$_2$NR'R', where R represents hydrogen, alkyl, alkenyl, alkynyl, cycloalkyl, aryl, heteroaryl and heterocycle.

3.12. The present invention encompasses only those combinations of substituents and derivatives, which form stable or chemically feasible compound. Stable or chemically feasible compound is one that has stability sufficient to permit its preparation and detection. Preferred compounds of this invention are sufficiently stable and do not decompose at temperatures up to 40° C. in the absence of chemically reactive conditions, for at least one week.

3.13. Certain compounds of this invention may exist in tautomeric forms and the invention includes all such tautomeric forms of such compounds, unless otherwise specified.

3.14. Unless otherwise stated, structures depicted herein also refer to all stereoisomers thereof, i.e. R- and S-isomers for each asymmetric center. Furthermore, separate stereochemical isomers, as well as enantiomers and diasteromeric mixtures of these compounds, are also the subject of this invention. Thus, the present invention includes each diastereomer or enantiomer, to a large extent free of other isomers (>90%, and preferably >95% of mole purity), as well as the mixtures of such isomers.

The specific optical isomer can be obtained by separation of the racemic substance according to standard procedures, for example by obtaining diastereoisomeric salts by use of an optically active acid or base, followed by separation of the mixture of diastereoisomers by crystallization followed by isolation of the optically active bases from these salts. Examples of appropriate acids are tartaric, diacetyltartaric, dibenzoyltartaric, ditoluenetartaric and camphorsulfonic acid. Another technique for separation of optical isomers lies in the use of a chiral chromatography column. Furthermore, another separation method involves synthesis of covalent diastereoisomeric molecules by reacting compounds of the invention with an optically pure acid in an activated form or an optically pure isocyanate. The resulting diastereomers can be separated by conventional methods, such as chromatography, distillation, crystallization or sublimation, and then hydrolyzed to obtain the enantiomerically pure compound.

The optically active compounds of this invention may be prepared using optically active initial materials. These isomers may be in the form of a free acid, a free base, an ester or salt thereof.

3.15. The compounds of this invention can exist in radiolabeled form, i.e. these compounds may contain one or more atoms which atomic weight or mass number differ from the atomic weight or mass number of most common natural isotopes. Radioisotopes of hydrogen, carbon, phosphorous, chlorine include $^3H$, $^{14}C$, $^{32}P$, $^{35}S$, and $^{36}Cl$, respectively. Compounds of this invention, which contain those radioisotopes and/or other radioisotopes of other atoms are within the scope of the present invention. Tritium, i.e. $^3H$, and carbon, i.e. $^{14}C$ radioisotopes are particularly preferred due to the ease of preparation and detection.

The radiolabeled compounds of the present invention can be prepared by methods well known to those skilled in the art. Labeled compounds can be prepared by procedures described herein, by the simple replacement of the unlabeled reagents with respective labeled reagents.

Implementation of the Invention

4. SYNTHETIC OVERVIEW

The compounds of the present invention may be prepared using the synthetic methods described below. These methods are not exhaustive and allow the introduction of reasonable modifications. The indicated reactions may be carried out using suitable solvents and materials. In implementing these common methodologies for the synthesis of specific substances one shall consider functional groups present in substances and their influence on the course of reaction. It is necessary to change the order of the steps or to give preference to one of several alternative schemes of synthesis for some substances.

The protective group—the functional group being introduced in the molecule of a chemical compound for chemoselectivity flow of necessary chemical reaction. Protective groups are important in organic synthesis. Some reagents used in organic synthesis can interact directly with many functional groups of the reformable molecule. In that case, if it is necessary to perform the reaction with only one type of the functional groups, without affecting the others, the last shall be modified ("protected") by protective groups. Tert-butoxycarbonyl group (Boc) may be example of the protective group.

Synthesis of compounds of the present invention can be performed according to Schemes I-XIII under the standard methods.

4.1. Intermediates for most compounds of formulas I and IA—compounds I-1, I-2, I-3 and I-4—can be prepared according to Scheme I.

The first stage includes the synthesis of mono-Boc-substituted ethylenediamine, of which intermediate I-1 is obtained by reductive amination at the second stage. Interaction of this intermediate with 3,4,6-trichloropyridazine in the presence of base results in the substitution of the chlorine atom in the 4 position of the pyridazine ring. Interaction of the resulting compound with trifluoroacetic acid leads to the removal of protective Boc-group. The next stage includes the intramolecular nucleophilic substitution reaction, leading to the preparation of bicyclic product, which interaction with Boc-anhydride leads to intermediate I-2. Carbonylation of this intermediate in methanol in the presence of a palladium catalyst leads to obtaining methyl ester I-3, which hydrolysis with lithium hydroxide followed by acidification leads to obtaining acid I-4.

Scheme I

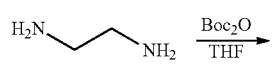

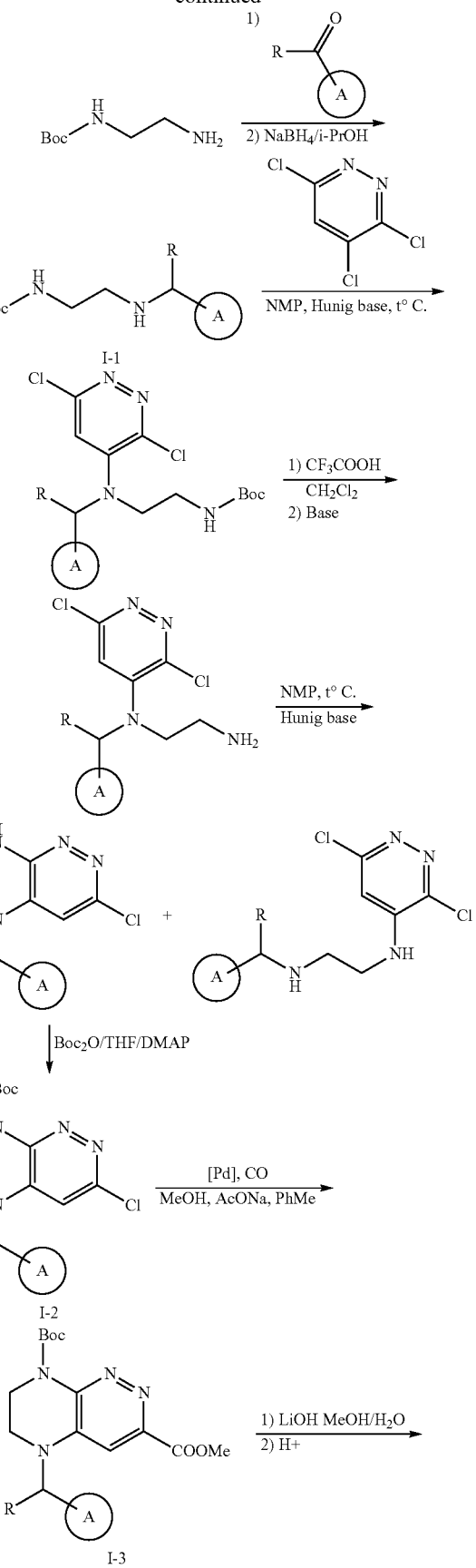

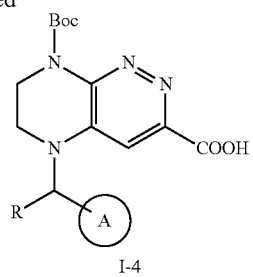

I-4

Cycle A in Scheme I is defined as in p. 1.1. of the description of the invention, and substituent R is —H or —CH₃.

4.2. Compounds of the formula IA, in which the cycle A is as defined in p. 1.1 of the description of the invention, substituent R is —H or —CH₃, cycle B represents 1,2,4-oxadiazole, $L^B$ represents a covalent chemical bond, and the substituent $R^B$ is attached to the position 3 and is defined according to p. 1.1 of the description of the invention, can be prepared from intermediate I-4 under Scheme IIa.

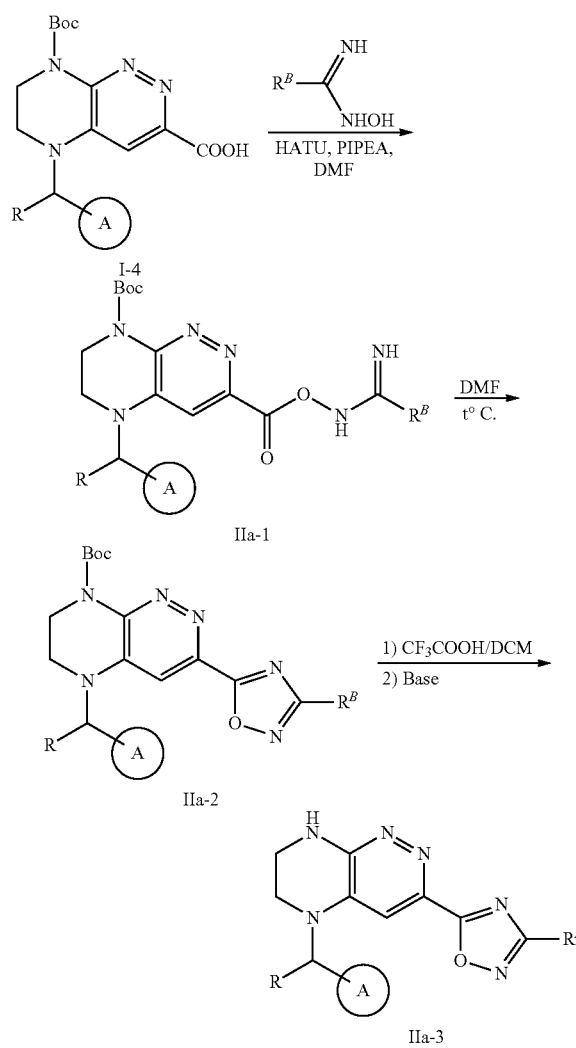

At the first stage, the reaction, activated using HATU acid I-4 with an amidoxime, leads to the formation of O-acyl-amideoxime, which is then cyclized by heating in DMF with formation of the corresponding oxadiazole. At the last stage, the removal of the protective Boc group takes place.

Compounds of the formula IA, in which the cycle A is as defined in p. 1.1 of the description of the invention, substituent R is —H, —CH₃, cycle B is 1,2,4-oxadiazole, $L^B$ represents a covalent chemical bond, and the substituent $R^B$, defined under p. 1.1 of the description of the invention, is attached to position 5, can be prepared from intermediate I-2 according to Scheme IIb.

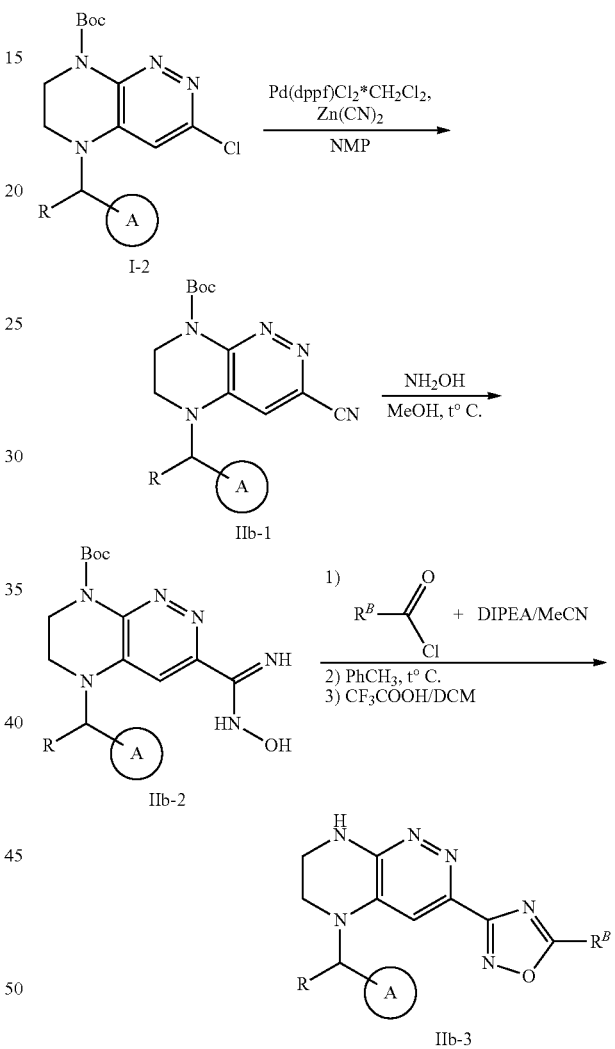

At the first stage, the palladium catalyzed nucleophilic substitution of the chlorine atom to a nitrile group is carried out by the action of zinc cyanide. The resulting nitrile is treated with hydroxylamine in methanol, leading to amidoxime IIb-2. Acylation of the obtained amidoxime by the corresponding acid chloride in the presence of a base, heating the product in toluene and removing the protective Boc-group by treatment with trifluoroacetic acid lead to the target compound.

4.3. Compounds of the formula IA, in which the cycle A is as defined in p. 1.1 of the description of the invention, R is —H, —CH₃, cycle B is 1,2,3-oxadiazole, and $L^B$ represents a covalent chemical bond, can be prepared from intermediate I-3 according to Scheme III.

Scheme III

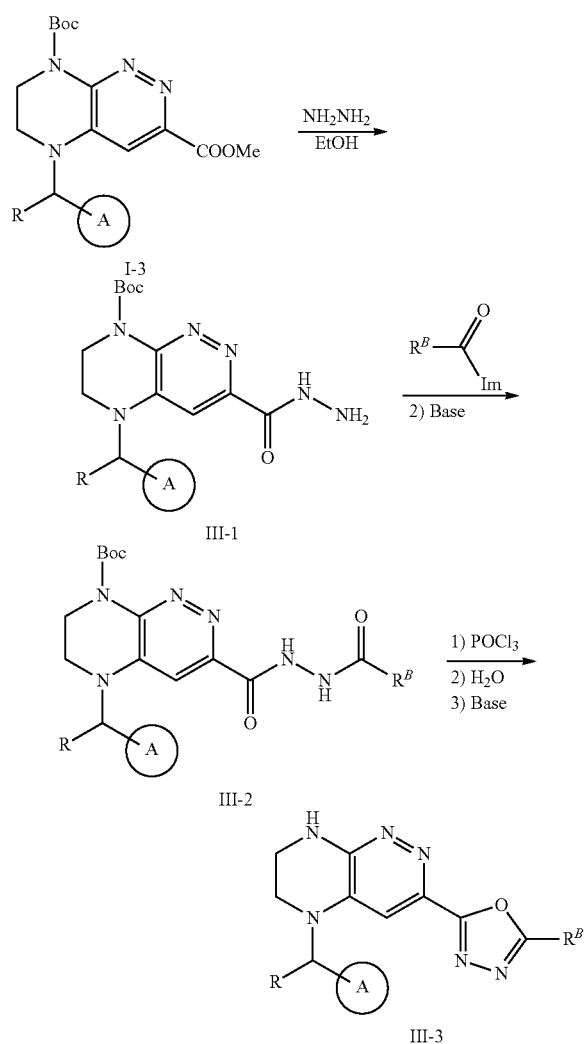

At the first stage, the reaction of the methyl ester I-3 with a hydrazine leads to obtaining the corresponding hydrazide, which is then subjected to acylation with carboxylic acid imidazolide with the formation of diacylhydrazine. Intermediate III-2 is subjected to reaction with phosphorus oxychloride in which cyclization occurs with formation of the target compound.

4.4. Compounds of the formula IA, in which the cycle A is as defined in p. 1.1 of the description of the invention, substituent R is —H, —CH$_3$, cycle B is 1,2,4-triazole, and L$^B$ represents a covalent chemical bond, can be prepared from intermediate I-2 according to Scheme IV.

Scheme IV

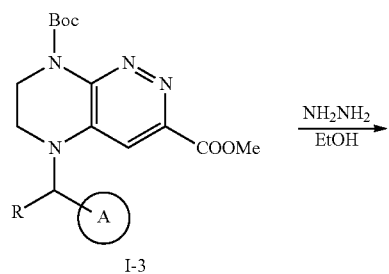

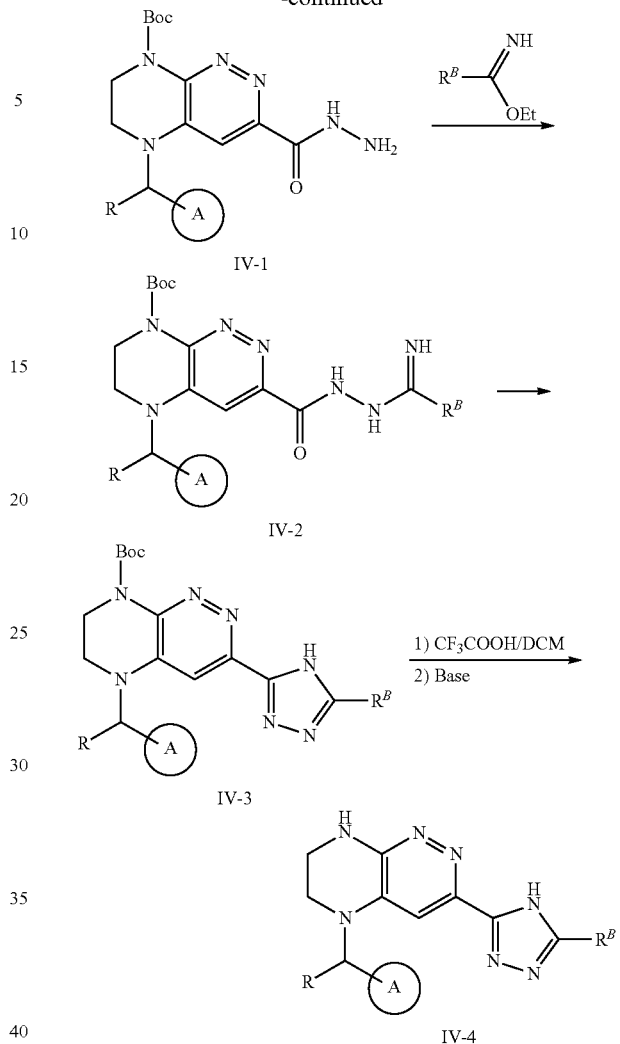

At the first stage, the reaction of the methyl ester I-3 with a hydrazine leads to formation of the corresponding hydrazide, which is then reacted with an amino ether. Heating the resulting intermediate leads to the formation of triazole from which protective Boc-group is removed at the last stage.

4.5. Scheme Va can be used for the synthesis of compounds of formula IA, in which the cycle A is as defined in p. 1.1 of the description of the invention, substituent R is —H, —CH$_3$, L$^B$ represents a covalent chemical bond, and cycle B is as defined in p. 1.1 of the description of the invention

Scheme Va

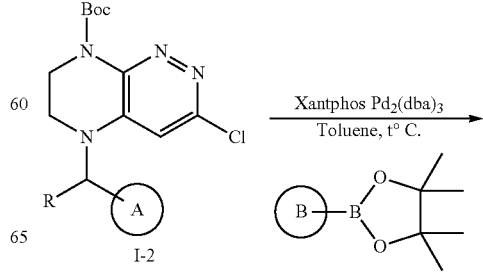

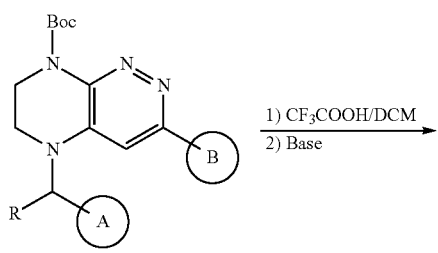

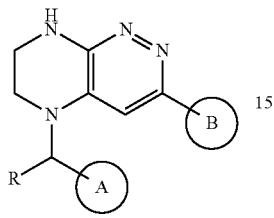

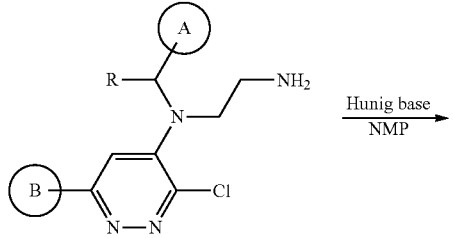

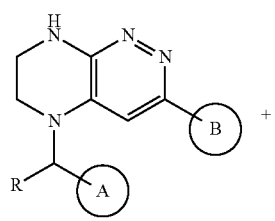

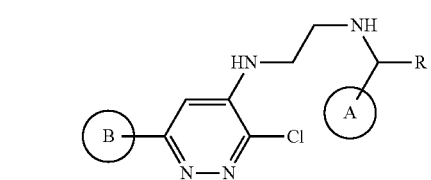

Palladium catalyzed reaction of intermediate I-2 with pinacolborane by Suzuki reaction leads to the formation of the intermediate, removing the protective group, from which the target compound is obtained.

Alternatively, Scheme Vb can be used for the synthesis of compounds of formula IA, wherein $L^B$ represents a covalent chemical bond:

Scheme Vb

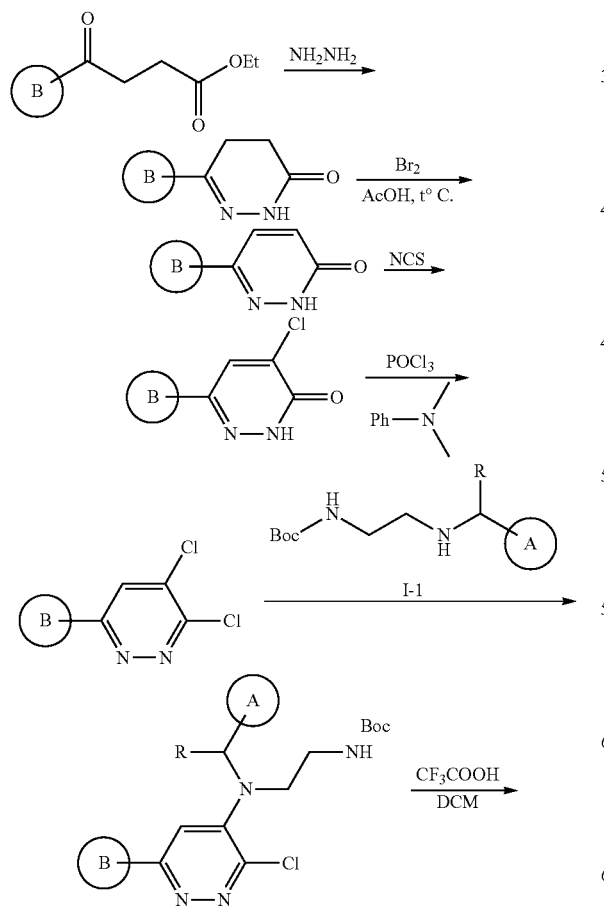

At the first stage, the reaction with hydrazine leads to the formation of cyclic hydrazide, which is then oxidized by the action of bromine in acetic acid. The resulting intermediate is chlorinated with N-chlorosuccinimide. The product of this reaction is treated with phosphorus oxychloride. Interaction of the resulting intermediate with Boc-substituted derivative of ethylenediamine I-1, protective Boc-group removal under action of trifluoroacetic acid and subsequent cyclization lead to obtaining target product.

4.6. Scheme VIa or VIb can be used for the synthesis of compounds of formula I, in which the cycle A is as defined in p. 1.1 of the description of the invention, substituent R is —H, —CH$_3$, $L^B$ represents C(O)NHC$_{0-3}$-alkyl and cycle B is as defined in p. 1.1 of the description of the invention.

Scheme VIa

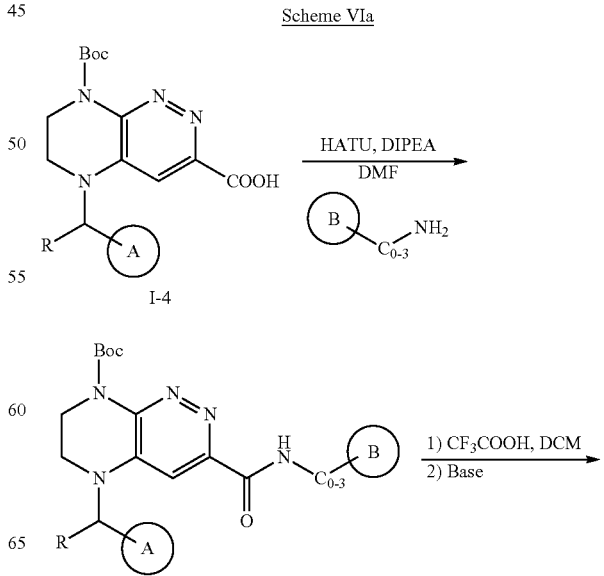

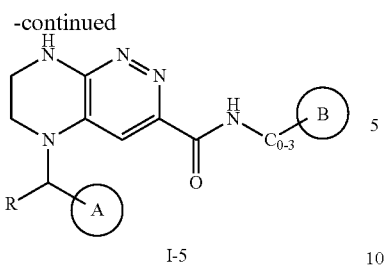

I-5

At the first stage, the carboxylic acid is activated using HATU and the reaction with the amine compound, leading to amide. Removal of protective Boc-group under action of trifluoroacetic acid leads to the target compound.

Scheme VIb

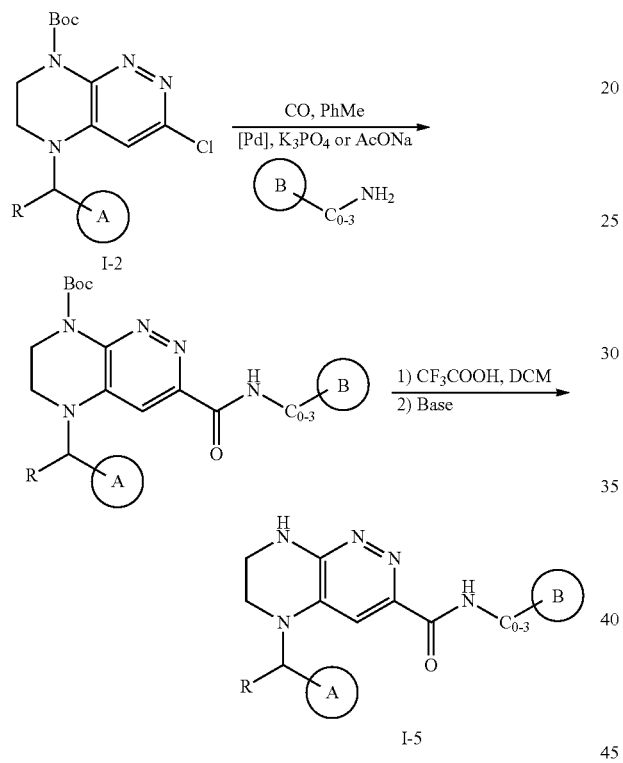

Palladium-catalyzed carbonylation of the compound I-2 with carbon monoxide in the presence of amine compound leads to amide, the removal of protective Boc-group from which leads to the target compound.

Synthesis of compounds of the formula I, in which the cycle A is as defined in p. 1.1 of the description of the invention, substituent R is —H, —CH₃, L^B represents CH₂NH, and cycle B is as defined in p. 1.1 of the description of the invention, is carried out according to the Scheme VIc of compound I-5, prepared according to Scheme VIa or VIb.

Scheme VIc

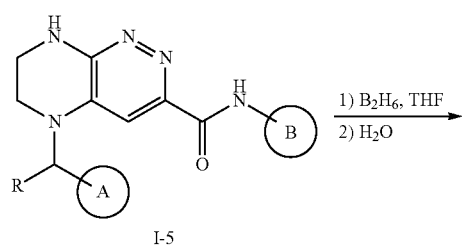

I-5

Reduction of compound I-5 with diborane leads to the target compound.

4.7. Scheme VIIa or VIIb can be used for the synthesis of compounds of formula I, in which the cycle A is as defined in p. 1.1 of the description of the invention, substituent R is —H, —CH₃, L^B represents NH, and cycle B is as defined in p. 1.1 of the description of the invention.

Scheme VIIa

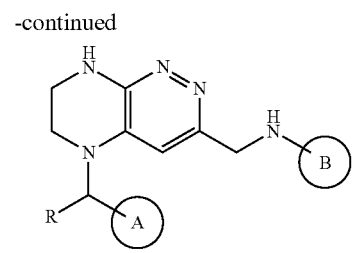

I-2

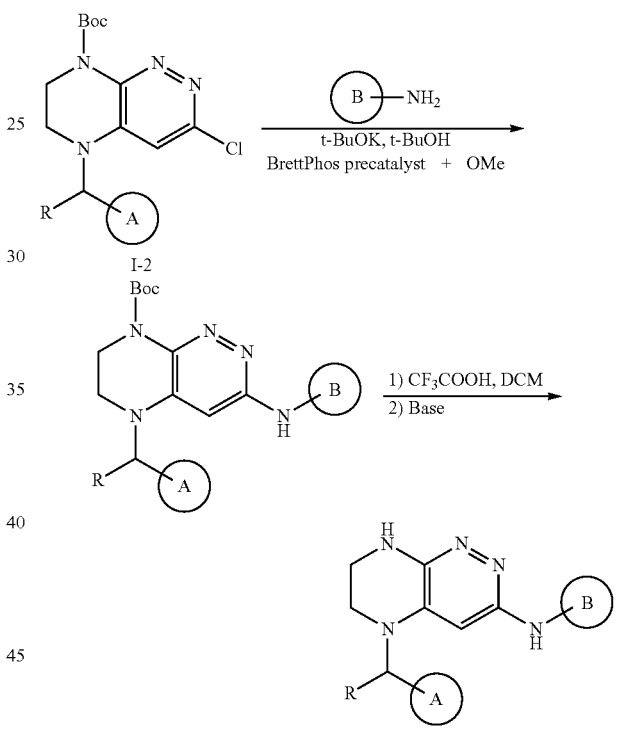

Palladium-catalyzed nucleophilic substitution of the chlorine atom by the action of the amino compound followed by removal of protective Boc-group leads to the target compound.

Scheme VIIb

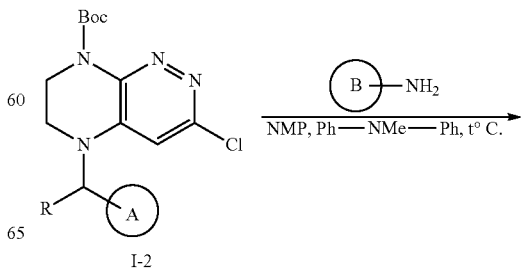

I-2

-continued

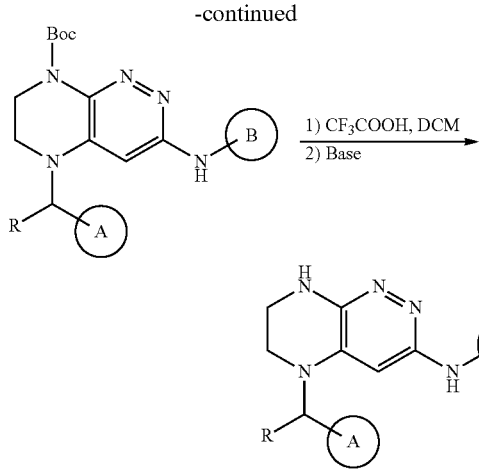

Nucleophilic substitution of the chlorine atom by the action of the amino compound followed by removal of protective Boc-group leads to the target compound.

4.8. The compounds of formula I, in which the cycle A is as defined in p. 1.1 of the description of the invention, substituent R is —H, —CH$_3$, L$^B$ represents —X—, cycle B is as defined in p. 1.1 of the description of the invention, and X represents —O— or —S—, may be synthesized under Scheme VIIIa.

Scheme VIIIa

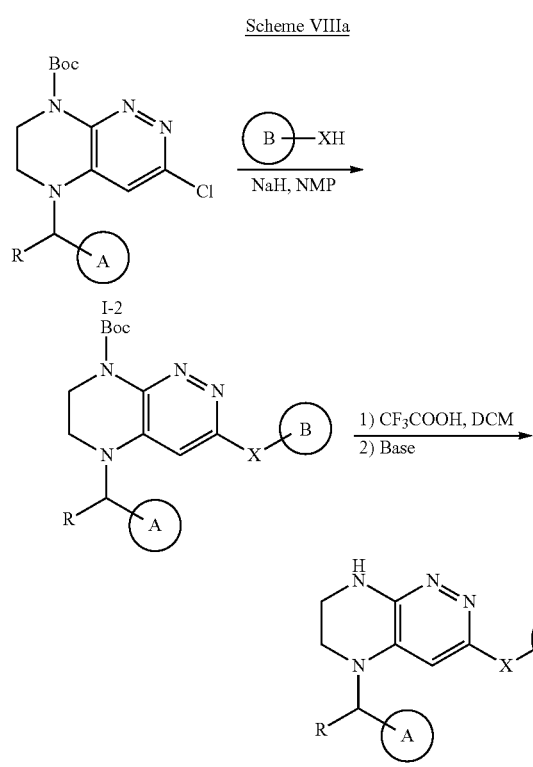

Nucleophilic substitution of the chlorine atom by the action of alcoholate- or thiolate anion (prepared by interaction of sodium hydride with a corresponding alcohol) followed by removal of protective Boc-group leads to the target compound.

Synthesis of compounds of the formula I, in which the cycle A is as defined in p. 1.1 of the description of the invention, substituent R is —H, —CH$_3$, L$^B$ represents —X—C$_{1-3}$- alkyl, cycle B is phenyl optionally having 1-5 substituents of R$^B$, and X represents —O— or —S—, is carried out under Scheme VIIIb.

Scheme VIIIb

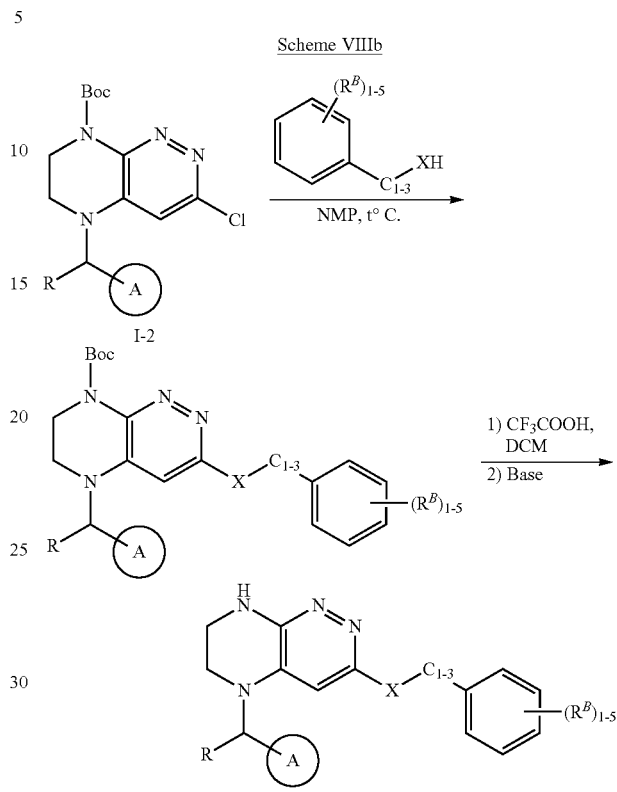

Nucleophilic substitution of the chlorine atom in the initial compound by the action of alcoholate or thiolate followed by removal of protective Boc-group leads to the target compound.

4.9. The compounds of formula I, in which the cycle A is as defined in p. 1.1 of the description of the invention, substituent R is —H, —CH$_3$, L$^B$ represents —NHC(O)C$_{0-3}$- alkyl, and cycle B is as defined in p. 1.1 of the description of the invention, may be synthesized under Scheme IX.

Scheme IX

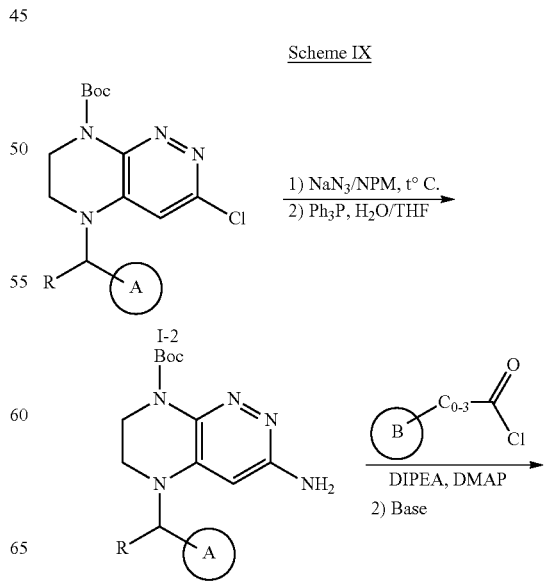

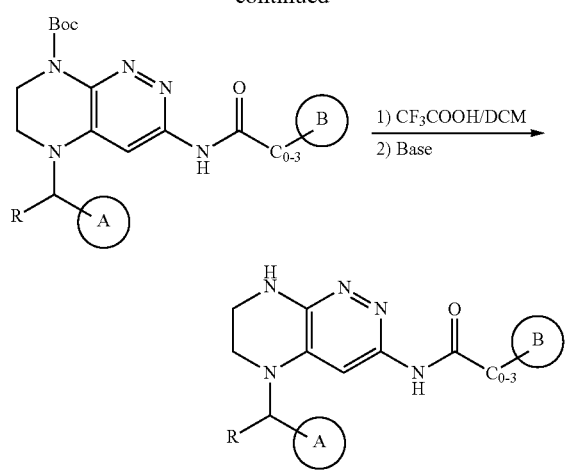

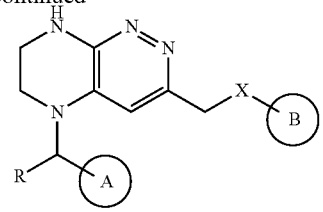

Nucleophilic substitution of the chlorine atom to an azido group with its subsequent breakage by the action of triphenylphosphine leads to obtaining amino compound which acylation with the corresponding carboxylic acid chloride with subsequent removal of the protective results in the target compound.

4.10. The compounds of formula I, in which the cycle A is as defined in p. 1.1 of the description of the invention, substituent R is —H, —CH$_3$, L$^B$ represents —CH$_2$X—, cycle B is as defined in p. 1.1 of the description of the invention, and X represents O or S, may be synthesized under Scheme X.

Scheme X

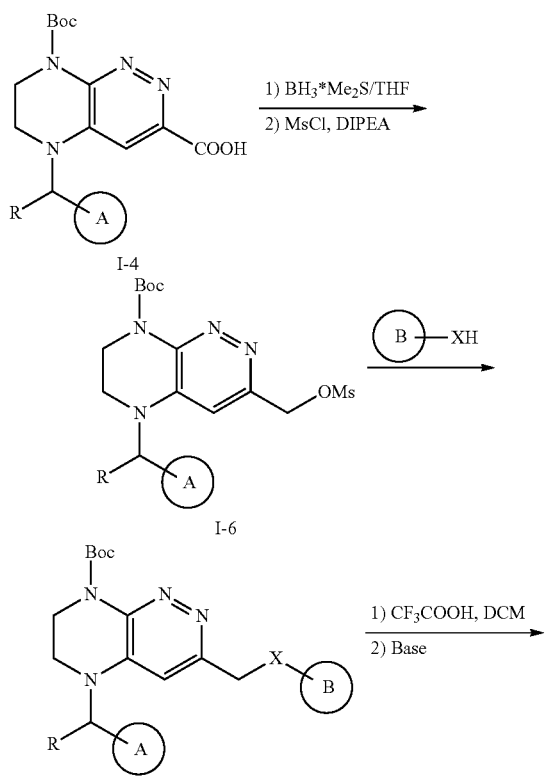

At the first stage, reduction of acid I-4 to the benzyl alcohol is carried out by the action of borane-dimethyl sulfide complex. Mesylation of the obtained alcohol, following nucleophilic substitution under the action of the corresponding alcoholate or thioalcoholate and removal of the protective group lead to obtaining target compound.

4.11. The compounds of formula I, in which the cycle A is as defined in p. 1.1 of the description of the invention, substituent R is —H, —CH$_3$, L$^B$ represents —CH$_2$C(O)NH, cycle B is as defined in p. 1.1 of the description of the invention, and X represents O or S, may be synthesized under Scheme XI.

Scheme XI

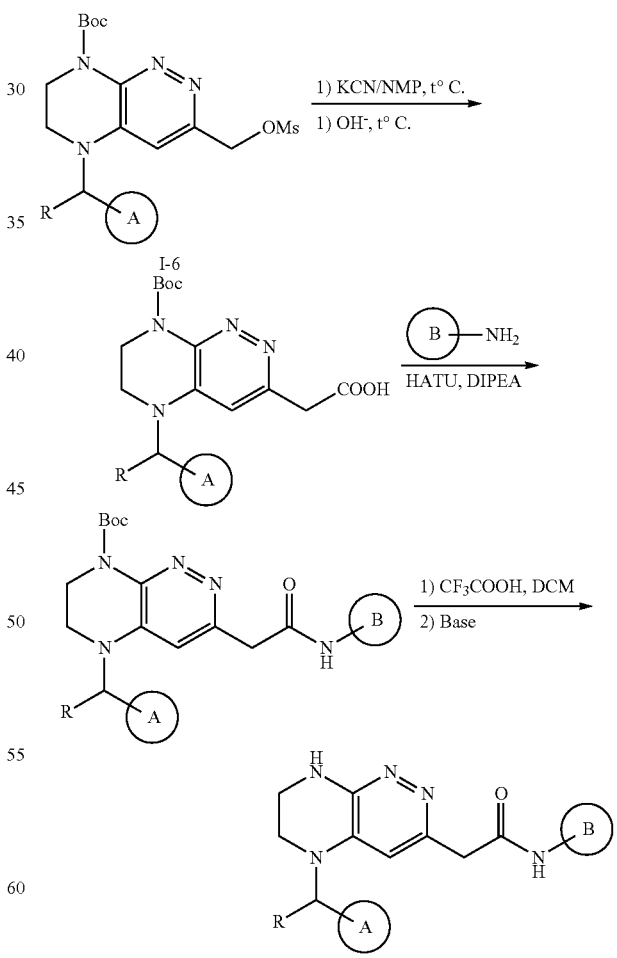

Nucleophilic substitution of the mesylate I-6 under the action of potassium cyanide and hydrolysis of the resulting nitrile in an alkaline medium lead to arylacetic acid. Acylation of the resulting amine of the obtained arylacetic acid and removal of the protective group lead to obtaining target compound.

4.12. The compounds of formula I, in which the cycle A is as defined in p. 1.1 of the description of the invention, substituent R is —H, —CH$_3$, L$^B$ represents —NHC$_{0-3}$-alkyl, cycle B is as defined in p. 1.1 of the description of the invention, may be synthesized under Scheme XII.

Scheme XII

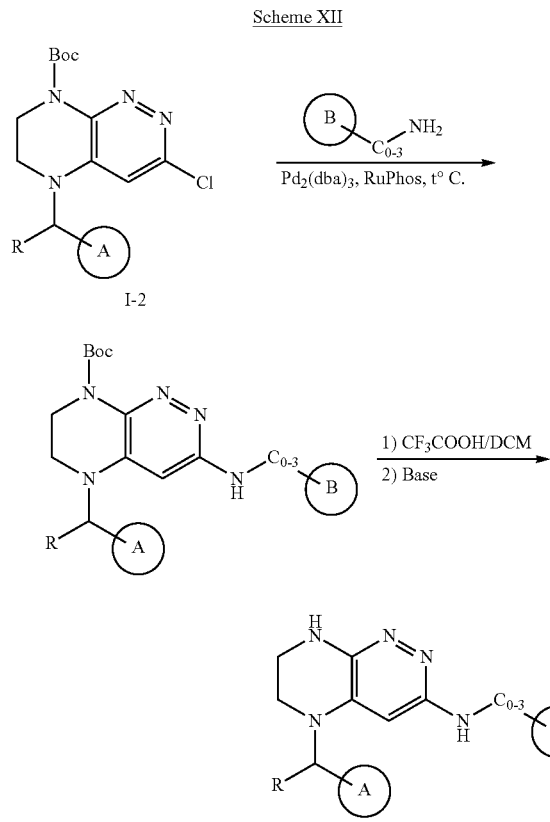

Palladium-catalyzed substitution of the chlorine atom of compound I-2 to amino group under the action of corresponding amino compound and subsequent removal of the protective group lead to obtaining target compound.

4.13. The compounds of formula I, in which the cycle A is as defined in p. 1.1 of the description of the invention, substituent R is —H, —CH$_3$, L$^B$ represents —C(O)C$_{0-3}$-alkyl, cycle B is as defined in p. 1.1 of the description of the invention, may be synthesized under Scheme XIII.

Scheme XIII

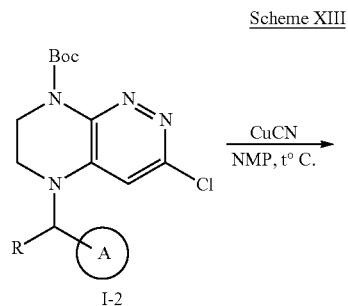

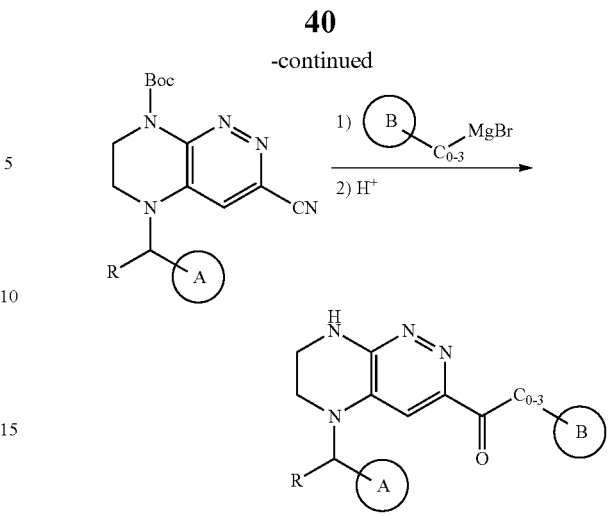

The first stage includes the substitution of chlorine atom to cyano group under the action of copper cyanide (I). Exposure of the obtained nitrile to the respective organomagnesium compound leads to obtaining target compound.

All the compounds of the present invention can be obtained based on the above-indicated synthetic approaches, examples of experimental methodologies and well-known techniques and materials.

5. USES, FORMULATIONS, ADMINISTRATION

5.1. Pharmaceutical Uses; Indications

The compounds, described in the present invention, may be used for the treatment of diseases, the pathogenesis of which involves protein kinases. In particular, the compounds described in the present invention are capable of inhibiting tyrosine kinases ALK, ROS1, MET, EGFR, which are involved in growth, development and metastasis of cancers. In addition, it is shown that a number of the compounds, constituting the present invention, possess anti-proliferative activity in vitro towards cancer cell lines, such as, for example, Karpas-299, SU-DHL-1, NCI-H3122 or NCI-H2228. Such compounds are of interest for the treatment of various types of cancer, including both solid tumors and lymphomas, particularly for the treatment of cancers resistant to other modes of treatment.

The types of cancer, for the treatment of which compounds of this invention can be used, include solid tumors (e.g., cancer of prostate, colon, pancreas, ovarian, breast, esophageal, non-small cell lung cancer (NSCLC), tumor diseases of the brain, including glioblastoma and neuroblastoma, cancer of soft tissues, including rhabdomyosarcoma, etc.), various forms of lymphoma such as non-Hodgkin's lymphoma (NHL) known as anaplastic large cell lymphoma (ALCL), various forms of leukemia and other forms of cancer, pathogenesis of which is associated with activity of ALK, MET, EGFR, ROS1.

Since aberrant ALK-kinase activity is a cause of many oncological diseases, we assume that the use of ALK inhibitor as a drug for monotherapy or in combination with current chemotherapy agents against NSCLC, ALCL and other cancers listed above, will allow to achieve their substantial and long-term remission; ALK inhibitor can also be used as a means of the maintenance therapy intended to prevent possible relapses in patients being in need of such treatment.

5.2. Pharmaceutical Methods

Subject of the present invention also includes administecycle A therapeutically effective amount of a compound of general formula I to a subject being in need of appropriate treatment.

A "therapeutically effective amount" refers to that amount of the compound required for detectable killing of cancer cells or inhibiting their growth or propagation speed through the body, the size or number of tumors, or other characteristics of cancer. The exact required amount may vary from subject to subject, depending on the type, age, and general condition of the patient, the severity of the disease, the characteristics of the anticancer agent, drug administration methods, the combined treatment with other drugs, etc.

The substance or pharmaceutical formulation comprising the compound can be administered to the patient in any amount and by any route of administration effective for killing cancer cells or inhibiting their growth.

Single doses of anti-cancer compounds of the invention are preferably formulated in a form suitable for administration to a patient. The term "dosage unit form" means in terms of the present invention an amount of an antitumor agent suitable for the patient treatment. Under current practice, the total daily dose of the compounds and formulations described in the present invention, is prescribed by the attending physician based on a thorough medical report. The specific therapeutically effective dose level for any particular patient or organism will depend upon a number of factors, including the type of disorder, severity of the disease, the activity of the particular medicinal product, peculiarities of a pharmaceutical formulation, the age, body weight, general medical condition, sex and diet of the patient, the method and schedule of administration, the rate of metabolism and/or excretion of the compound, the duration of treatment, medicinal products used in combination or in conjunction with administering the compounds of the invention and the like factors well known in medicine.

Having mixed the medicinal product with a particular suitable pharmaceutically acceptable carrier in a desired dosage, the formulation being the essence of the invention can be administered to humans or other animals orally, rectally, parenterally, intracisternally, intravaginally, intraperitoneally, locally (via skin patches, powders, ointments or drops), sublingually, buccally, as a spray for the nose or mouth, etc.

Effective systemic dosage of the compound administered once or in the form of several individual doses, is usually in the range of 0.01 to 500 mg of the compound per kg of patient body weight, preferably from 0.1 to 125 mg/kg. Typically, the compound is administered to a patient in need of such treatment in a daily dose of about 50-2000 mg per patient. Administration can be carried out one time or several times a day, a week (or in other time interval), or from time to time. For example, the compound may be administered to a patient once or several times a day on a weekly basis (for example, every Monday) for an indefinite time or for several weeks (for example 4-10 weeks). In addition, the compound may be administered to a patient daily over a definite period of days (e.g. 2-10 days), followed by a period without substance administration (e.g. 1-30 days). This cycle can be repeated indefinitely or for a predetermined number of cycles, e.g. 4-10 cycles. As an example, the compound of the present invention may be administered to a patient daily for 5 days, followed by a break for 9 days, and so on, repeating the cycle an indefinite number of times or during 4-10 cycles.

The amount of compound which will be effective in the treatment and prevention of a particular disorder or condition will depend in particular on well known factors that influence the effective dosage of medicinal products. Furthermore, measurements in vitro or in vivo can be used optionally to determine the optimal dose range. Rough mode of determining the effective dose includes the curves extrapolation of dose-response, which will depend on the model of in vitro testing or on animals. The precise dosage level is determined by the attending physician, depending on well known factors, including route of administration, and the age, body weight, sex and general medical condition of the patient; the nature, severity and clinical status of the disease; the use (or non-use) of concomitant therapy; as well as the nature and extent of genetic changes in the cells of a patient.

When administered for the treatment and suppression of a particular disease or disorder state, the effective dosage of the compound of this invention may vary depending on the particular applied compound, the route of administration of the drug in the body, the terms and the severity of such administration; disease status, as well as a different number of physical factors related to the patient, undergoing treatment. In most cases, a satisfactory result can be achieved by administecycle A compound in a daily dosage from about 0.01 mg/kg to 500 mg/kg, typically between 0.1 and 125 mg/kg to the patient. Estimated daily dosage may be expected to vary depending on the mode of administration to the patient. Thus, the level of dosage in case of parenteral administration often ranges from 10 to 20% of the oral dosage level.

In the case when the compound of the present invention is used as part of a combination therapy regimen, the dose of each component of the combination therapy is administered ducycle A required treatment period. Compounds, forming a part of the combination therapy, may be administered to a patient both simultaneously in the dosage form, containing all components, and in the form of individual doses of the components; in addition, the compounds of the combination may be administered to the patient at different times during the treatment period, or one of them may be administered as a pretreatment for the other.

5.3. Regarding the Compounds

The compounds of the present invention may exist in free form during processing or, if required, in the form of a pharmaceutically acceptable salt or other derivative. As used herein, the term "pharmaceutically acceptable salt" refers to such salts, which are, within the rendered medical judgment, suitable for the use in contact with the tissues of human beings and animals without excessive toxicity, irritation, allergic response, etc., and correspond to a reasonable benefit and risk ratio. Pharmaceutically acceptable salts of amines, carboxylic acids, phosphonates and other types of compounds are well known in medicine. Detailed description of such salts' properties is given by Berge S. M., et al., B "Pharmaceutical Salts" J. Pharmaceutical Science, 66: 1-19 (1977), incorporated herein by reference. The salts can be prepared in situ during the isolation and purification of the compounds of the invention and may be obtained separately by reacting the free acid or free base of the compound of the invention with the appropriate base or acid, respectively. Examples of pharmaceutically acceptable, nontoxic acid salts may include salts of the amino group formed by inorganic acids such as hydrochloric, hydrobromic, phosphoric, sulfuric and perchloric acids or by organic acids such as acetic, oxalic, maleic, tartaric, succinic or malonic acids, or obtained by other methods used in the art, e.g., by ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanate, hexanate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, and the like. Typical salts of alkaline and alkaline-earth metals include sodium, lithium, potassium, calcium, magnesium and others. In addition, pharmaceutically acceptable salts may contain, if required, nontoxic cations of ammonium, quaternary ammonium and amine obtained using counterions such as halogenide, hydroxide, carboxylate, sulfate, phosphate, nitrate, lower-alkyl sulfonate and aryl sulfonate.

Furthermore, the term "pharmaceutically acceptable ester" as used herein refers to in vivo hydrolysable ester that is easily decomposed in the human body to the parent compounds or their salts. Suitable ester group includes, for example, derivatives of the pharmaceutically acceptable aliphatic carboxylic acids, particularly alkanoic, alkenoic, cycloalkanoic and alkadiene acids, in which each alkyl or alkenyl component typically has no more than 6 carbon atoms. Examples of specific esters may include derivatives of formates, acetates, propionates, butyrates, acrylates and ethylsuccinates. Obviously, the esters may also be formed by a hydroxyl group or a carboxylic acid group of the compound of the invention.

The term "pharmaceutically acceptable prodrug form" refers in the context of this invention to such prodrugs of the compounds constituting the essence of the present invention, which are suitable for the use by humans and animals without excessive toxicity, irritation, allergic response, and etc., correspond to a reasonable benefits and risks ratio. The term "prodrug" means compounds that are transformed in vivo to form the parent compound of the above formula, for example, by hydrolysis in blood.

5.4. Pharmaceutical Compositions

The invention also relates to pharmaceutical formulations which comprise at least one of the compounds described herein (or a prodrug, pharmaceutically acceptable salt or other pharmaceutically acceptable derivative thereof) and one or more pharmaceutically acceptable carriers, diluents and/or excipients. These formulations may also contain one or more additional therapeutic agents. On the other hand, the compound of the present invention may be administered to a patient in need of appropriate therapy, in combination with one or more other therapeutic regimes (e.g., in conjunction with Crizotinib or other kinase inhibitors, interferon, bone marrow transplantation, farnesyl transferase inhibitors, bisphosphonates, thalidomide, tumor vaccines, hormone therapy, antibodies, radiation, etc.). For example, additional therapeutic agents for co-administration or inclusion in a pharmaceutical formulation with compounds of the present invention may include one or more antitumor agents.

The pharmaceutical formulations claimed in the present invention comprise the compounds of the invention together with pharmaceutically acceptable carriers that may include any solvents, diluents, dispersions or suspensions, surface-active materials, isotonic agents, thickeners and emulsifiers, preservatives, binders, lubricants, etc., suitable for the particular dosage form. Except for the cases, when conventional carriers medium is incompatible with a compound of the invention, for example, during the appearance of any adverse biological events and other adverse interactions with any other component (components) of the pharmaceutical formulation, the use of such formulations is within the scope of the present invention. Materials that can serve as pharmaceutically acceptable carriers include, but are not limited to, mono- and oligosaccharides and their derivatives; malt, gelatin; talc; excipients such as cocoa butter and suppository waxes; oils such as peanut oil, cottonseed oil, Safflower oil, sesame oil, olive oil, corn oil and soybean oil; glycols such as propylene glycol; esters such as ethyl oleate and ethyl laurate; agar; buffecycle Agents such as magnesium hydroxide and aluminum hydroxide; alginic acid; pyrogen-free water; isotonic solution, Ringer's solution; ethyl alcohol, and phosphate buffer solutions. Also, the formulations may contain other non-toxic compatible lubricants such as sodium lauryl sulfate and magnesium stearate, as well as colocycle Agents, parting liquids, film formers, sweeteners, flavocycle And perfuming agents, preservatives and antioxidants.

5.5. Pharmaceutical Formulation

The subject of the present invention refers also to pharmaceutical forms—a class of pharmaceutical compositions, the composition of which is optimized for the particular route of administration in a therapeutically effective dose. Formulations of the present invention can be introduced into the body orally, topically, rectally, intraocularly, pulmonary, e.g., in the form of an inhalation spray, or intravascularly, intranasally, intraperitoneally, subcutaneously, intramuscularly, intrasternally and by infusion techniques, in recommended doses.

The pharmaceutical form of the present invention may contain a compound of formula described herein or a pharmaceutically acceptable salt thereof, and an additional drug, for example, selected from the following: kinase inhibitor, antidepressant, antineoplastic agent, antiviral agent, anti-inflammatory agent, antifungal agent or compound against vascular hyperproliferation and any pharmaceutically acceptable carrier, adjuvant or diluent. The term "pharmaceutically acceptable carrier or adjuvant" refers to the carrier or adjuvant that may be administered to a patient together with a compound, being the essence of the present invention, and which does not destroy the pharmacological activity of this compound, and is nontoxic when administered in doses sufficient to deliver a therapeutic quantity of the compound.

Pharmaceutical forms of the present invention may comprise compositions obtained by means of the use of liposomes or microencapsulation methods, drug nanoforms preparation methods and other examples known in pharmaceutics.

5.6. Use of the Compounds in Combination Therapy

Despite the fact that the compounds of the present invention may be administered as individual active pharmaceutical agent, they can also be used in combination with one or more compounds of the invention, or one or more other agents. In case of the combined oral administration the therapeutic agents may represent different pharmaceutical forms that are administered simultaneously or sequentially at different periods, or the therapeutic agents may be combined in one pharmaceutical form.

The term "combination therapy" means sequential or simultaneous administration of all agents which somehow provide a beneficial effect of drug combination with respect to the compounds of this invention in combination with other pharmaceutical agents. Coadministration refers, in particular, to the co-delivery, e.g. in one pill, capsule, injection or other form having a fixed ratio of active substances, as well as co-delivery in multiple, separate pharmaceutical forms for each compound respectively.

Thus, administration of the compounds of the present invention may be carried out in conjunction with additional therapies known to those skilled in the prevention and treatment of tumors, including radiation therapy, the use of cytostatic and cytotoxic agents, other antineoplastic agents and agents for suppressing the symptoms or adverse events of one of the medicinal products.

If the pharmaceutical form is a fixed dose, such combination uses the compounds of the invention in the acceptable dosage range. Substances of the present invention may also be administered to the patient sequentially with other antineoplastic or cytotoxic agents, when a combination of these drugs is not possible. The invention is not limited to the sequence of administration; compounds of this invention may be administered to the patient together, before or after the administration of other antineoplastic or cytotoxic drug.

EXAMPLES

1. Preparation of 3-chloro-5-(2-chloro-3,6-difluorobenzene)-5,6,7,8-tetrahydropyrazine[2,3-c]pyridazine

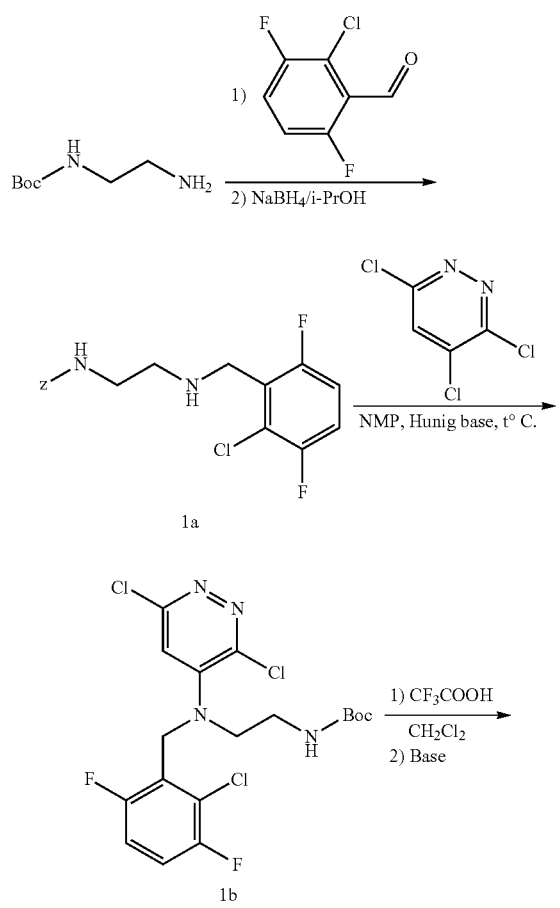

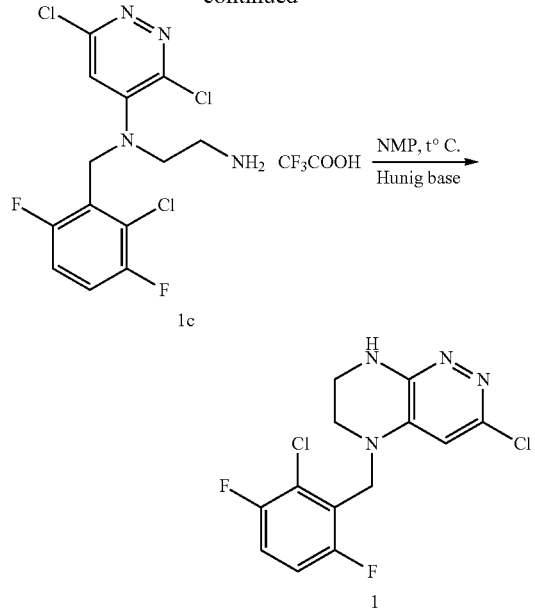

1). 17.7 g (100 mM) of 2-chloro-3,6-difluorobenzaldehyde are dissolved in 150 ml of anhydrous methanol, 0.1 ml of glacial acetic acid and 16.0 g (100 mM) of tert-butyl-2-aminoethylcarbamate are added. The reaction mixture is stirred for 4 hours at room temperature, then cooled to 0° C. and 13.3 g (350 mM) of sodium borohydride are added, maintaining the set temperature (0° C.) and left overnight at room temperature. The solvent is removed, 2.5 M of solution of sodium hydroxide (~80 mL) to pH ~10 are added to the residue and are extracted with dichloromethane (3×200 ml), the combined extracts are washed with saturated solution of $NaHCO_3$ (2×200 ml) and then with water to neutral reaction, and dried, the solvent is removed, the residue is separated by chromatography. Prepared: 24.9 g (78%) 1a.

2). The solution of 10.1 g (55 mM) 3,4,6-trichloropyridazine in 80 ml of anhydrous N-methylpyrrolidone is added 16.0 g (50 mM) of 1a and 9.6 ml (55 mM) of Hunig's base. The reaction mixture is stirred in an argon atmosphere at 70° C. for 90 hours (TLC control). N-methylpyrrolidone is removed in vacuo, the residue is dissolved in 300 ml of dichloromethane and washed with saturated solution of $NaHCO_3$ (2×150 ml), then with water to neutral reaction, dried, the solvent is removed in vacuo, the residue is recrystallized from diethyl ether. Prepared: 15.7 g (67%) 1b.

3). The solution of 9.4 g (20 mM) of 1b in 100 ml of anhydrous dichloromethane is cooled to −5° C. and is added 25 ml of 20% (v/v) solution of trifluoroacetic acid in anhydrous dichloromethane. The reaction mixture is stirred at room temperature for 18 hours, the solvents are removed, the residue is washed with anhydrous ether (3×75 ml) and dried. Prepared: 9.2 g (96%) 1c.

4). 8.7 ml (0.05 mole) of Hunig's base are added to the stirred solution of 9.6 g (20 mM) 1c in anhydrous N-methylpyrrolidone and the resulting mixture stands for 10 hours at 100° C. (TLC control), is cooled, the solvent is removed in vacuo, 200 ml of saturated solution of $NaHCO_3$ are added to the residue and the formed precipitate is filtered off, washed with water (3×50 ml), dried and separated by chromatography. Prepared: 1.7 g (25%) of compound 1, m/z=330.03.

2. Preparation of methyl 3-(3-(5-(2,6-dichloro-3-fluorobenzyl)-5,6,7,8-tetrahydropyrazine [2,3-c] pyridazine-3-yl)-1,2,4-oxadiazol-5-yl) propanoate

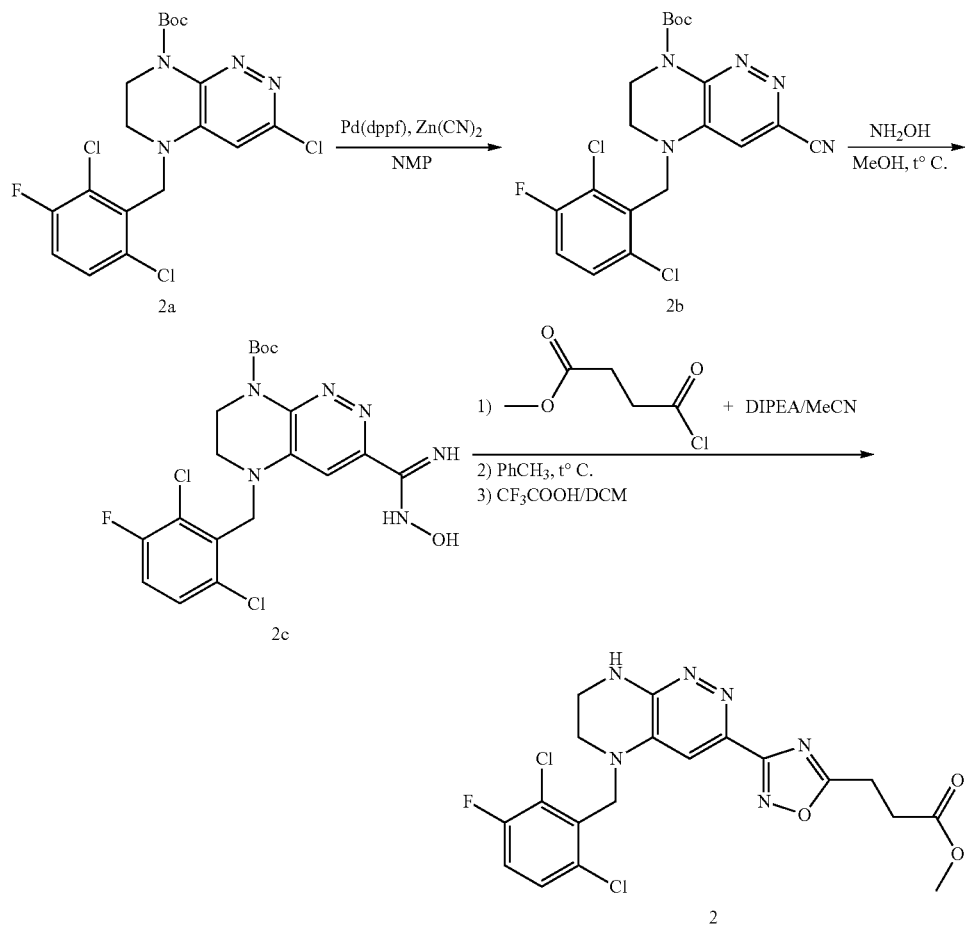

1). 1.4 g (12 mM) of zinc cyanide and 0.37 g (0.5 mM, 5 mole %) of the complex Pd (dppf) with dichloromethane are added to the solution of 4.48 g (10 mM) of 2a in 40 ml of anhydrous N-methylpyrrolidone and stirred in an argon atmosphere at 100° C. for 12 hours (TLC control). The resulting mixture is poured into 200 ml of a 1M solution of potassium cyanide. The resulting solution is extracted with dichloromethane (3×100 ml). The organic phases are combined, washed with water to the neutral reaction, dried and the solvent is removed in vacuo. The residue is separated by chromatography. Prepared 27% of 2b.

2). 2.2 g (5 mM) of 2b are dissolved in 30 ml of ethanol and 0.7 ml (10 mM) of 50% aqueous solution of hydroxylamine are added. The resulting mixture is stirred for 6 hours at 45° C. The solvent is removed. Prepared: 0.94 g (95%) of amidoxime 2c, which is used without further purification.

3). 0.94 g (2 mM) of amidoxime 2c are dissolved in 30 ml of anhydrous acetonitrile and 0.38 ml (2.2 mM) of Hunig's base and 0.31 g (2.1 mM) of the acid chloride monomethyl ester of succinic acid are added. The reaction mixture is stirred for 4 hours at room temperature, the solvent is removed, the residue is washed on the filter with water (2×5 ml), dried and added to 20 ml of toluene and refluxed for 2 hours (TLC control). Toluene is distilled, the residue is dissolved in dichloromethane (30 ml) and 1 ml of 20% trifluoroacetic acid in dichloromethane are added. The reaction mixture is allowed to stand overnight. 30 ml of a saturated solution of $NaHCO_3$ are added to the reaction mixture, washed with water to the neutral reaction and dried. The solvent is removed in vacuo, the residue is separated by chromatography. Prepared: 42% of compound 2, m/z=446.07.

3. Preparation of 5-(5-(1-(2,6-dichloro-3-fluorobenzyl)ethyl)-5,6,7,8-tetrahydropyrazine[2,3-c]pyridazine-3-yl)-3-cyclohexyl-1,2,4-oxadiazole

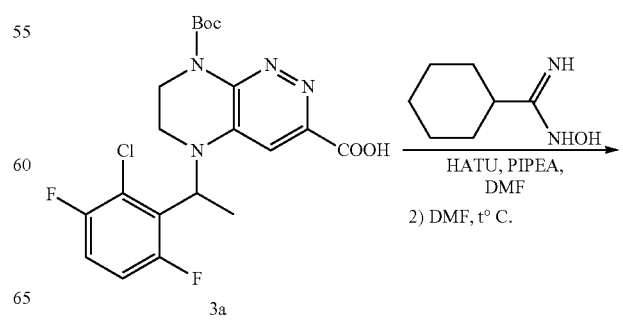

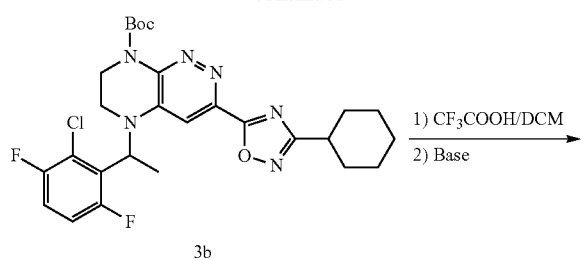

3b

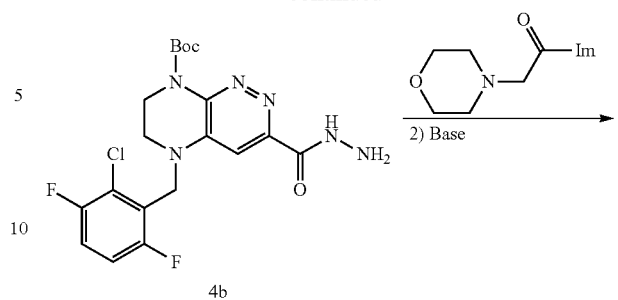

4b

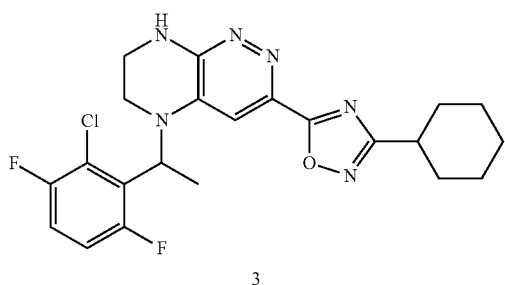

3

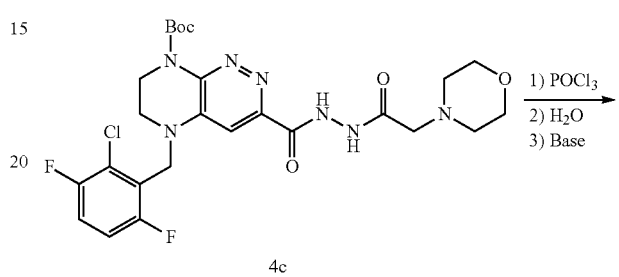

4c

1). 9 mg (20 mM) of 3a are suspended in 20 ml of acetonitrile and 3.5 g (22 mM) of carbonyldiimidazole are added and stirred for 1 hour. 3.1 g (22 mM) of cyclohexylamideoxime (prepared by standard procedure from nitrile cyclohexanecarboxylic acid) are added to the reaction mixture. The reaction mixture is stirred for 2 hours, after which the solvent is removed. 30 ml of anhydrous DMF are added to the residue and stirred in an argon atmosphere for 6 hours at 100° C. The solvent is removed in vacuo, the residue is dissolved in dichloromethane, washed with water, dried, the solvent is removed, the residue is separated by chromatography. Prepared: 42% of 3b.

2). 3.4 g (6 mM) of 3b is dissolved in 10 ml of anhydrous dichloromethane and 5 ml of a 20% solution of trifluoroacetic acid in dichloromethane are added. The reaction mixture is stirred for 8 hours, the solvent is removed, 20 ml of the saturated aqueous solution of NaHCO$_3$ are added to the residue, the precipitate formed is filtered off, washed with water and dried. Prepared: 94% of compound 3, m/z=460.16.

4. Preparation of 4-((5-(5-(2-chloro-3,6-difluorobenzyl)-5,6,7,8-tetrahydropyrazine[2,3-c]pyridazine-3-yl)-1,3,4-oxadiazole-2-yl)methyl)-morpholine

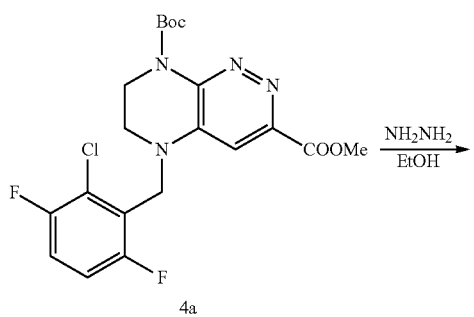

4a

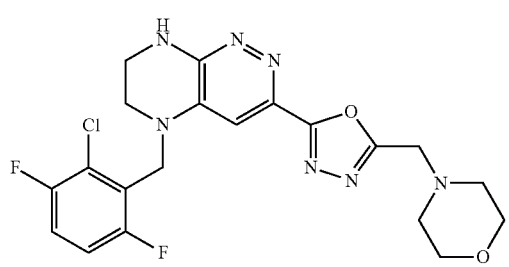

4

1). 9 g (20 mM) of 4a are dissolved in 20 ml of methanol and 2.2 ml (45 mM) of hydrazine hydrate are added. The reaction mixture is stirred for 4 hours. The solvent is removed and the residue is triturated with 5 ml of water, filtered, washed with water (2×10 ml) and dried. Prepared: 97% of 4b.

2). 8.2 g (18 mM) of 4b are dissolved in 10 ml of anhydrous acetonitrile, 2.8 ml (20 mM) of triethylamine are added and then a solution of 3.5 g (18 mM) of the imidazolide of morpholine acetic acid (prepared by the standard method of morpholine acetic acid and carbonyldiimidazole) are added dropwise in 20 ml of acetonitrile. The reaction mixture is stirred for 2 hours at room temperature. The solvent is removed and the residue is washed with water (2×5 ml), dried and used in the next stage without further purification. Prepared: 83% of 4c.

3). 7 g (12 mM) of diacyl hydrazine 4c are dissolved in 10 ml of POCl$_3$ and the reaction mixture is stirred at 50° C. for 4 hours (TLC control), cooled and poured into ice and rendered alkaline with NaHCO$_3$. The resulting mixture is extracted with dichloromethane (2×100 ml), the combined organic phases are washed with water to the neutral reaction, the solvent is removed, the residue is separated by chromatography. Prepared: 31% of compound 4, m/z=463.13.

5. Preparation of 2-(5-(5-chloro-2-methoxybenzyl)-5,6,7,8-tetrahydropyrazine[2,3-c]pyridazine-3-yl)-5-(piperidine-4-yl)-1,3,4-oxadiazole

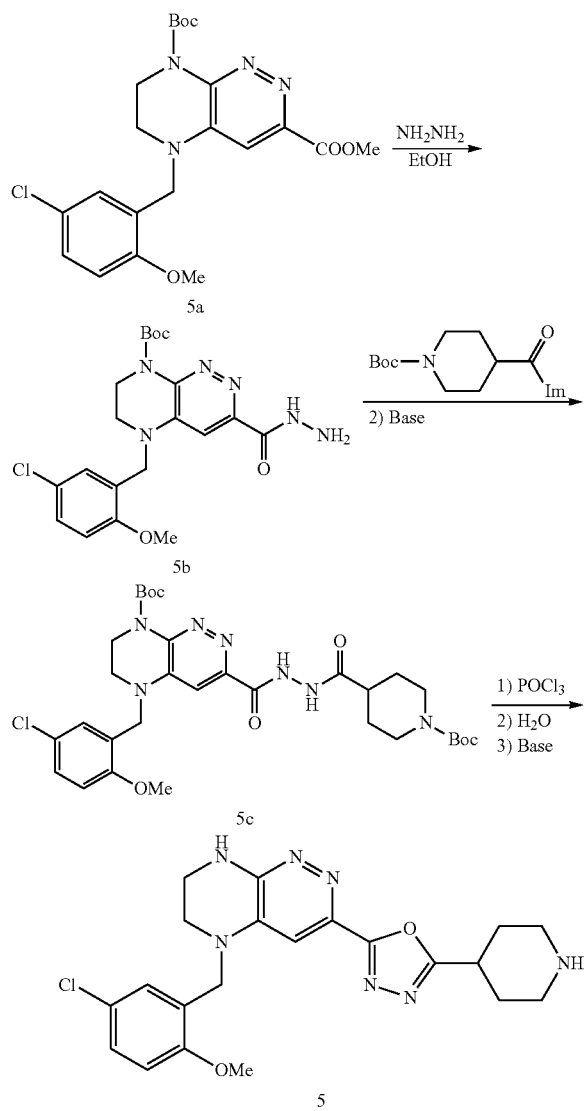

6. Preparation of 3-[5(1-methylethyl)-1,3,4-oxadiazole-2-yl]-5-[1-(2,5-dichlorophenyl)ethyl]-5,6,7,8-tetrahydropyrazine[2,3-c]pyridazine

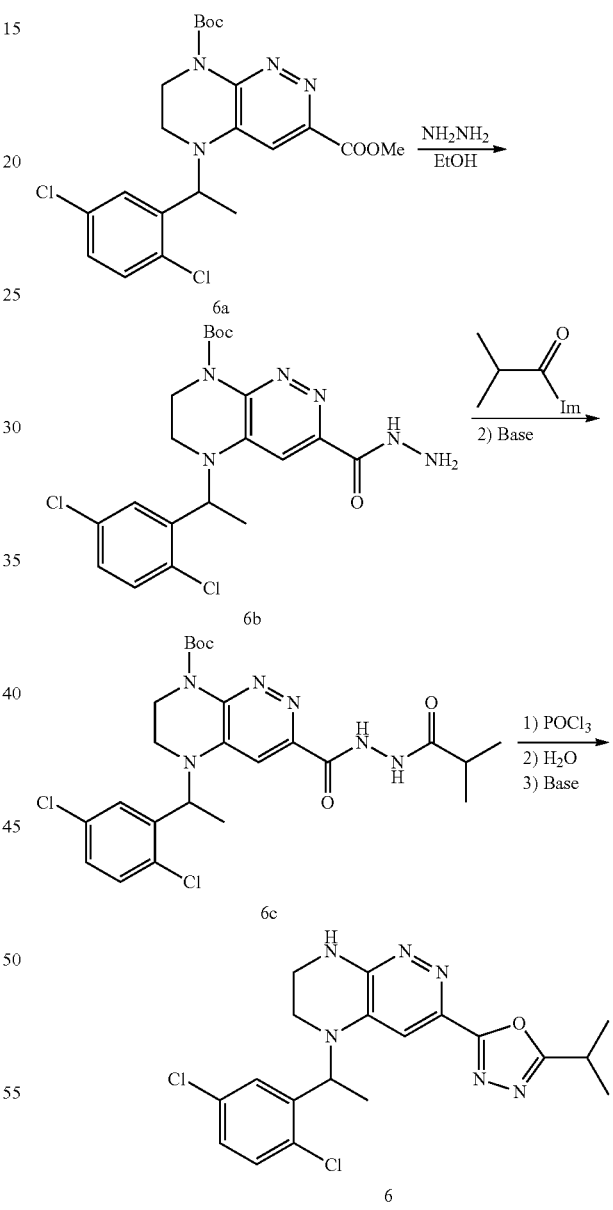

1). 9 g (20 mM) of 5a are dissolved in 20 ml of methanol and 2.2 ml (45 mM) of hydrazine hydrate are added. The reaction mixture is stirred for 4 hours. The solvent is removed and the residue is triturated with 5 ml of water, filtered, washed with water (2×10 ml) and dried. Prepared: 97% of 5b.

2). 8.1 g (18 mM) of hydrazide 5b are dissolved in 10 ml of anhydrous acetonitrile, 2.8 ml (20 mM) of triethylamine are added, then a solution of 5 g (18 mM) of imidazolide of Boc-pinicotinic acid (prepared by the standard method of pinicotinic acid and carbonyl diimidazole) is added dropwise in 20 ml of acetonitrile. The reaction mixture is stirred for 2 hours at room temperature. The solvent is removed and the residue is washed with water (2×5 ml), dried and used in the next stage without further purification. Prepared: 78% of 5c.

3). 9.9 g (15 mM) of diacyl hydrazine 5c are dissolved in 10 ml of POCl$_3$ and the reaction mixture is stirred at 50° C. for 4 hours (TLC control), cooled and poured into ice and rendered alkaline with NaHCO$_3$. The resulting mixture is extracted with dichloromethane (2×100 ml), the combined organic phases are washed with water to the neutral reaction, the solvent is removed, the residue is separated by chromatography. Prepared: 24% of compound 5, m/z=441.17.

1). 9.3 g (20 mM) of 6a are dissolved in 20 ml of methanol and 2.2 ml (45 mM) of hydrazine hydrate are added. The reaction mixture is stirred for 4 hours. The solvent is removed and the residue is triturated with 5 ml of water, filtered, washed with water (2×10 ml) and dried. Prepared: 95% of 6b.

2). 7.9 g (18 mM) of hydrazide 6b are dissolved in 10 ml of anhydrous acetonitrile, 2.8 ml (20 mM) of triethylamine are added, then a solution of 2.5 g (18 mM) of the imidazolide of isobutane acid (prepared by the standard method of isobutane acid and carbonyldiimidazole) is added dropwise in 20 ml of acetonitrile. The reaction mixture is stirred for 2 hours at room temperature. The solvent is removed and the residue is washed with water (2×5 ml), dried and used in the next stage without further purification. Prepared: 83% of 6c.

3). 8 g (15 mM) of diacyl hydrazine 6c are dissolved in 10 ml of $POCl_3$ and the reaction mixture is stirred at 50° C. for 4 hours (TLC control), cooled and poured into ice and rendered alkaline with $NaHCO_3$. The resulting mixture is extracted with dichloromethane (2×100 ml), the combined organic phases are washed with water to the neutral reaction, the solvent is removed, the residue is separated by chromatography. Prepared: 31% of compound 6, m/z=418.11.

7. Preparation of 2-(4-(5-(5-(2,6-dichloro-3-fluorobenzyl)ethyl)-5,6,7,8-tetrahydropyrazine[2,3-c]pyridazine-3-yl)-4H-1,2,4-triazole-3-yl) piperidine-1-yl) ethanol

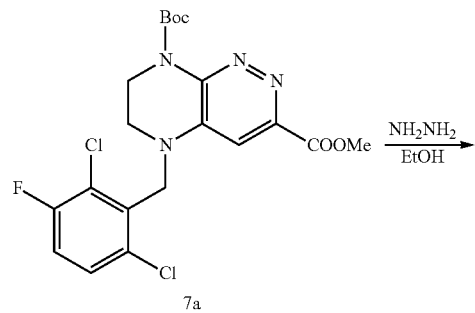

7a

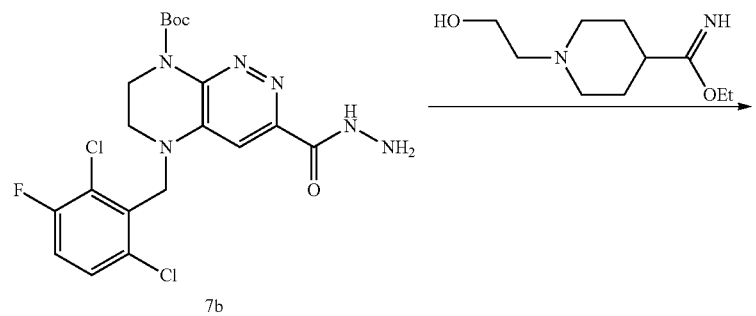

7b

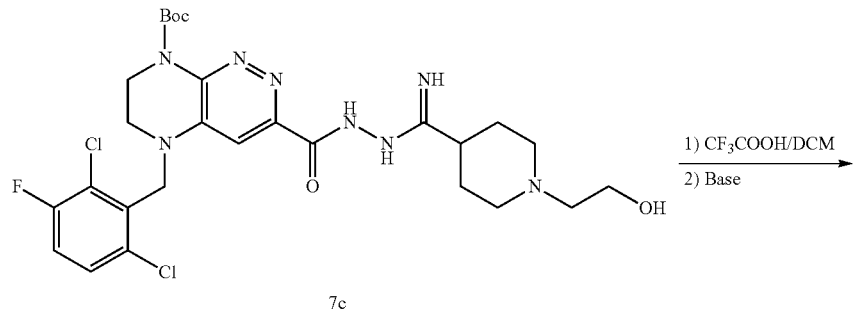

7c

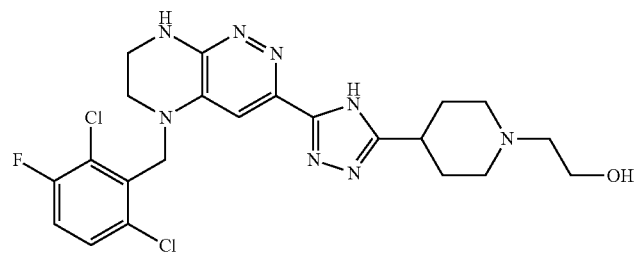

7

1). 9.4 g (20 mM) of 7a are dissolved in 20 ml of methanol and 2.2 ml (45 mM) of hydrazine hydrate are added. The reaction mixture is stirred for 4 hours. The solvent is removed and the residue is triturated with 5 ml of water, filtered, washed with water (2×10 ml) and dried. Prepared: 95% of 7b.

2). 50 ml of anhydrous ethanol are added to a solution of 2.8 g (20 mM) of 4-cyano-1-methylpiperidine in 50 ml of anhydrous diethyl ether. The reaction mixture is cooled to 0° C. and a solution of 45 mM of hydrogen chloride in 100 ml of ether is added. The reaction mixture is stirred for 8 hours, the solvent is removed, the residue is dissolved in 200 ml of anhydrous ethanol and 2.8 g (40 mM) of sodium ethoxide are added portionwise, maintaining the temperature below +10° C. The reaction mixture is stirred for 30 minutes, the precipitate is filtered off, 8.5 g (18 mM) of hydrazide 7b are added to the filtrate and stirred for 2 hours. The solvents is removed, 50 ml of anhydrous toluene are added to the residue, and the resulting mixture is refluxed for 8 hours. The solvent is removed, the residue is separated by chromatography. Prepared: 28% of 7c.

3). 20 ml of a 20% solution of trifluoroacetic acid in methylene chloride are added to a solution of 3.1 g (5 mM) of triazine 7c in 50 ml anhydrous methylene chloride. The reaction mixture is stirred for 8 hours, the solvent is removed, 20 ml of a saturated aqueous solution of NaHCO$_3$ are added to the residue. The resulting precipitate is filtered off, washed with water and dried. Prepared: 98% of compound 7, m/z=506.15.

8. Preparation of 5-(2,5-dichlorobenzyl)-3-(5-(trifluoromethyl)-4H-1,2,4-triazole-3-yl)-6,7-dihydropyrazine[2,3-c]pyridazine

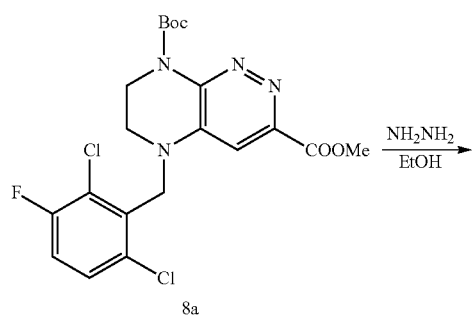

8a

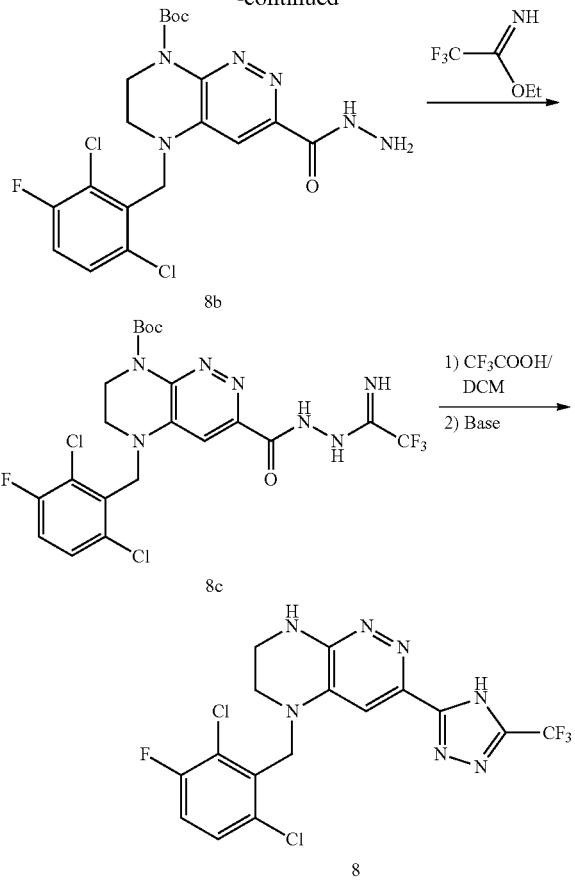

1). 9.4 g (20 mM) of 8a are dissolved in 20 ml of methanol and 2.2 ml (45 mM) of hydrazine hydrate are added. The reaction mixture is stirred for 4 hours. The solvent is removed and the residue is triturated with 5 ml of water, filtered, washed with water (2×10 ml) and dried. Prepared: 95% of 8b.

2). 8.5 g (18 mM) of hydrazide 8b are added to a solution of 2.8 g (20 mM) of trifluoroacetamide in 50 ml of anhydrous dioxane and stirred for 2 hours, then refluxed for 8 hours. The solvent is removed, the residue is separated by chromatography. Prepared: 31% of 8c.

3). 20 ml of a 20% solution of trifluoroacetic acid in methylene chloride are added to a solution of 2.8 g (5 mM) of triazine 8c in 50 ml of anhydrous methylene chloride. The reaction mixture is stirred for 8 hours, the solvent is removed, 20 ml of a saturated aqueous solution of NaHCO$_3$ are added to the residue. The resulting precipitate is filtered off, washed with water and dried. Prepared: 92% of compound 8, m/z=447.04.

9. Preparation of 3-(5-azetidine-3-ylmethyl)-4H-1,2,4-triazole-3-yl)-5-(1-(2,5-dichlorophenyl)ethyl)-6,7-dihydropyrazine[2,3-c]pyridazine

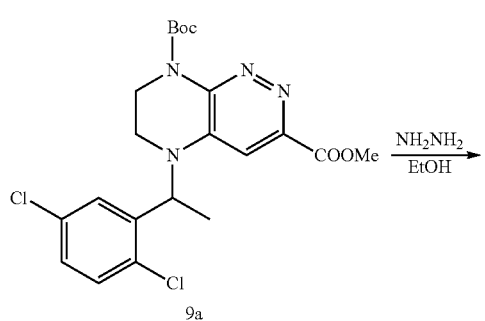

9a

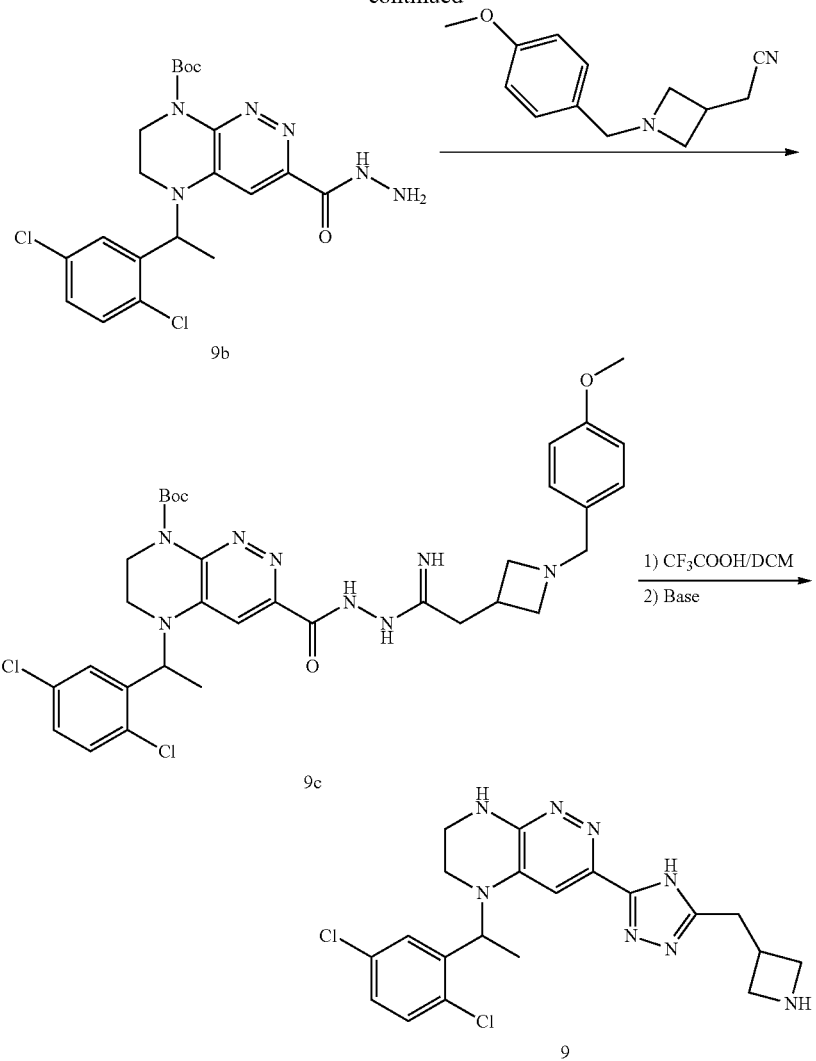

1). 9.3 g (20 mM) of 9a are dissolved in 20 ml of methanol and 2.2 ml (45 mM) of hydrazine hydrate are added. The reaction mixture is stirred for 4 hours. The solvent is removed and the residue is triturated with 5 ml of water, filtered, washed with water (2×10 ml) and dried. Prepared: 95% of 9b.

2). 40 mM of absolute ethanol are added to a solution of 4.3 g (20 mM) of 1-paramethoxybenzyl-3-cyanomethyl-azete in 100 ml of ether. The reaction mixture is cooled to 0° C. and a solution of 45 mM of hydrogen chloride in 100 ml of ether is added. The reaction mixture is stirred for 8 hours, the solvent is removed, the residue is dissolved in 200 ml of anhydrous ethanol and 2.7 g (40 mM) of sodium ethoxide are added portionwise, maintaining the temperature below +10° C. The reaction mixture is stirred for 30 minutes, the precipitate is filtered off, 8.4 g (18 mM) of hydrazide 9b, obtained in the previous stage, are added to the filtrate and stirred for 2 hours. The solvents are removed, 50 ml of anhydrous toluene are added to the residue, and the resulting mixture is refluxed for 8 hours. The solvent is removed, the residue is separated by chromatography. Prepared: 14% of 9c.

3). A solution of 1.1 g (2 mM) of triazine 9c in 20 ml of anhydrous trifluoroacetic acid is stirred for 8 hours, the solvent is removed, 10 ml of a saturated aqueous solution of NaHCO₃ are added to the residue. The resulting precipitate is filtered off, washed with water and dried. Prepared: 53% of compound 9, m/z=444.13.

10. Preparation of 5-(1-(2,6-dichloro-3-fluorophenyl)ethyl)-N-(41 pyrrolidin-1-carbonyl)phenyl)-5,6,7,8-tetrahydropyrazine[2,3-c]pyridazine-3-carboxamide

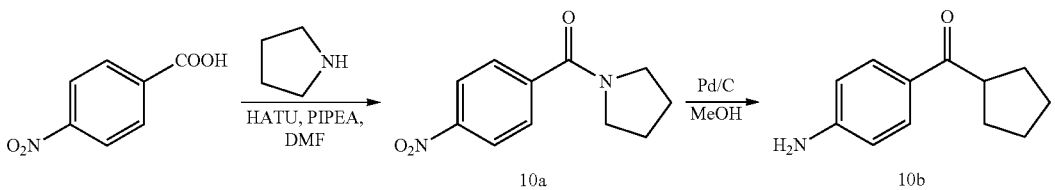

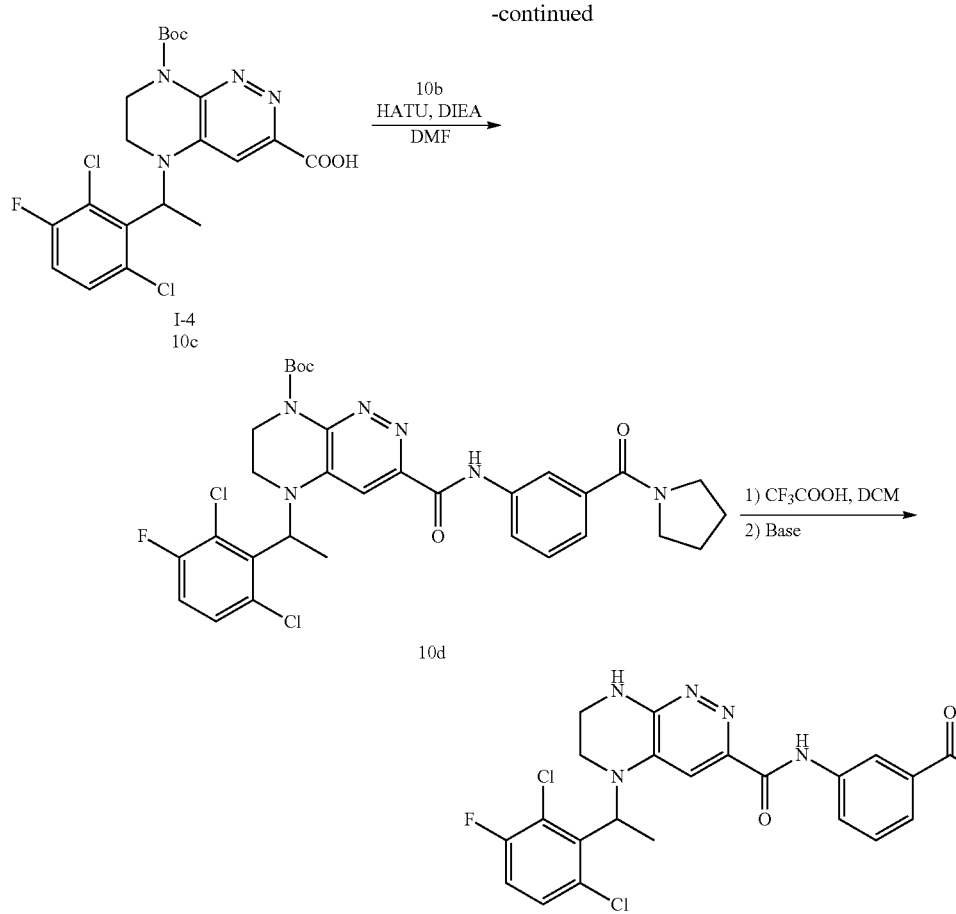

1). Pyrrolidine (320 mg, 4.5 mM) is added to a solution of 4-nitrobenzoic acid (500 mg, 3 mM), HATU (1.71 g, 4.5 mM) and Hunig's base (1.16 g, 9 mM) in DMF. The reaction mixture is stirred overnight at room temperature. The solvent is removed, the residue is separated by chromatography. Prepared: 0.52 g (79%) of 10a.

2). 10% Pd/C (200 mg) is added to a solution of 1.7 mg of 10a in methanol. The mixture is hydrogenated at room temperature for 1 hour. The reaction mixture is filtered, the solvent is removed from the filtrate. Prepared: 0.28 mg (87%) of 10b.

3). HATU (0.2 mg, 55 mM) followed by Hunig's base (95 mg 0.73 mM) are added to a solution of 10c (174 mg, 0.37 mM) in 10 ml of DMF. The mixture is stirred at room temperature for 30 minutes and 10b (104 mg, 0.55 mM) is added. The reaction mixture is stirred at room temperature for 1.5 hours. The solvent is removed, the residue is separated by chromatography. Prepared 10d (169 mg, 71%).

4). 1 ml of anhydrous trifluoroacetic acid is added to a solution of 10d (169 mg, 0.26 mM) in 3 ml of methylene chloride. The reaction mixture is stirred at room temperature for 1 hour, the solvents are removed, 10 ml of a saturated aqueous solution of $NaHCO_3$ are added to the residue to pH=9. The resulting mixture is extracted with dichloromethane (4×5 ml). The combined organic phases are dried, the solvent is removed, the residue is separated by chromatography. Prepared: 41% of compound 10 (58 mg), m/z=542.14.

11. Preparation of 5-(5-chloro-2-(trifluoromethyl) benzyl)-N-(4-(4-(dimethylamino) piperidine-1-yl)-2-methoxyphenyl)-5,6,7,8-tetrahydropyrazine [2,3-c] pyridazine-3-amine

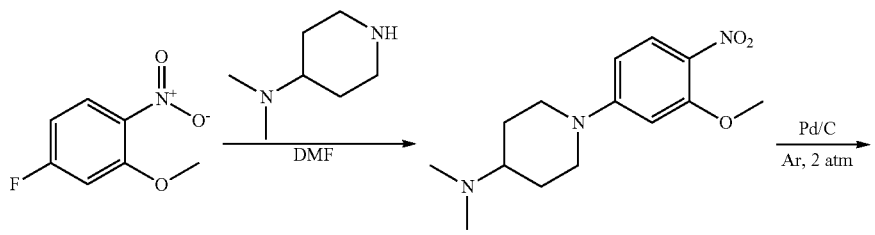

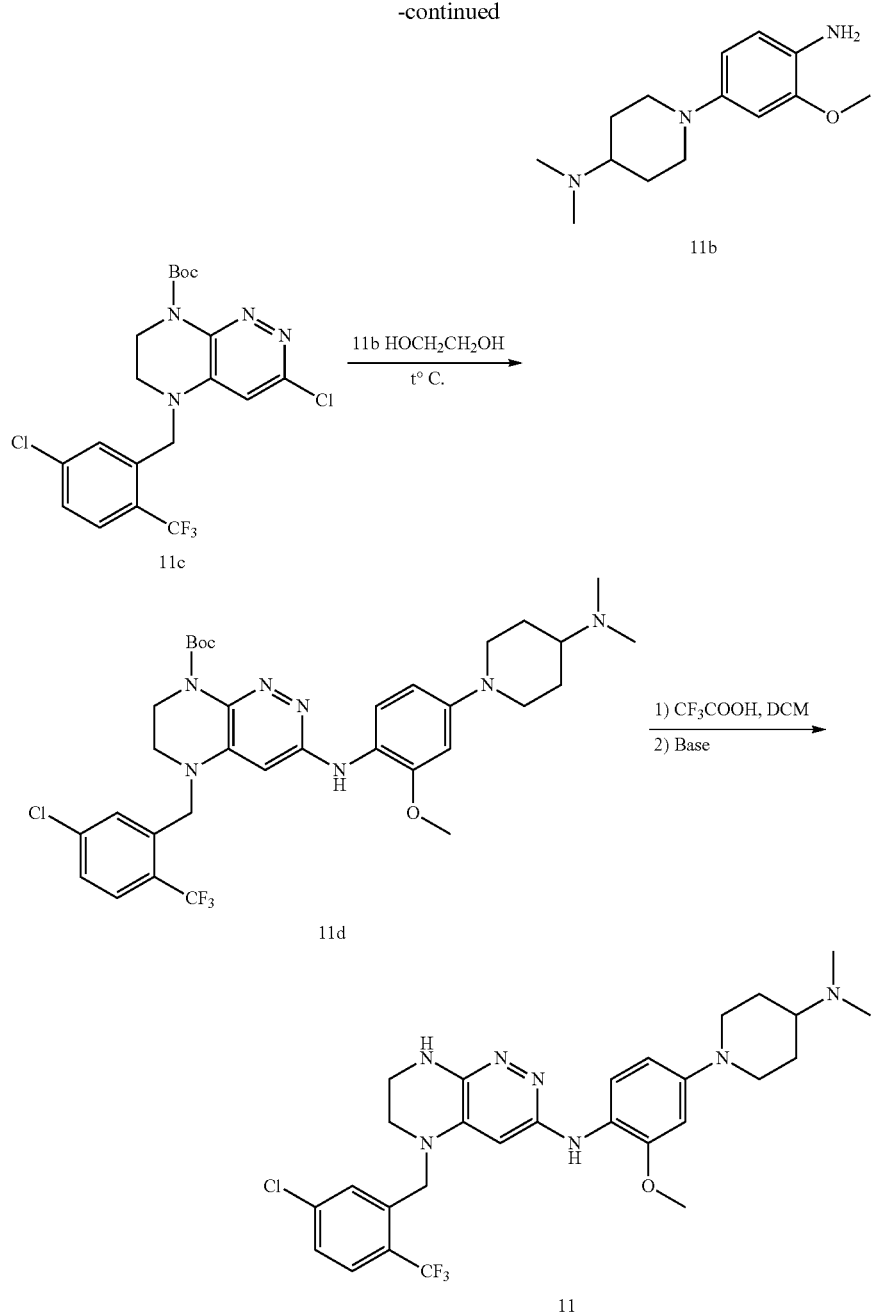

1). N,N-dimethylpiperidine-4-amine (374 mg, 2.92 mM) and K₂CO₃ (0.808 g, 5.84 mM) are added to a solution of 5-fluoro-2-nitroaniline (500 mg, 2.92 mM) in 3 ml of DMF. The reaction mixture is stirred at 120° C. for 18 hours. Saturated NaHCO₃ solution is added to the reaction mixture, the resulting mixture is extracted with ethyl acetate. The organic phase is purified by chromatography. Prepared: 88% (0.712 g) of 11a.

2). Compound 11a (250 mg, 0.9 mM) is dissolved in 10 ml of ethanol in an argon atmosphere, 10% Pd/C (0.06 g) is added. Hydrogenation is carried out for 4 hours at a pressure of 2 atmospheres. The reaction mixture is filtered through diatomite filter (Celite) and a solution of hydrogen chloride in ethanol is added. The filtrate is concentrated to prepare 11b (200 mg, 88%).

3). 40 mg (0.16 mM) of 11b are added to a solution of compound 11c (74 mg, 0.16 mM) in 1 ml of 2-methoxyethanol. The reaction mixture is stirred for 18 hours at 110° C. A saturated solution of Na₂CO₃ is added to the mixture, solution is extracted with ethyl acetate and is separated by chromatography. Prepared: 23% (25 mg) of compound 11d.

4). 1 ml of anhydrous trifluoroacetic acid is added to a solution of 11d (175 mg, 0.26 mM) in 3 ml of methylene chloride. The reaction mixture is stirred at room temperature for 1 hour, the solvents are removed, 10 ml of a saturated aqueous solution of NaHCO₃ are added to the residue to pH=9. The resulting mixture is extracted with dichloromethane (4×5 ml). The combined organic phases are dried, the solvent is removed, the residue is separated by chromatography. Prepared: 45% of compound 11 (67 mg), m/z=575.24.

12. Preparation of 5-(1-(2,6-dichloro-3-fluorophenyl)ethyl)-3-(6-(pyrrolidine-1-yl)pyridine-3-yl)-5,6,7,8-tetrahydropyrazine [2,3-c]pyridazine

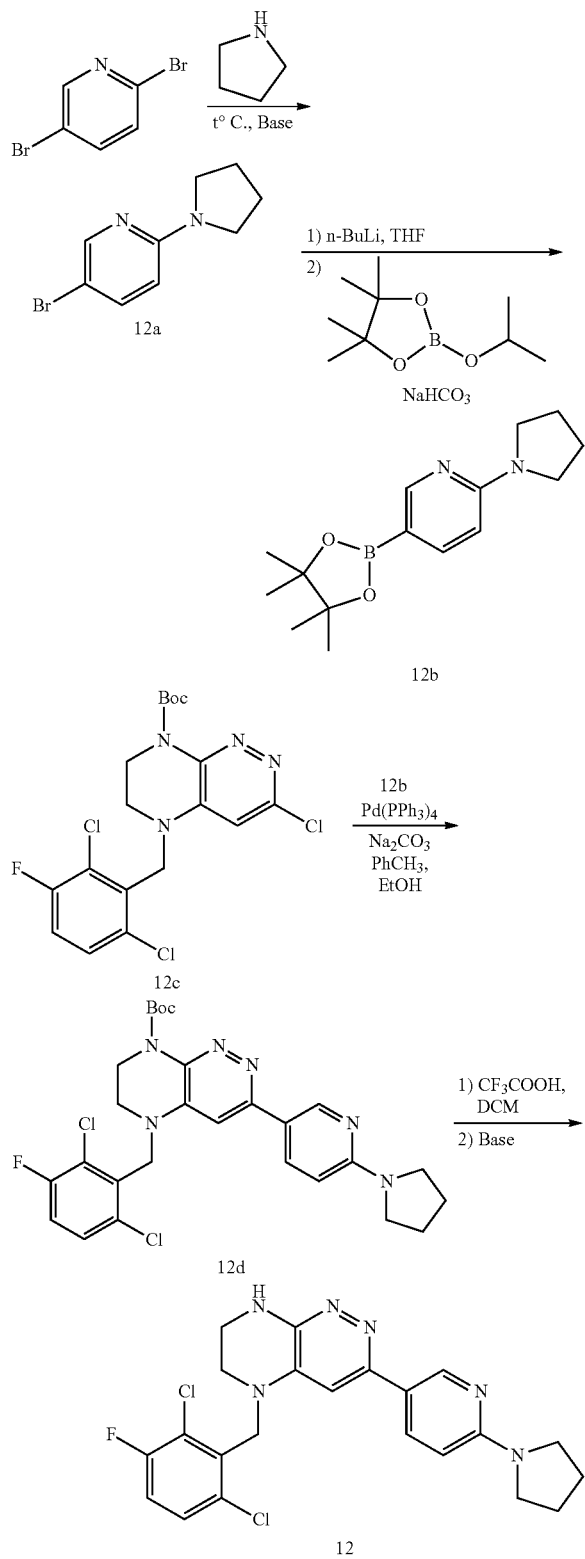

1). A mixture of 1 g (4.2 mM) of 2,5-dibromopyridine, and pyrrolidine (1.5 ml) is heated to 110° C. for 90 minutes. Excess of pyrrolidine is removed in vacuo, the residue is added to an aqueous solution of NaHCO₃. The resulting mixture is extracted with ethyl acetate. The solvent is removed to prepare: 55% (0.52 g) of 12a.

2). 0.52 g (2.3 mM) of 12a in 15 ml of THF is cooled to −78° C. and 1.7 ml of 1.6 M solution of n-butyllithium in hexane is added dropwise. The reaction mixture is stirred for 30 minutes then 2-isopropoxy-4,4,5,5-tetramethyl-1,3,2-dioxaborolane (511 mg, 2.7 mM) is added. The mixture is allowed to stand at room temperature for 2 hours. The reaction is quenched with aqueous solution of NaHCO₃. The mixture is extracted with ethyl acetate, dried using Na₂SO₄ and the solvent is removed. The resulting boronate is used in unpurified form for subsequent reactions. Prepared: 190 mg (30%) of 12b.

3). 223 mg (0.5 mM) of 12c and 165 mg (0.6 mM) of 12b are dissolved in a mixture 6:1 of toluene and ethanol. 25 mg of Pd(PPh₃)₄ and 1 ml of 2M Na₂CO₃ solution are added to the solution. The resulting mixture is heated at 80° C. for 8 hours. The reaction mixture is diluted with CH₂Cl₂, dried using MgSO₄, is filtered, concentrated and purified by gel chromatography. Prepared: 28% (78 mg) of 12c.

4). 1 ml of anhydrous trifluoroacetic acid is added to a solution of 12d (145 mg, 0.26 mM) in 3 ml of methylene chloride. The reaction mixture is stirred at room temperature for 1 hour, the solvents are removed, 10 ml of a saturated aqueous solution of NaHCO₃ are added to the residue to pH=9. The resulting mixture is extracted with dichloromethane (4×5 ml). The combined organic phases are dried, the solvent is removed, the residue is separated by chromatography. Prepared: 45% of compound 12 (54 mg), m/z=472.13.

13. Preparation of (R)-3-chloro-5-(1-(2,6-dichloro-3-fluorophenyl)ethyl)-5,6,7,8-tetrahydropyrazine [2,3-c]pyridazine

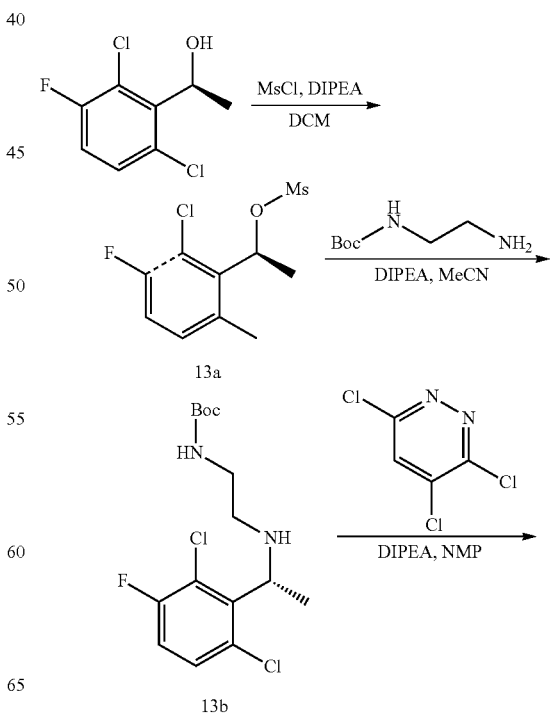

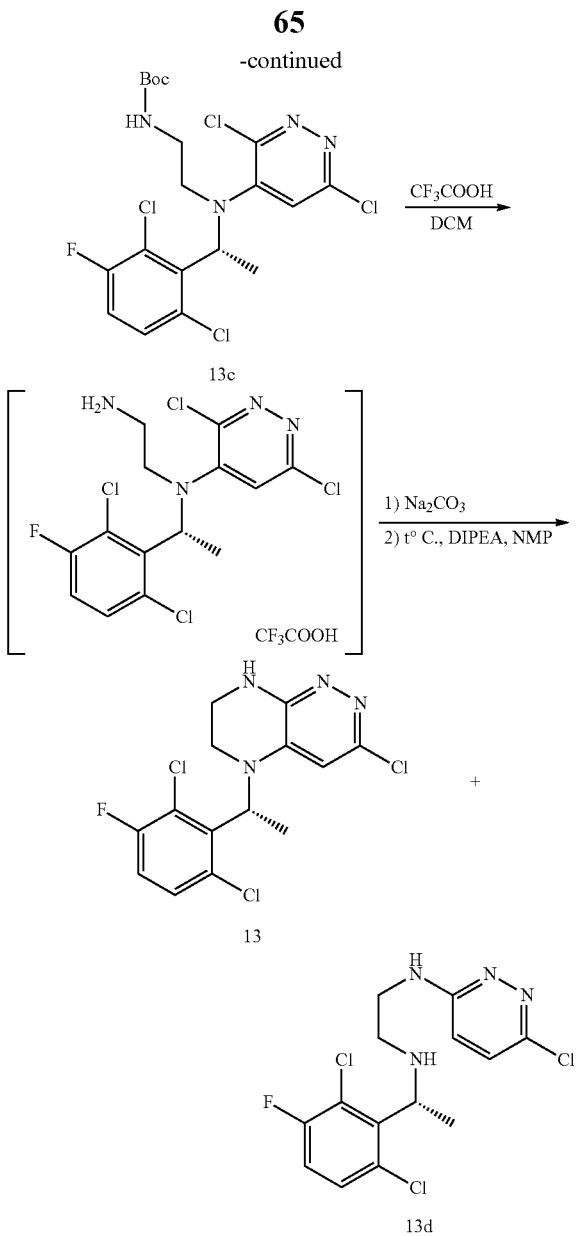

removed, the residue is dissolved in 200 ml of ether and washed with saturated NaHCO₃ (2×50 ml) and then with water to the neutral reaction. The solution is dried and the solvent is removed and the residue is dried in vacuo and separated by chromatography (CH$_2$Cl$_2$→CH$_2$Cl$_2$:MeOH (4:1)). Prepared: 4.86 (77%) of 13b.

3). 2.1 ml (0.012 mole) of N,N-diisopropylethylamine and 2.20 (0.012 mole) of 3,4,6-trichloropyridazine are added to a solution of 3.51 (0.01 mole) of 13b in 10 ml of anhydrous N-methylpyrrolidium; The reaction mixture is stirred in an argon atmosphere without moisture access at 85° C. for 200 hours (TLC control). The solvent is removed in vacuo, the residue is dissolved in 300 ml of dichloromethane and washed with saturated NaHCO₃ (1×50 ml) and then with water to the neutral reaction. The solution is dried and the solvent is removed and the residue is dried in vacuo and separated by chromatography (CH$_2$Cl$_2$→CH$_2$Cl$_2$:MeOH (4:1)). Prepared: 2.84 g (57%) of 13c.

4). 20 ml of a 20% solution of trifluoroacetic acid in dichloromethane are added to a solution of 2.50 g (5 mM) of 13c in 100 ml of dichloromethane. The reaction mixture is stirred at room temperature for 14 hours, 200 ml of dichloromethane and 150 of saturated solution of NaHCO₃ are added, the organic phase is separated, washed with water to the neutral reaction, dried and the solvent is removed, the residue is dissolved in 10 ml of anhydrous N-methylpyrrolidone, 1.2 ml (~0.07 mole) of N,N-diisopropyl-ethylamine are added and the reaction mixture is stirred in an argon atmosphere without moisture access at 100° C. for 60 hours (TLC control). The solvents are removed in vacuo, the residue is dissolved in 300 ml of dichloromethane and washed with saturated NaHCO₃ (2×100 ml) and then with water to the neutral reaction, dried, solvent is removed, the residue is dried in vacuo and separated by chromatography (hexane: ethyl acetate 1:1→CH$_2$Cl$_2$→CH$_2$Cl$_2$:MeOH (9:1)). Prepared: 415 mg (23%) of compound 13, m/z=360.01, and 418 mg of compound 13d.

14. Examples of the Synthesis of Non-Chiral 5-Substituted Derivatives of 3-Chloro-5,6,7,8-tetrahydropyrazine [2,3-c]pyridazine Non-chiral 5-substituted derivatives of 3-chloro-5,6,7,8-tetrahydropyrazine [2,3-c]pyridazine are synthesized analogously to compound 1, the synthesis method of which is described above. Examples of the prepared compounds are presented in Table.

1). 4.3 ml (~0.025 mole) N,N-diisopropylethylamine are added to a solution of 4.18 g (0.02 mole) (S)-1-(2,6-dichloro-3-fluorophenyl) ethanol in 50 ml of anhydrous dichloromethane, the mixture is cooled to −5° C. and 1.6 ml (0.021 mole) of methanesulfonyl chloride in 10 ml of anhydrous dichloromethane are added dropwise, maintaining the predetermined temperature. The reaction mixture is stirred for 2 hours at 0° C., and then another 4 hours at room temperature, then 10 ml of a saturated solution of NaHCO₃ are added to the reaction mixture, organic phase is separated and washed with water to the neutral reaction, the solution is dried and the solvent is removed. Prepared: 5.3 g (93%) of 13a, which is used in the next stage without further purification.

2). A mixture solution of 3.20 g (0.02 mole) of tert-butyl 2-aminoethylcarbamate and 3.5 ml (0.02 mole) of N, N-diisopropylethylamine in 20 ml of anhydrous acetonitrile is added to a solution of 5.17 g (0.018 mole) of 13a in 25 ml of anhydrous acetonitrile at 0° C. The reaction mixture is stirred for 18 hours at room temperature, the solvent is

| No. | Structure | m/z |
|---|---|---|
| 14 | 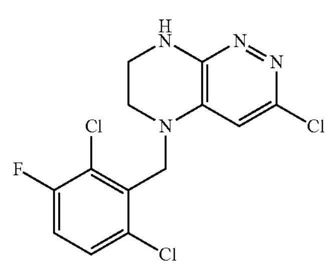 [SMILES: Fc1ccc(Cl)c(CN2CCNc3nnc(Cl)cc32)c1Cl] | 346 |

| No. | Structure | m/z |
|---|---|---|
| 15 | 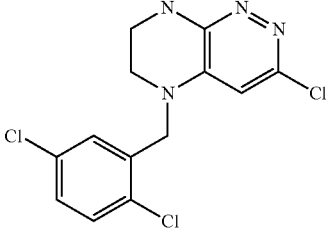 | 328 |
| 16 | 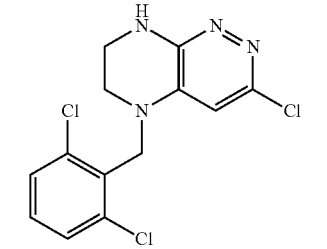 [SMILES: Clc1cc2c(nn1)NCCN2Cc1c(Cl)cccc1Cl] | 328 |
| 17 | 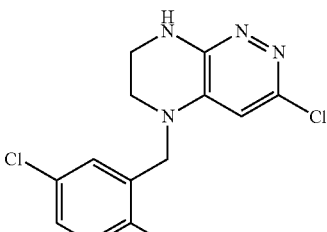 | 362 |
| 18 | 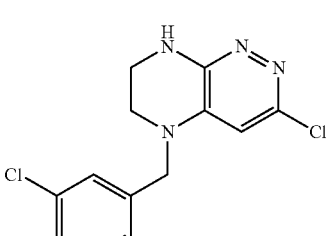 | 324.05 |
| 19 | 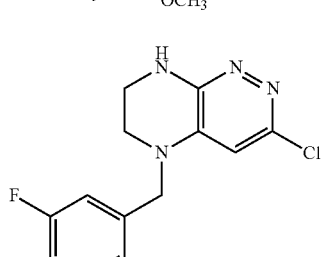 | 346.06 |
| 20 | 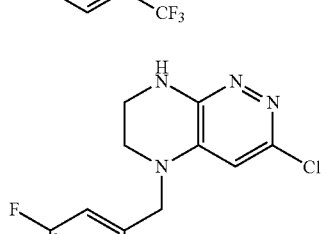 | 308.08 |
| 21 | 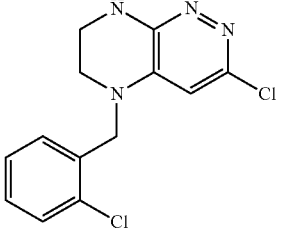 | 294.04 |

15. Examples of the Synthesis of Mixture of Chiral Enantiomers of of 5-Substituted Derivatives of 3-Chloro-5,6,7,8-Tetrahydropyrazine[2,3-c] Pyridazine A mixture of chiral enantiomers of 5-substituted derivatives of 3-chloro-5,6,7,8-tetrahydropyrazine [2,3-c] pyridazine is synthesized analogously to compound 1, the synthesis method of which is described above. Examples of the prepared compounds are presented in Table.

| No. | Structure | m/z |
|---|---|---|
| 22 | 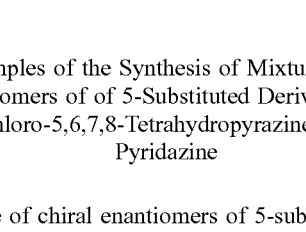 | 360.01 |
| 23 | 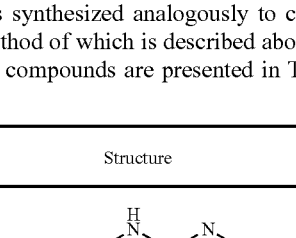 | 342.02 |
| 24 | 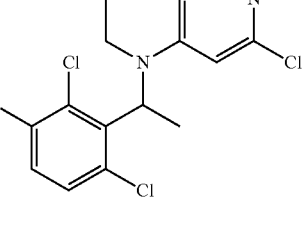 | 342.02 |

-continued

| No. | Structure | m/z |
|---|---|---|
| 25 | 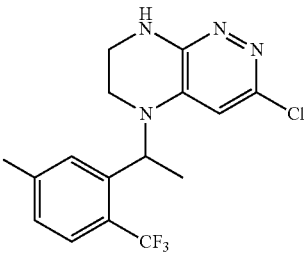 | 376.05 |
| 26 | 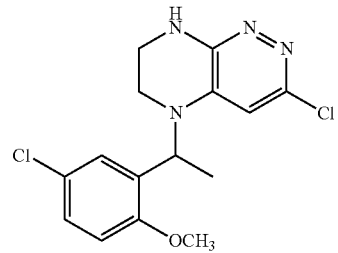 [SMILES: COc1ccc(Cl)cc1C(C)N1CCNc2nnc(Cl)cc21] | 338.07 |
| 27 | 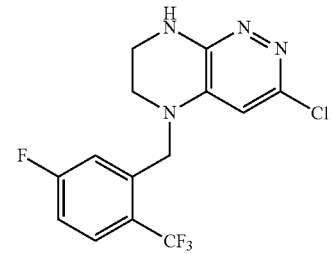 [SMILES: Fc1ccc(C(F)(F)F)c(CN2CCNc3nnc(Cl)cc32)c1] | 346.06 |
| 28 | 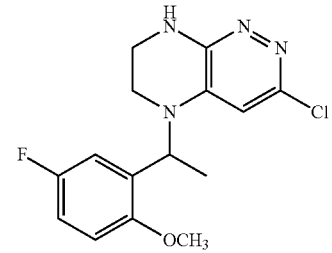 | 322.10 |
| 29 | 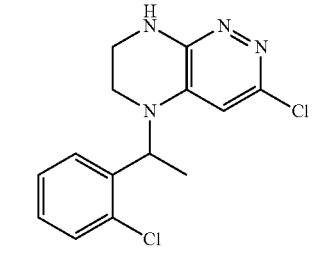 [SMILES: CC(c1ccccc1Cl)N1CCNc2nnc(Cl)cc21] | 308.06 |

| No. | Structure | m/z |
|---|---|---|
| 30 | 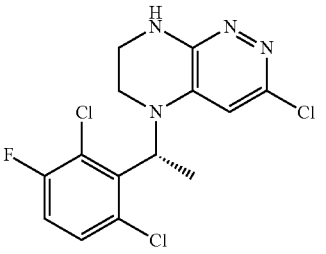 [SMILES: C[C@H](c1c(Cl)ccc(F)c1Cl)N1CCNc2nnc(Cl)cc21] | 360.01 |
| 31 | 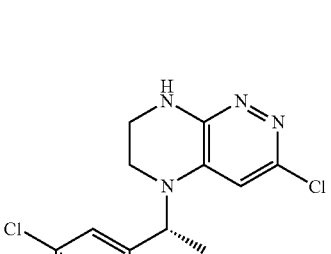 | 342.02 |
| 32 | 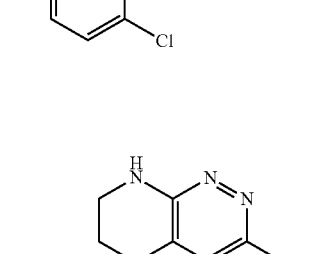 | 342.02 |
| 33 | 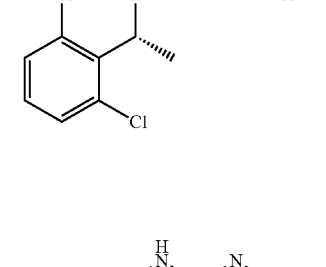 | 376.05 |
| 34 | 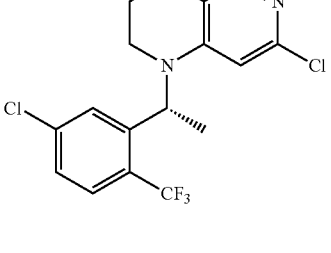 | 338.07 |

16. Examples of the Synthesis of Chiral 5-Substituted Derivatives of 3-Chloro-5,6,7,8-Tetrahydropyrazine[2,3-c]Pyridazine Chiral 5-substituted derivatives of 3-chloro-5,6,7,8-tetrahydropyrazine [2,3-c]pyridazine are synthesized analogously to compound 13, the synthesis method of which is described above. Examples of the prepared compounds are presented in Table below.

| No. | Structure | m/z |
|---|---|---|
| 35 | 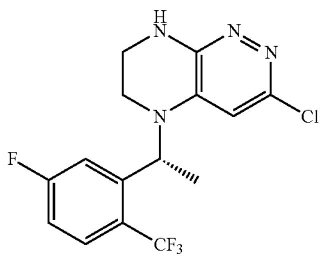 [SMILES: C[C@H](c1cc(F)ccc1C(F)(F)F)N1CCNc2nnc(Cl)cc21] | 346.06 |
| 36 | 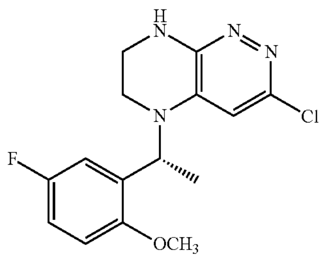 [SMILES: COc1ccc(F)cc1[C@@H](C)N1CCNc2nnc(Cl)cc21] | 322.10 |

| No. | Structure | m/z |
|---|---|---|
| 37 | 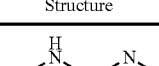 | 308.06 |

17. Examples of the Synthesis of 5-Substituted Derivatives of 3-(5-Benzyl-5,6,7,8-Tetrahydropyrazine[2,3-c]Pyridazine-3-Yl)-1,2,4-Oxadiazole 5-substituted derivatives of 3-(5-benzyl-5,6,7,8-tetrahydropyrazine [2,3-c]pyridazine-3-yl)-1,2,4-oxadiazole are synthesized from the corresponding Boc-protective 5-substituted derivatives of 3-chloro-5,6,7,8-tetrahydropyrazine [2,3-c]pyridazine analogously to compound 2, the preparation method of which is described above. Examples of the prepared compounds are presented in Table below.

| No. | Structure | m/z |
|---|---|---|
| 38 | 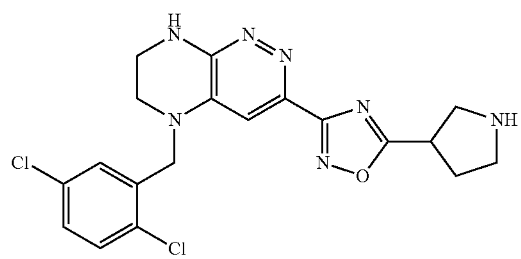 [SMILES: Clc1ccc(Cl)c(CN2CCNc3nnc(-c4noc(C5CCNC5)n4)cc32)c1] | 431.10 |
| 39 | 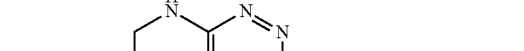 | 431.10 |
| 40 | 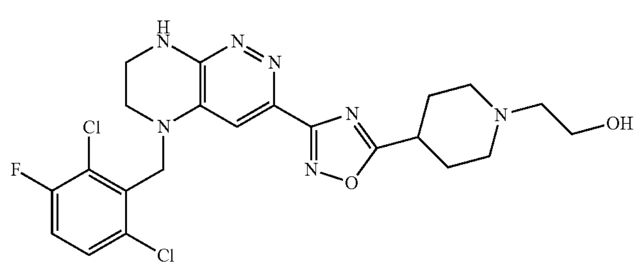 [SMILES: OCCN1CCC(c2nc(-c3cc4c(nn3)NCCN4Cc3c(Cl)ccc(F)c3Cl)no2)CC1] | 507.14 |

| No. | Structure | m/z |
|---|---|---|
| 41 | 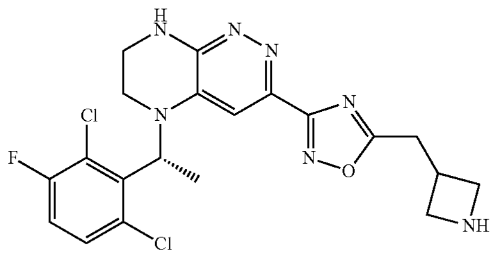 [SMILES: C[C@H](c1c(Cl)ccc(F)c1Cl)N1CCNc2nnc(-c3noc(CC4CNC4)n3)cc21] | 463.11 |
| 42 | 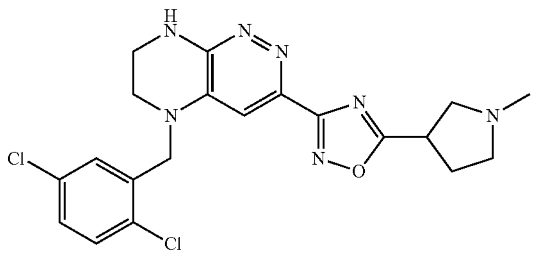 [SMILES: CN1CCC(c2nc(-c3cc4c(nn3)NCCN4Cc3cc(Cl)ccc3Cl)no2)C1] | 455.12 |
| 43 | 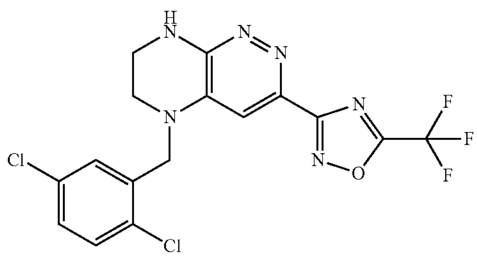 [SMILES: FC(F)(F)c1nc(-c2cc3c(nn2)NCCN3Cc2cc(Cl)ccc2Cl)no1] | 430.03 |
| 44 | 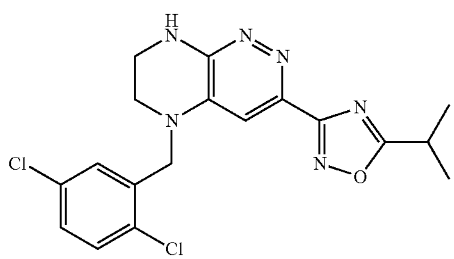 [SMILES: CC(C)c1nc(-c2cc3c(nn2)NCCN3Cc2cc(Cl)ccc2Cl)no1] | 404.09 |
| 45 | 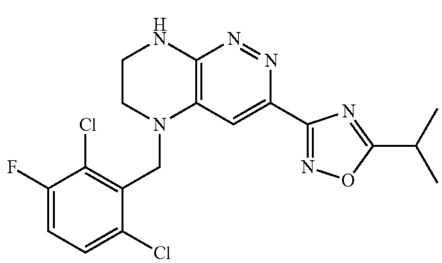 | 422.08 |
| 46 | 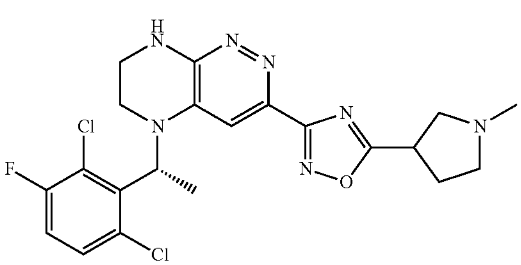 [SMILES: C[C@H](c1c(Cl)ccc(F)c1Cl)N1CCNc2nnc(-c3noc(C4CCN(C)C4)n3)cc21] | 477.12 |

| No. | Structure | m/z |
|---|---|---|
| 47 | 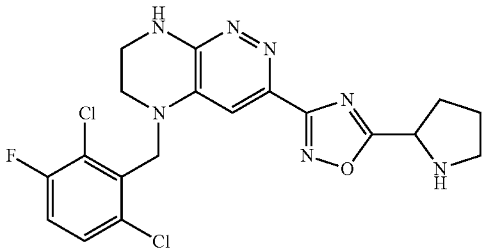 [SMILES: Fc1ccc(Cl)c(CN2CCNc3nnc(-c4noc(C5CCCN5)n4)cc32)c1Cl] | 449.09 |
| 48 | 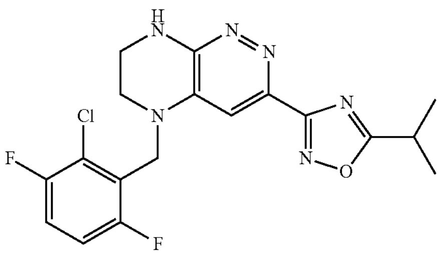 [SMILES: CC(C)c1nc(-c2cc3c(nn2)NCCN3Cc2c(F)ccc(F)c2Cl)no1] | 406.11 |
| 49 | 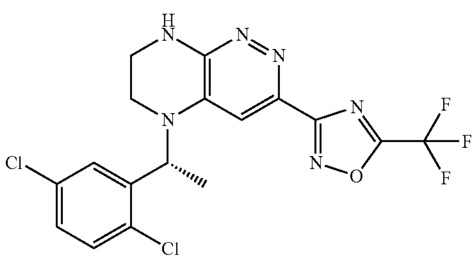 [SMILES: C[C@H](c1cc(Cl)ccc1Cl)N1CCNc2nnc(-c3noc(C(F)(F)F)n3)cc21] | 444.05 |
| 50 | 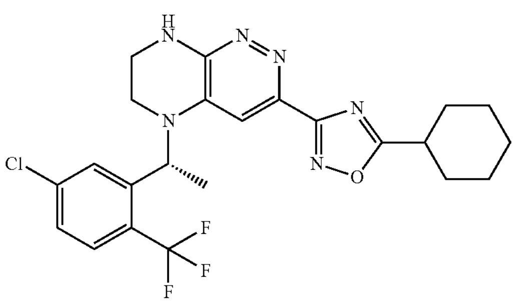 [SMILES: C[C@H](c1cc(Cl)ccc1C(F)(F)F)N1CCNc2nnc(-c3noc(C4CCCCC4)n3)cc21] | 492.17 |
| 51 | 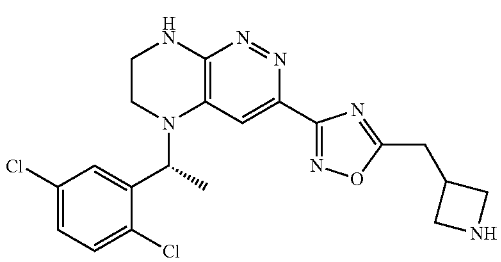 [SMILES: C[C@H](c1cc(Cl)ccc1Cl)N1CCNc2nnc(-c3noc(CC4CNC4)n3)cc21] | 445.12 |
| 52 | 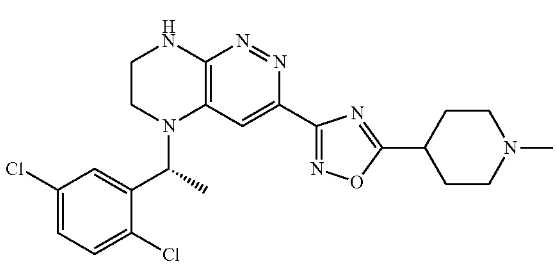 [SMILES: C[C@H](c1cc(Cl)ccc1Cl)N1CCNc2nnc(-c3noc(C4CCN(C)CC4)n3)cc21] | 473.15 |

| No. | Structure | m/z |
|---|---|---|
| 53 | 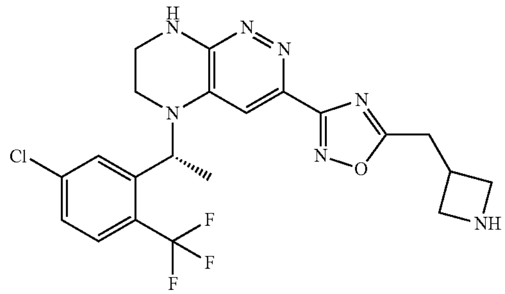 [SMILES: C[C@H](c1cc(Cl)ccc1C(F)(F)F)N1CCNc2nnc(-c3noc(CC4CNC4)n3)cc21] | 479.14 |

18. Examples of Synthesis of 5-Substituted Derivatives of 3-(5-Benzyl-5,6,7,8-Tetrahydropyrazine[2,3-c]Pyridazine-3-Yl)-1,2,4-Oxadiazole 3-substituted derivatives of 5-(5-substituted-5,6,7,8-tetrahydropyrazine [2,3-c]pyridazine-3-yl)-1,2,4-oxadiazole are synthesized from the corresponding Boc-protective 5-substituted derivatives of 3-chloro-5,6,7,8-tetrahydropyrazine [2,3-c]pyridazine analogously to compound 3, the synthesis method of which is described above. Examples of the prepared compounds are presented in Table.

| No. | Structure | m/z |
|---|---|---|
| 54 | 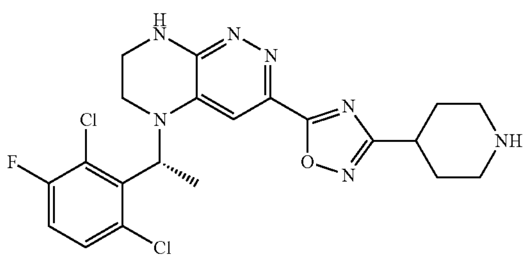 [SMILES: C[C@H](c1c(Cl)ccc(F)c1Cl)N1CCNc2nnc(-c3nc(C4CCNCC4)no3)cc21] | 477.12 |
| 55 | 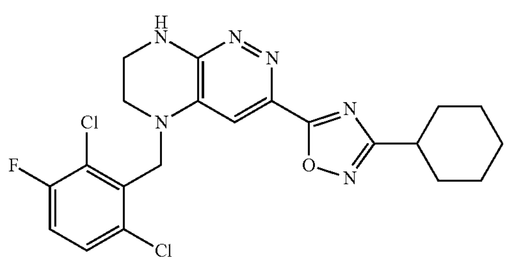 [SMILES: Fc1ccc(Cl)c(CN2CCNc3nnc(-c4nc(C5CCCCC5)no4)cc32)c1Cl] | 462.11 |
| 56 | 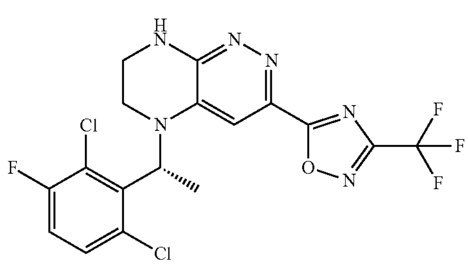 [SMILES: C[C@H](c1c(Cl)ccc(F)c1Cl)N1CCNc2nnc(-c3nc(C(F)(F)F)no3)cc21] | 462.04 |

| No. | Structure | m/z |
|---|---|---|
| 57 | 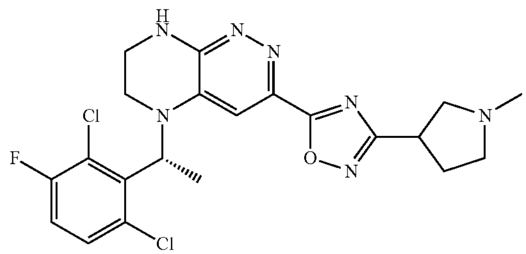 [SMILES: C[C@H](c1c(Cl)ccc(F)c1Cl)N1CCNc2nnc(-c3nc(C4CCN(C)C4)no3)cc21] | 477.12 |
| 58 | 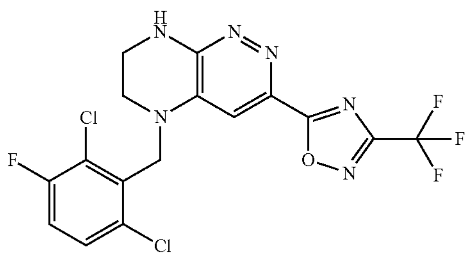 [SMILES: Fc1ccc(Cl)c(CN2CCNc3nnc(-c4nc(C(F)(F)F)no4)cc32)c1Cl] | 448.02 |
| 59 | 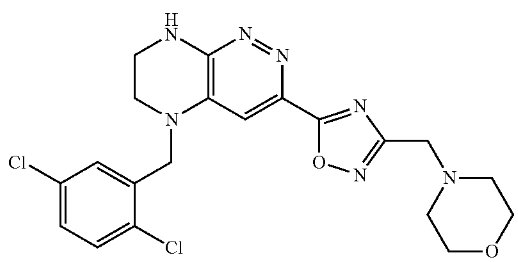 [SMILES: Clc1ccc(Cl)c(CN2CCNc3nnc(-c4nc(CN5CCOCC5)no4)cc32)c1] | 461.11 |
| 60 | 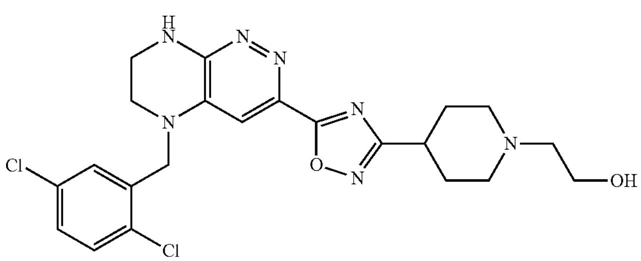 [SMILES: OCCN1CCC(c2noc(-c3cc4c(nn3)NCCN4Cc3cc(Cl)ccc3Cl)n2)CC1] | 489.14 |
| 61 | 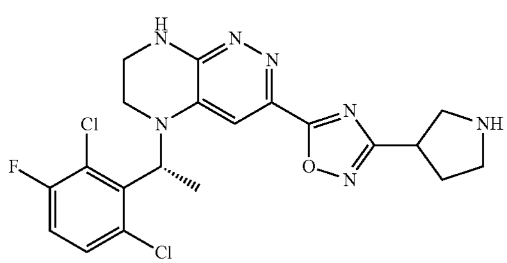 [SMILES: C[C@H](c1c(Cl)ccc(F)c1Cl)N1CCNc2nnc(-c3nc(C4CCNC4)no3)cc21] | 463.11 |
| 62 | 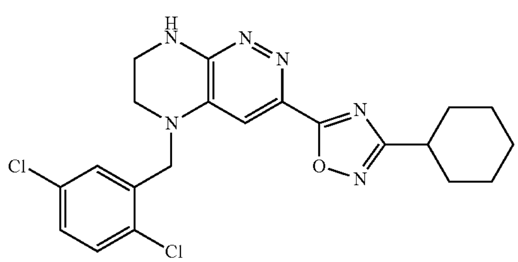 [SMILES: Clc1ccc(Cl)c(CN2CCNc3nnc(-c4nc(C5CCCCC5)no4)cc32)c1] | 444.12 |

-continued

| No. | Structure | m/z |
|---|---|---|
| 63 | 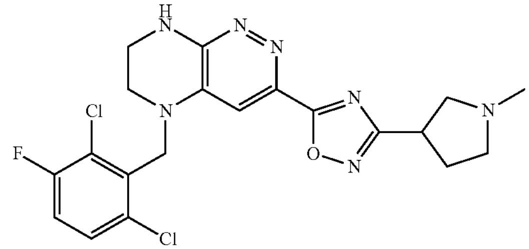 [SMILES: CN1CCC(c2noc(-c3cc4c(nn3)NCCN4Cc3c(Cl)ccc(F)c3Cl)n2)C1] | 463.11 |
| 64 | 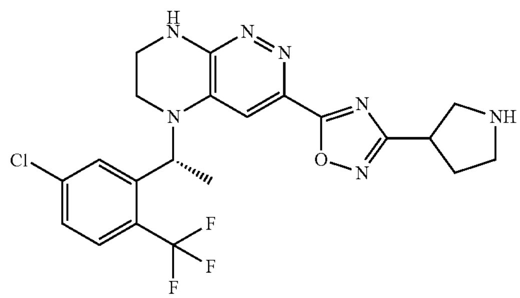 [SMILES: C[C@H](c1cc(Cl)ccc1C(F)(F)F)N1CCNc2nnc(-c3nc(C4CCNC4)no3)cc21] | 479.14 |
| 65 | 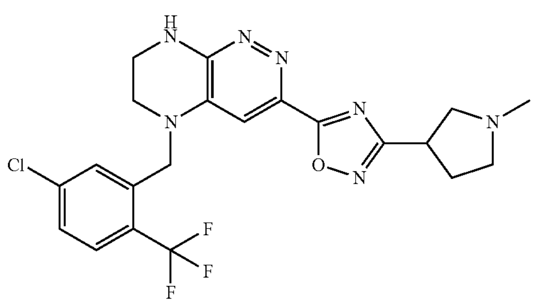 [SMILES: CN1CCC(c2noc(-c3cc4c(nn3)NCCN4Cc3cc(Cl)ccc3C(F)(F)F)n2)C1] | 479.14 |
| 66 | 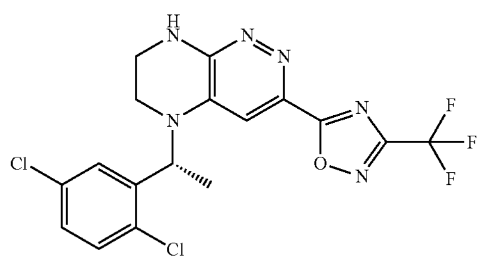 [SMILES: C[C@H](c1cc(Cl)ccc1Cl)N1CCNc2nnc(-c3nc(C(F)(F)F)no3)cc21] | 444.05 |
| 67 | 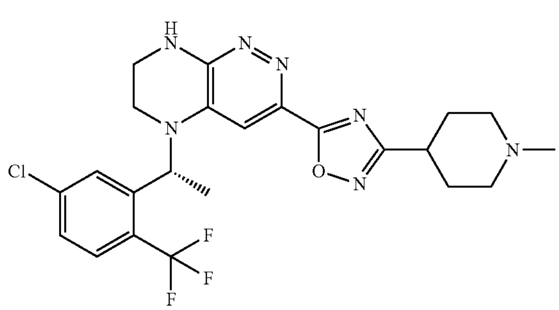 [SMILES: C[C@H](c1cc(Cl)ccc1C(F)(F)F)N1CCNc2nnc(-c3nc(C4CCN(C)CC4)no3)cc21] | 507.18 |

| No. | Structure | m/z |
|---|---|---|
| 68 | 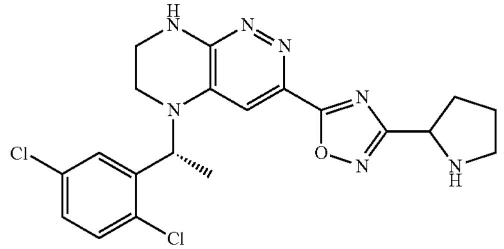 [SMILES: C[C@H](c1cc(Cl)ccc1Cl)N1CCNc2nnc(-c3nc(C4CCCN4)no3)cc21] | 445.12 |
| 69 | 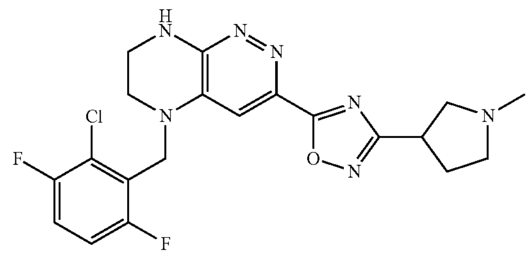 [SMILES: CN1CCC(c2noc(-c3cc4c(nn3)NCCN4Cc3c(F)ccc(F)c3Cl)n2)C1] | 447.14 |
| 70 | 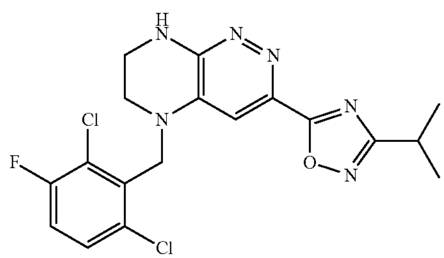 [SMILES: CC(C)c1noc(-c2cc3c(nn2)NCCN3Cc2c(Cl)ccc(F)c2Cl)n1] | 422.08 |
| 71 | 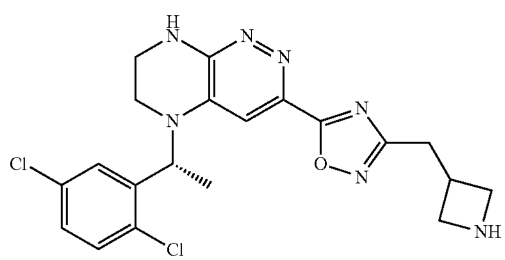 [SMILES: C[C@H](c1cc(Cl)ccc1Cl)N1CCNc2nnc(-c3nc(CC4CNC4)no3)cc21] | 445.12 |

19. Examples of Synthesis of 5-Substituted Derivatives of 2-(5-Substituted-5,6,7,8-Tetrahydropyrazine [2,3-c]Pyridazine-3-Yl)-1,3,4-Oxadiazole 2-substituted derivatives of 5-(5-substituted-5,6,7,8-tetrahydropyrazine [2,3-c]pyridazine-3-yl)-1,3,4-oxadiazole are synthesized from the corresponding Boc-protective 5-substituted derivatives of 3-chloro-5,6,7,8-tetrahydropyrazine [2,3-c]pyridazine analogously to compound 4, the synthesis method of which is described above. Examples of the prepared compounds are presented below.

| No. | Structure | m/z |
|---|---|---|
| 72 | 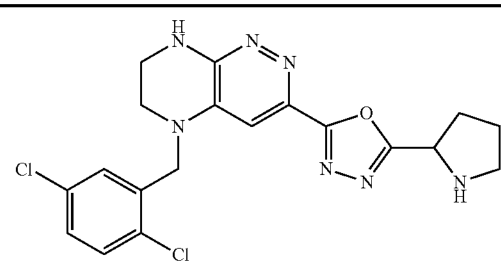 | 431.10 |

-continued

| No. | Structure | m/z |
|---|---|---|
| 73 | 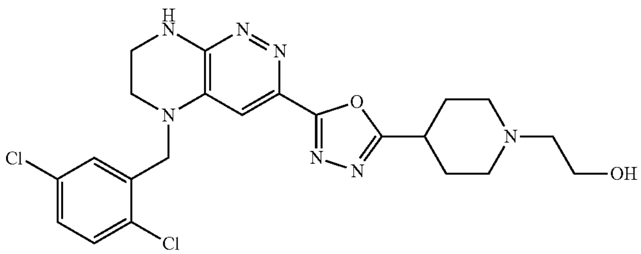 [SMILES: OCCN1CCC(c2nnc(-c3cc4c(nn3)NCCN4Cc3cc(Cl)ccc3Cl)o2)CC1] | 489.14 |
| 74 | 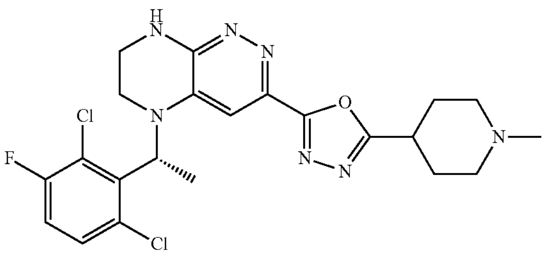 [SMILES: C[C@H](c1c(Cl)ccc(F)c1Cl)N1CCNc2nnc(-c3nnc(C4CCN(C)CC4)o3)cc21] | 491.14 |
| 75 | 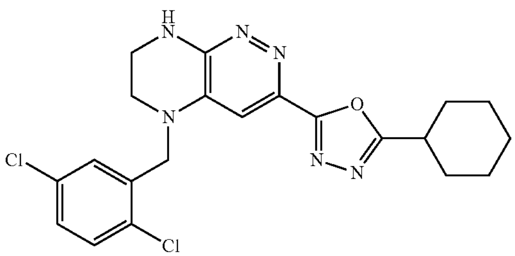 [SMILES: Clc1ccc(Cl)c(CN2CCNc3nnc(-c4nnc(C5CCCCC5)o4)cc32)c1] | 444.12 |
| 76 | 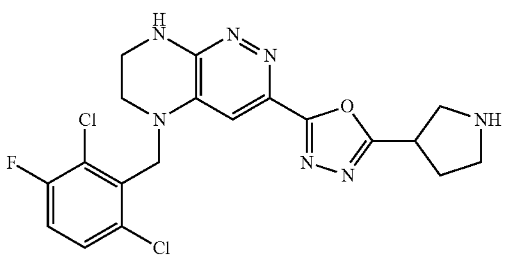 [SMILES: Fc1ccc(Cl)c(CN2CCNc3nnc(-c4nnc(C5CCNC5)o4)cc32)c1Cl] | 449.09 |
| 77 | 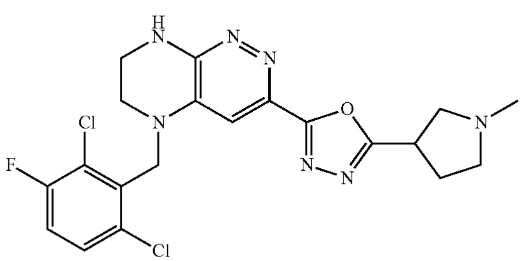 [SMILES: CN1CCC(c2nnc(-c3cc4c(nn3)NCCN4Cc3c(Cl)ccc(F)c3Cl)o2)C1] | 463.11 |
| 78 | 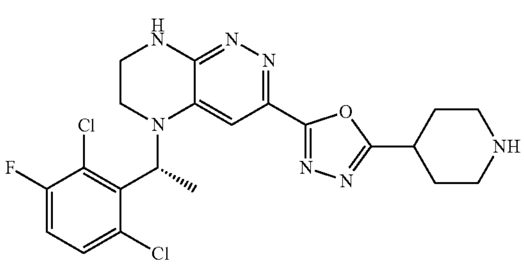 [SMILES: C[C@H](c1c(Cl)ccc(F)c1Cl)N1CCNc2nnc(-c3nnc(C4CCNCC4)o3)cc21] | 477.12 |

-continued

| No. | Structure | m/z |
|---|---|---|
| 79 | 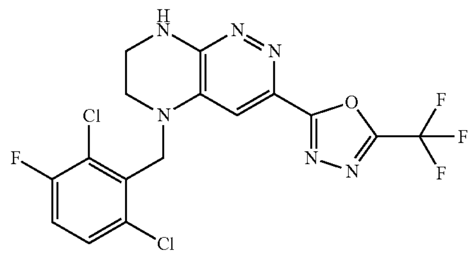 [SMILES: Fc1ccc(Cl)c(CN2CCNc3nnc(-c4nnc(C(F)(F)F)o4)cc32)c1Cl] | 448.02 |
| 80 | 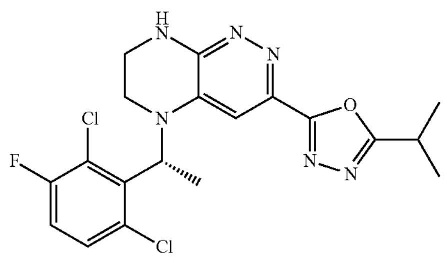 [SMILES: CC(C)c1nnc(-c2cc3c(nn2)NCCN3[C@H](C)c2c(Cl)ccc(F)c2Cl)o1] | 436.10 |
| 81 | 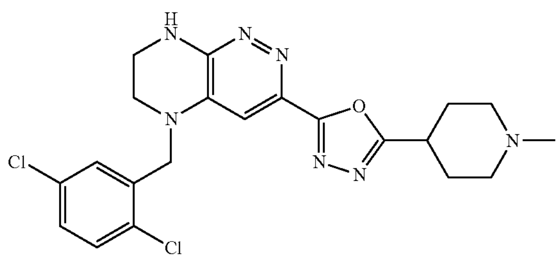 [SMILES: CN1CCC(c2nnc(-c3cc4c(nn3)NCCN4Cc3cc(Cl)ccc3Cl)o2)CC1] | 459.13 |
| 82 | 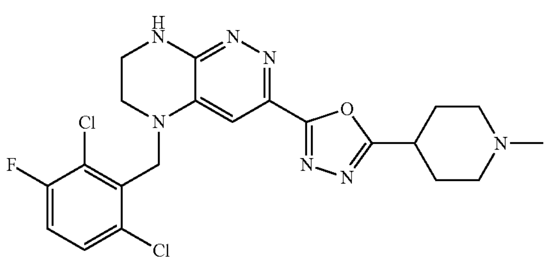 [SMILES: CN1CCC(c2nnc(-c3cc4c(nn3)NCCN4Cc3c(Cl)ccc(F)c3Cl)o2)CC1] | 477.12 |
| 83 | 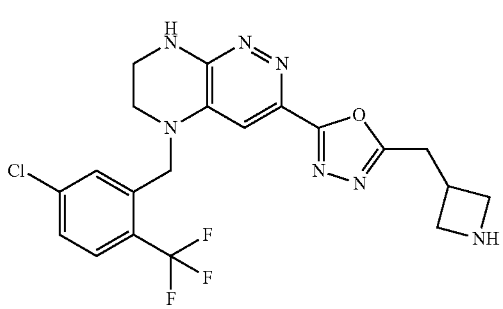 [SMILES: FC(F)(F)c1ccc(Cl)cc1CN1CCNc2nnc(-c3nnc(CC4CNC4)o3)cc21] | 465.13 |

| No. | Structure | m/z |
|-----|-----------|-----|
| 84 | 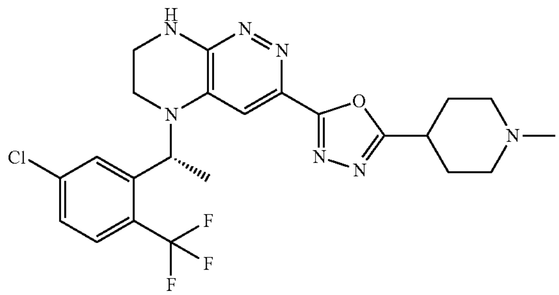 [SMILES: C[C@H](c1cc(Cl)ccc1C(F)(F)F)N1CCNc2nnc(-c3nnc(C4CCN(C)CC4)o3)cc21] | 507.18 |
| 85 | 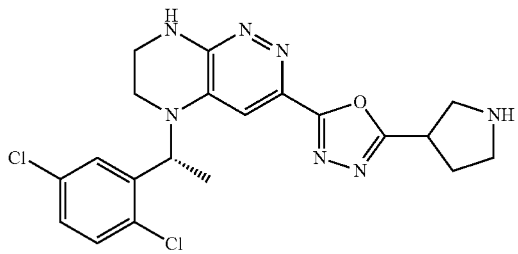 [SMILES: C[C@H](c1cc(Cl)ccc1Cl)N1CCNc2nnc(-c3nnc(C4CCNC4)o3)cc21] | 445.12 |
| 86 | 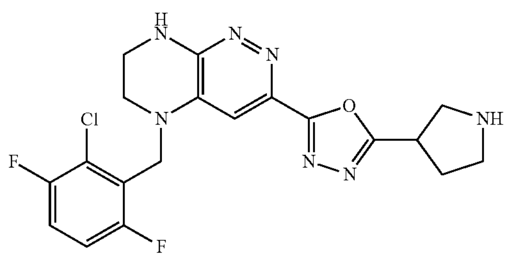 | 433.12 |
| 87 | 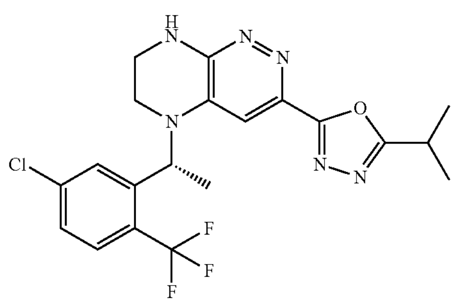 [SMILES: CC(C)c1nnc(-c2cc3c(nn2)NCCN3[C@H](C)c2cc(Cl)ccc2C(F)(F)F)o1] | 452.13 |
| 88 | 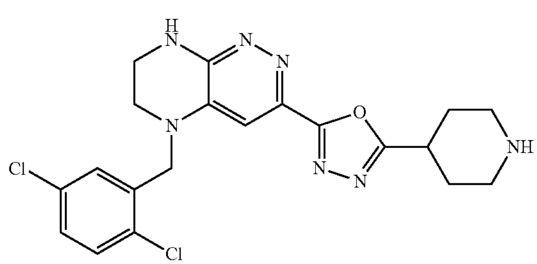 [SMILES: Clc1ccc(Cl)c(CN2CCNc3nnc(-c4nnc(C5CCNCC5)o4)cc32)c1] | 445.12 |

| No. | Structure | m/z |
|---|---|---|
| 89 | 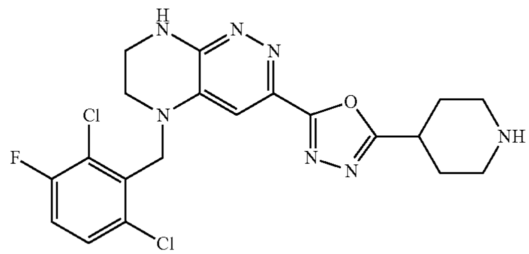 [SMILES: Fc1ccc(Cl)c(CN2CCNc3nnc(-c4nnc(C5CCNCC5)o4)cc32)c1Cl] | 463.11 |

20. Examples of Synthesis of 5-Substituted Derivatives of 3-(5-Substituted-5,6,7,8-Tetrahydropyrazine [2,3-c]Pyridazine-3-Yl)-1,2,4-Triazole 5-substituted derivatives of 3-(5-substituted-5,6,7,8-tetrahydropyrazine [2,3-c]pyridazine-3-yl)-1,2,4-triazole are synthesized from the corresponding Boc-protective 5-substituted derivatives of 3-chloro-5,6,7,8-tetrahydropyrazine [2,3-c]pyridazine analogously to compound 7, the synthesis method of which is described above. Examples of the prepared compounds are presented in Table.

| No. | Structure | m/z |
|---|---|---|
| 90 | 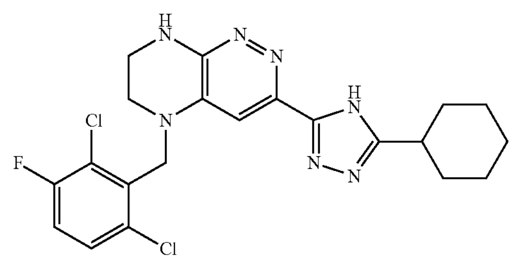 [SMILES: Fc1ccc(Cl)c(CN2CCNc3nnc(-c4nnc(C5CCCCC5)[nH]4)cc32)c1Cl] | 461.13 |
| 91 | 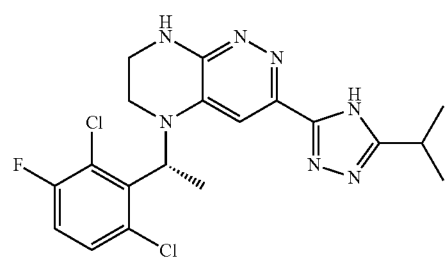 [SMILES: CC(C)c1nnc(-c2cc3c(nn2)NCCN3[C@H](C)c2c(Cl)ccc(F)c2Cl)[nH]1] | 435.11 |
| 92 | 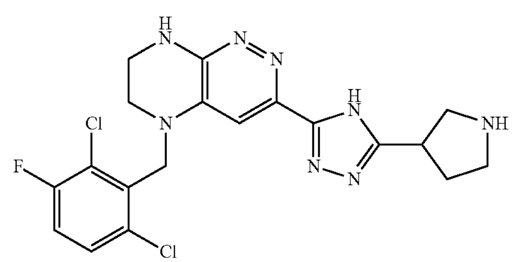 [SMILES: Fc1ccc(Cl)c(CN2CCNc3nnc(-c4nnc(C5CCNC5)[nH]4)cc32)c1Cl] | 448.11 |
| 93 | 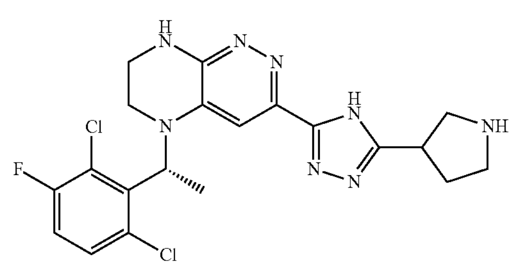 [SMILES: C[C@H](c1c(Cl)ccc(F)c1Cl)N1CCNc2nnc(-c3nnc(C4CCNC4)[nH]3)cc21] | 462.13 |

-continued
| No. | Structure | m/z |
|---|---|---|
| 94 | 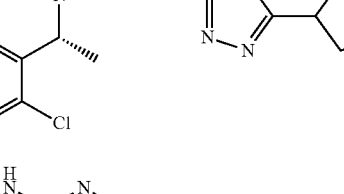 | 476.14 |
| 95 | 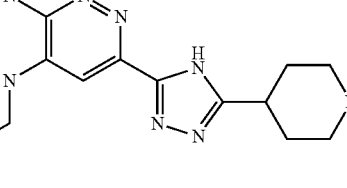 | 488.16 |
| 96 | 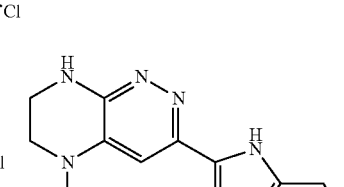 | 492.14 |
| 97 | 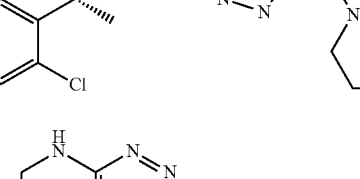 | 485.15 |
| 98 | 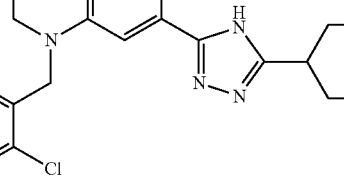 | 475.15 |
| 99 | 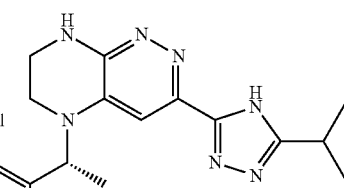 | 462.13 |

-continued

| No. | Structure | m/z |
|---|---|---|
| 100 | 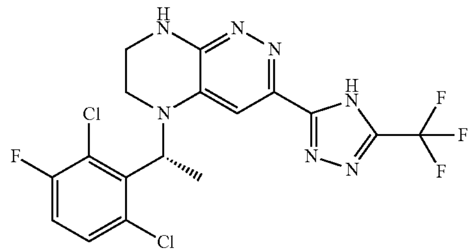 [SMILES: C[C@H](c1c(Cl)ccc(F)c1Cl)N1CCNc2nnc(-c3nnc(C(F)(F)F)[nH]3)cc21] | 461.05 |
| 101 | 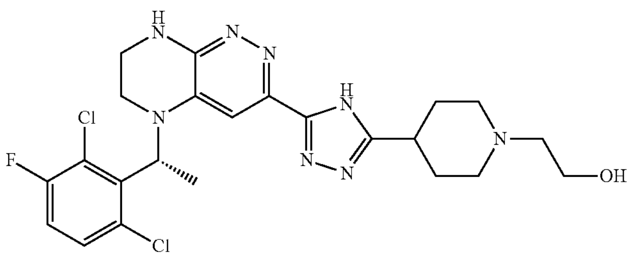 [SMILES: C[C@H](c1c(Cl)ccc(F)c1Cl)N1CCNc2nnc(-c3nnc(C4CCN(CCO)CC4)[nH]3)cc21] | 520.17 |
| 102 | 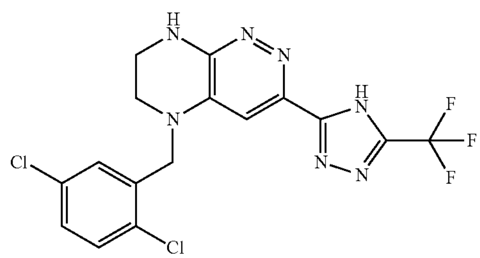 [SMILES: FC(F)(F)c1nnc(-c2cc3c(nn2)NCCN3Cc2cc(Cl)ccc2Cl)[nH]1] | 429.05 |
| 103 | 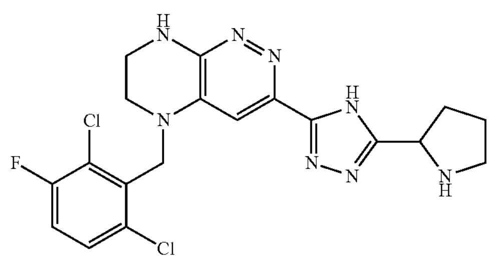 [SMILES: Fc1ccc(Cl)c(CN2CCNc3nnc(-c4nnc(C5CCCN5)[nH]4)cc32)c1Cl] | 448.11 |
| 104 | 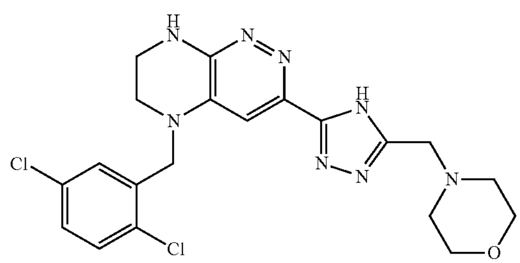 [SMILES: Clc1ccc(Cl)c(CN2CCNc3nnc(-c4nnc(CN5CCOCC5)[nH]4)cc32)c1] | 460.13 |
| 105 | 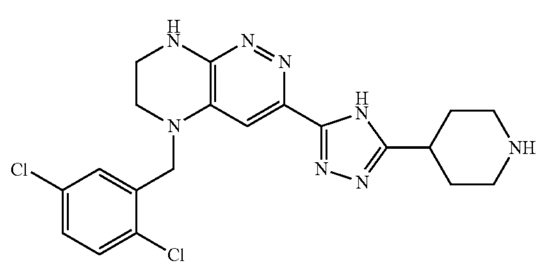 | 444.13 |

21. Examples of the Synthesis of Substituted Derivatives of 5-Substituted-N-Phenyl-5,6,7,8-Tetrahydropyrazine[2,3-c]Pyridazine-3-Carboxamide Substituted derivatives of S-substituted-N-phenyl-5,6,7,8-tetrahydropyrazine [2,3-c]pyridazine-3-carboxamide are synthesized from the corresponding Boc-protective 5-substituted derivatives of 3-chloro-5,6,7 8-tetrahydropyrazine [2,3-c]pyridazine analogously to compound 10, the synthesis method of which is described above. Examples of the prepared compounds are presented in Table.

| No. | Structure | m/z |
|-----|-----------|-----|
| 106 | 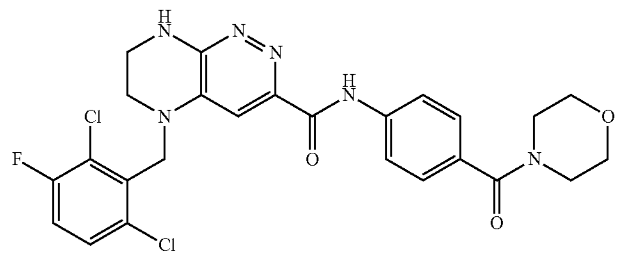 | 544.12 |
| 107 | 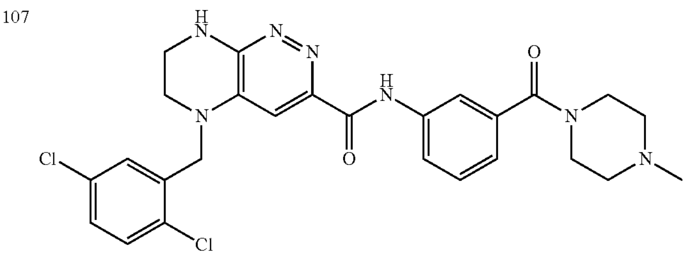 | 539.16 |
| 108 | 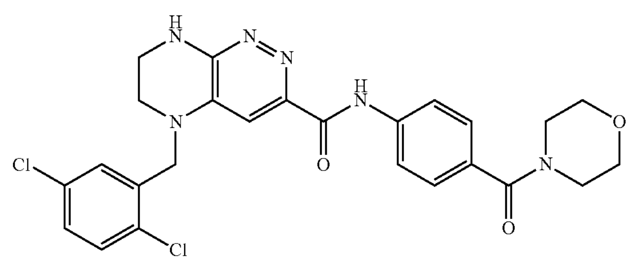 [SMILES: O=C(Nc1ccc(C(=O)N2CCOCC2)cc1)c1cc2c(nn1)NCCN2Cc1cc(Cl)ccc1Cl] | 526.13 |
| 109 | 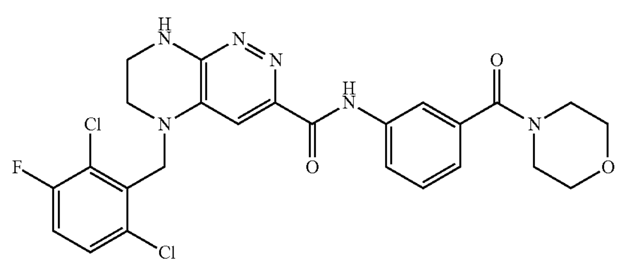 [SMILES: O=C(Nc1cccc(C(=O)N2CCOCC2)c1)c1cc2c(nn1)NCCN2Cc1c(Cl)ccc(F)c1Cl] | 544.12 |
| 110 | 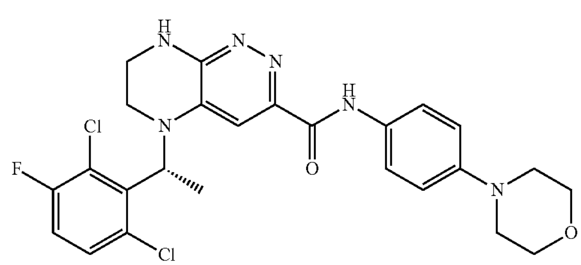 [SMILES: C[C@H](c1c(Cl)ccc(F)c1Cl)N1CCNc2nnc(C(=O)Nc3ccc(N4CCOCC4)cc3)cc21] | 530.14 |

-continued

| No. | Structure | m/z |
|---|---|---|
| 111 | 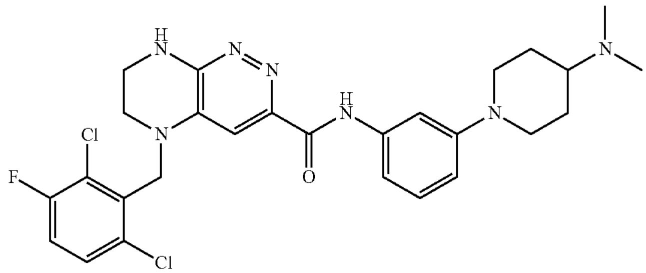 [SMILES: CN(C)C1CCN(c2cccc(NC(=O)c3cc4c(nn3)NCCN4Cc3c(Cl)ccc(F)c3Cl)c2)CC1] | 557.19 |
| 112 | 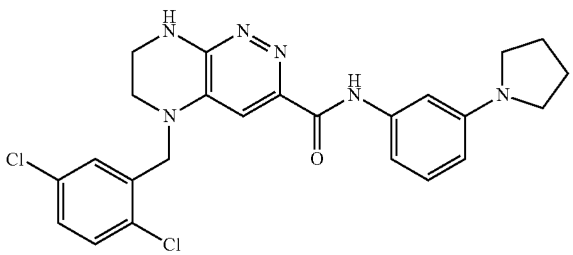 [SMILES: O=C(Nc1cccc(N2CCCC2)c1)c1cc2c(nn1)NCCN2Cc1cc(Cl)ccc1Cl] | 482.14 |
| 113 | 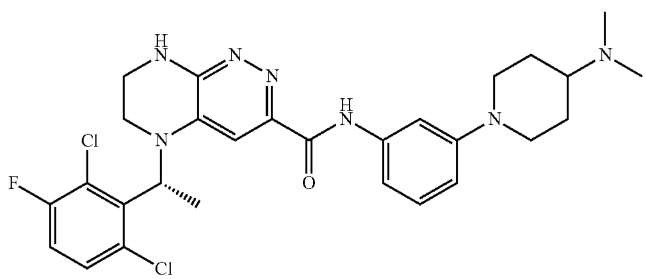 [SMILES: C[C@H](c1c(Cl)ccc(F)c1Cl)N1CCNc2nnc(C(=O)Nc3cccc(N4CCC(N(C)C)CC4)c3)cc21] | 571.20 |
| 114 | 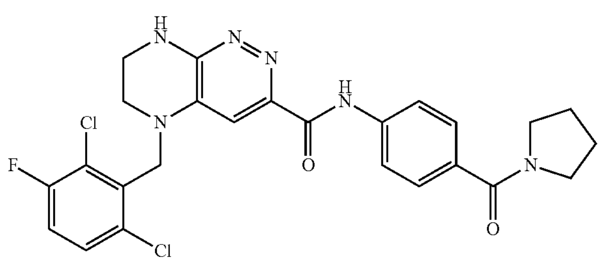 [SMILES: O=C(Nc1ccc(C(=O)N2CCCC2)cc1)c1cc2c(nn1)NCCN2Cc1c(Cl)ccc(F)c1Cl] | 528.12 |
| 115 | 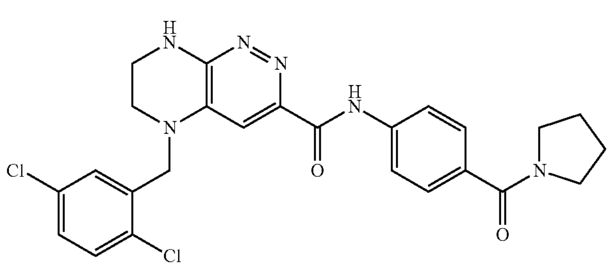 [SMILES: O=C(Nc1ccc(C(=O)N2CCCC2)cc1)c1cc2c(nn1)NCCN2Cc1cc(Cl)ccc1Cl] | 510.13 |

-continued

| No. | Structure | m/z |
|---|---|---|
| 116 | 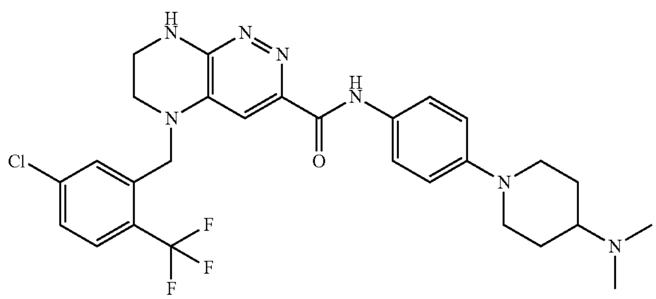 [SMILES: CN(C)C1CCN(c2ccc(NC(=O)c3cc4c(nn3)NCCN4Cc3cc(Cl)ccc3C(F)(F)F)cc2)CC1] | 573.22 |
| 117 | 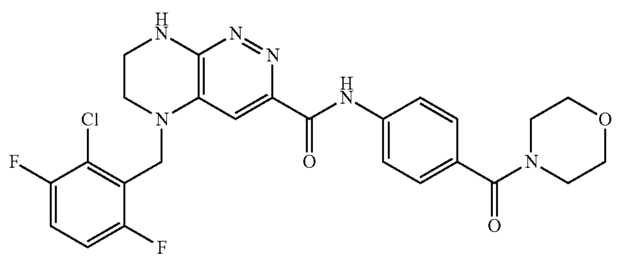 [SMILES: O=C(Nc1ccc(C(=O)N2CCOCC2)cc1)c1cc2c(nn1)NCCN2Cc1c(F)ccc(F)c1Cl] | 528.15 |
| 118 | 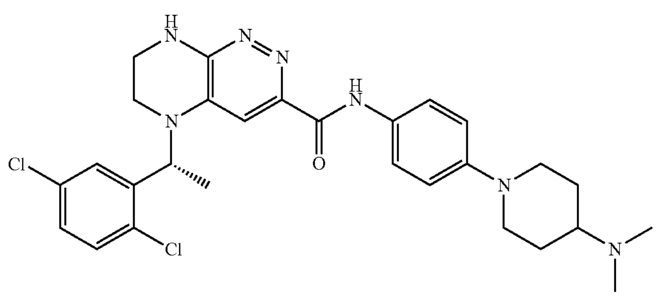 [SMILES: C[C@H](c1cc(Cl)ccc1Cl)N1CCNc2nnc(C(=O)Nc3ccc(N4CCC(N(C)C)CC4)cc3)cc21] | 553.21 |
| 119 | 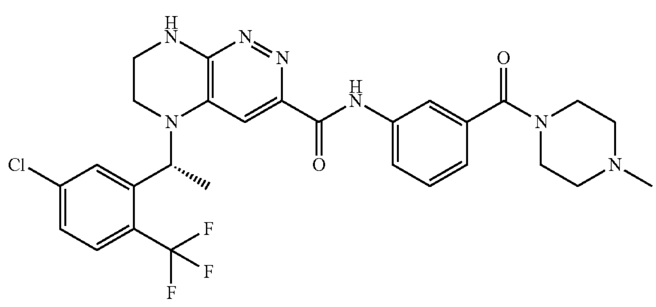 [SMILES: C[C@H](c1cc(Cl)ccc1C(F)(F)F)N1CCNc2nnc(C(=O)Nc3cccc(C(=O)N4CCN(C)CC4)c3)cc21] | 587.20 |
| 120 | 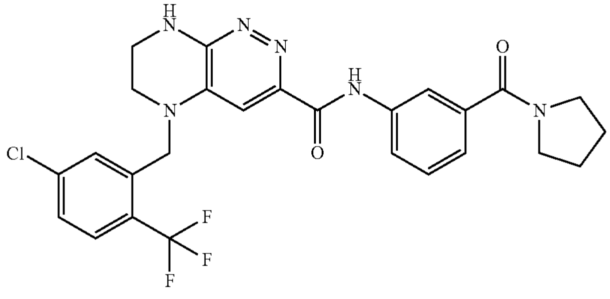 [SMILES: O=C(Nc1cccc(C(=O)N2CCCC2)c1)c1cc2c(nn1)NCCN2Cc1cc(Cl)ccc1C(F)(F)F] | 544.16 |

| No. | Structure | m/z |
|---|---|---|
| 121 | 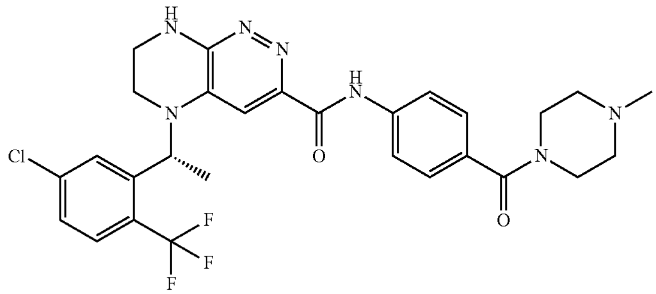 [SMILES: C[C@H](c1cc(Cl)ccc1C(F)(F)F)N1CCNc2nnc(C(=O)Nc3ccc(C(=O)N4CCN(C)CC4)cc3)cc21] | 587.20 |
| 122 | 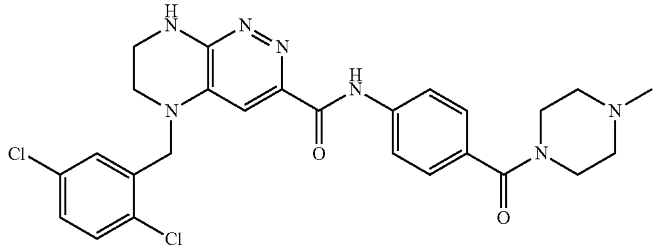 [SMILES: CN1CCN(C(=O)c2ccc(NC(=O)c3cc4c(nn3)NCCN4Cc3cc(Cl)ccc3Cl)cc2)CC1] | 539.16 |
| 123 | 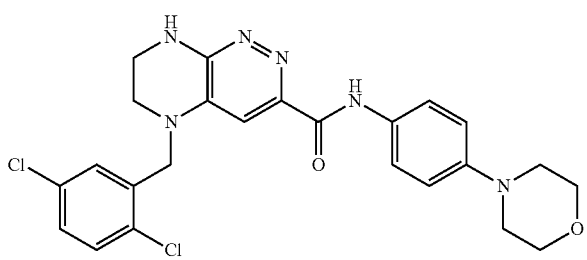 [SMILES: O=C(Nc1ccc(N2CCOCC2)cc1)c1cc2c(nn1)NCCN2Cc1cc(Cl)ccc1Cl] | 498.13 |

22. Examples of the Synthesis of Substituted Derivatives of 5-Substituted-N-Phenyl-5,6,7,8-Tetrahydropyrazine[2,3-c]Pyridazine-3-Amide Substituted derivatives of 5-substituted-N-phenyl-5,6,7,8-tetrahydropyrazine [2,3-c]pyridazine-3-amide are synthesized from the corresponding Boc-protective 5-substituted derivatives of 3-chloro-5,6,7 8-tetrahydropyrazine [2,3-c] pyridazine analogously to compound 11, the synthesis method of which is described above. Examples of the prepared compounds are presented in Table.

| No. | Structure | m/z |
|---|---|---|
| 124 | 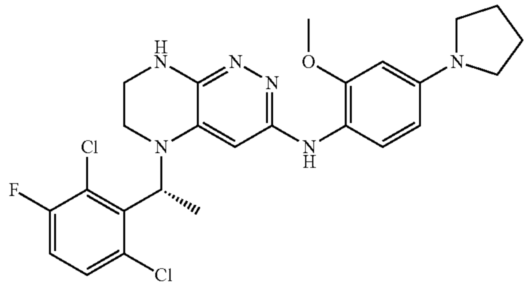 [SMILES: COc1cc(N2CCCC2)ccc1Nc1cc2c(nn1)NCCN2[C@H](C)c1c(Cl)ccc(F)c1Cl] | 516.16 |

-continued
| No. | Structure | m/z |
|---|---|---|
| 125 | 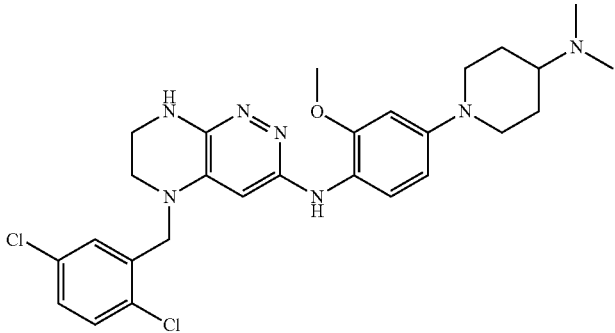 [SMILES: COc1cc(N2CCC(N(C)C)CC2)ccc1Nc1cc2c(nn1)NCCN2Cc1cc(Cl)ccc1Cl] | 541.21 |
| 126 | 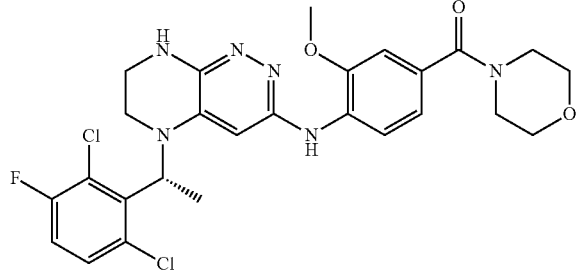 [SMILES: COc1cc(C(=O)N2CCOCC2)ccc1Nc1cc2c(nn1)NCCN2[C@H](C)c1c(Cl)ccc(F)c1Cl] | 560.15 |
| 127 | 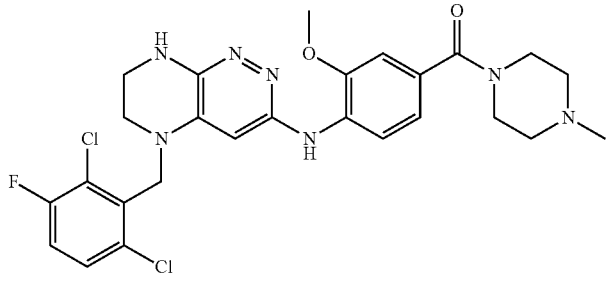 [SMILES: COc1cc(C(=O)N2CCN(C)CC2)ccc1Nc1cc2c(nn1)NCCN2Cc1c(Cl)ccc(F)c1Cl] | 559.17 |
| 128 | 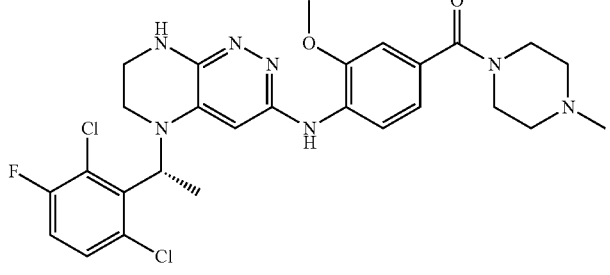 | 573.18 |
| 129 | 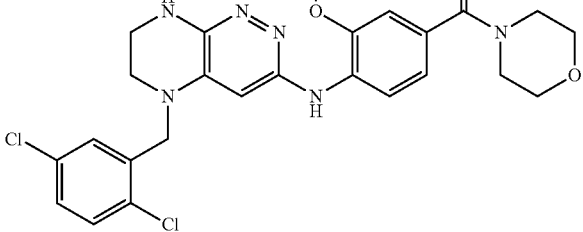 | 528.14 |

| No. | Structure | m/z |
|---|---|---|
| 130 | 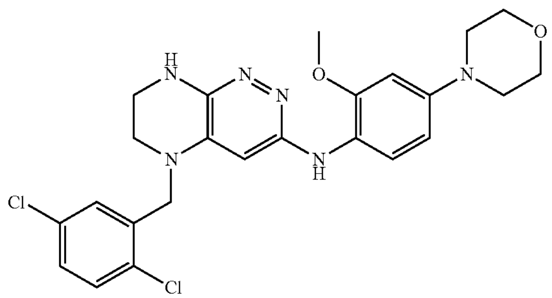 [SMILES: COc1cc(N2CCOCC2)ccc1Nc1cc2c(nn1)NCCN2Cc1cc(Cl)ccc1Cl] | 500.15 |
| 131 | 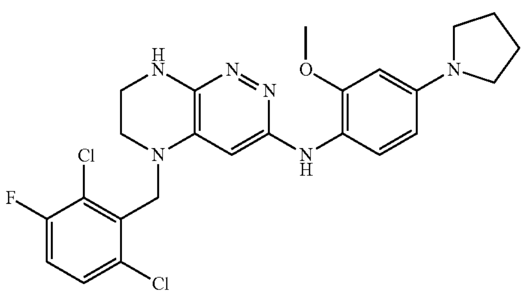 [SMILES: COc1cc(N2CCCC2)ccc1Nc1cc2c(nn1)NCCN2Cc1c(Cl)ccc(F)c1Cl] | 502.15 |
| 132 | 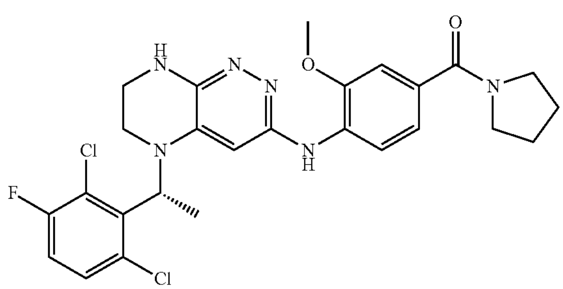 [SMILES: COc1cc(C(=O)N2CCCC2)ccc1Nc1cc2c(nn1)NCCN2[C@H](C)c1c(Cl)ccc(F)c1Cl] | 544.16 |
| 133 | 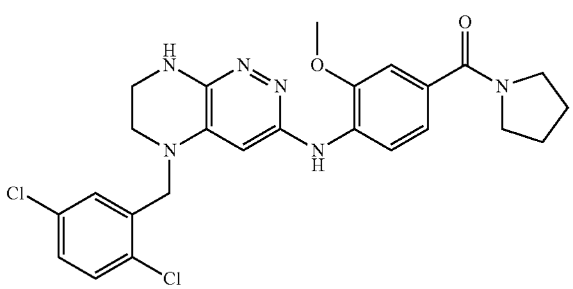 [SMILES: COc1cc(C(=O)N2CCCC2)ccc1Nc1cc2c(nn1)NCCN2Cc1cc(Cl)ccc1Cl] | 512.15 |
| 134 | 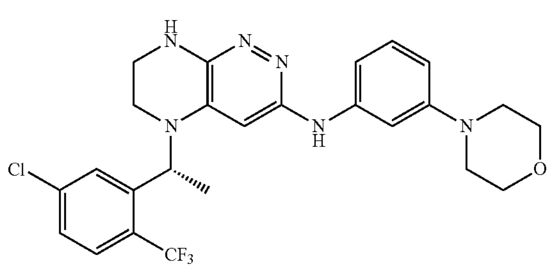 [SMILES: C[C@H](c1cc(Cl)ccc1C(F)(F)F)N1CCNc2nnc(Nc3cccc(N4CCOCC4)c3)cc21] | 518.18 |

-continued

| No. | Structure | m/z |
|---|---|---|
| 135 | 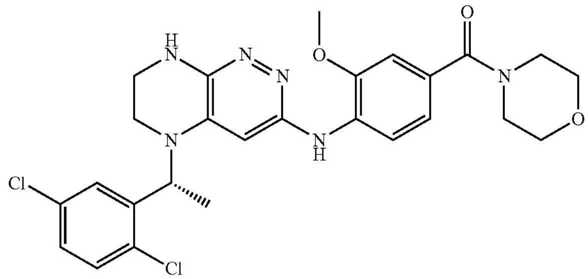 [SMILES: COc1cc(C(=O)N2CCOCC2)ccc1Nc1cc2c(nn1)NCCN2[C@H](C)c1cc(Cl)ccc1Cl] | 542.16 |
| 136 | 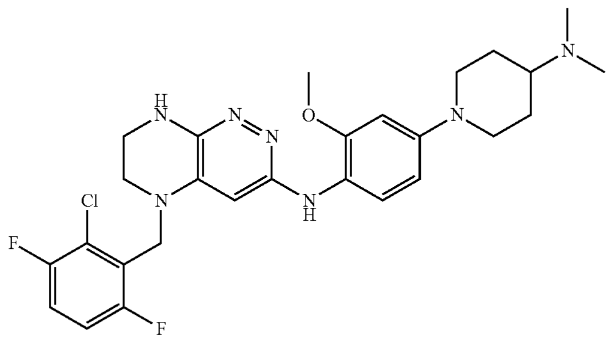 [SMILES: COc1cc(N2CCC(N(C)C)CC2)ccc1Nc1cc2c(nn1)NCCN2Cc1c(F)ccc(F)c1Cl] | 543.23 |
| 137 | 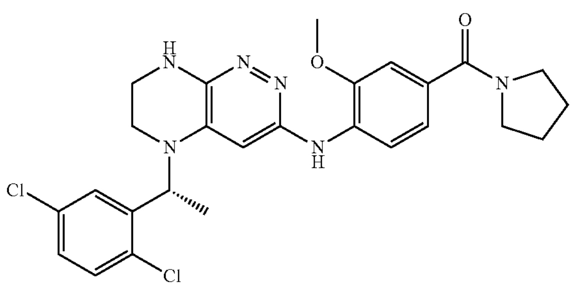 [SMILES: COc1cc(C(=O)N2CCCC2)ccc1Nc1cc2c(nn1)NCCN2[C@H](C)c1cc(Cl)ccc1Cl] | 526.17 |
| 138 | 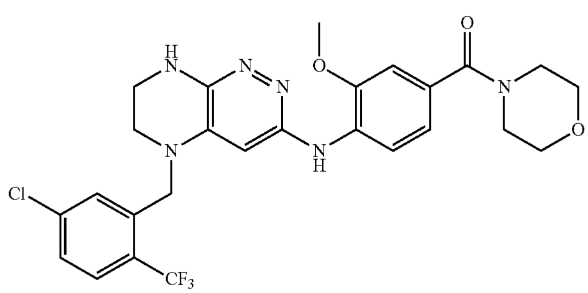 [SMILES: COc1cc(C(=O)N2CCOCC2)ccc1Nc1cc2c(nn1)NCCN2Cc1cc(Cl)ccc1C(F)(F)F] | 562.17 |
| 139 | 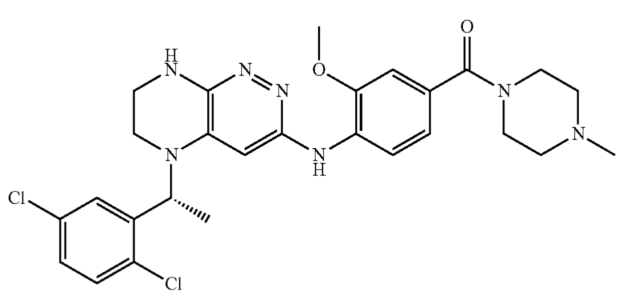 [SMILES: COc1cc(C(=O)N2CCN(C)CC2)ccc1Nc1cc2c(nn1)NCCN2[C@H](C)c1cc(Cl)ccc1Cl] | 555.19 |

-continued

| No. | Structure | m/z |
|---|---|---|
| 140 | 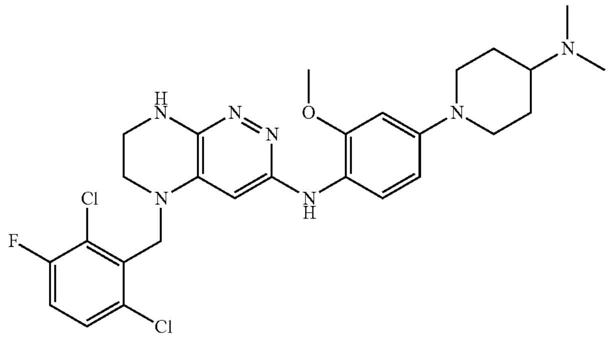 [SMILES: COc1cc(N2CCC(N(C)C)CC2)ccc1Nc1cc2c(nn1)NCCN2Cc1c(Cl)ccc(F)c1Cl] | 559.20 |
| 141 | 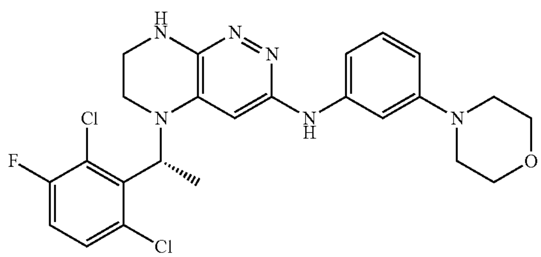 [SMILES: C[C@H](c1c(Cl)ccc(F)c1Cl)N1CCNc2nnc(Nc3cccc(N4CCOCC4)c3)cc21] | 502.15 |

23. Examples of the Synthesis of Substituted Derivatives of 5-Substituted-3-Phenyl-5,6,7,8-Tetrahydropyrazine[2,3-c]Pyridazine Substituted derivatives of 5-substituted-3-phenyl-5,6,7,8-tetrahydropyrazine [2,3-c]pyridazine are synthesized from the corresponding Boc-protective 5-substituted derivatives of 3-chloro-5,6,7,8-tetrahydropyrazine [2,3-c]pyridazine analogously to compound 12, the synthesis method of which is described above. Examples of the prepared compounds are presented in Table.

| No. | Structure | m/z |
|---|---|---|
| 142 | 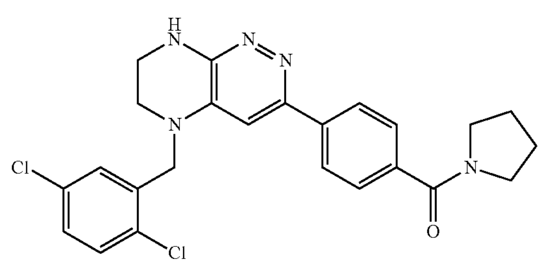 [SMILES: O=C(c1ccc(-c2cc3c(nn2)NCCN3Cc2cc(Cl)ccc2Cl)cc1)N1CCCC1] | 467.13 |
| 143 | 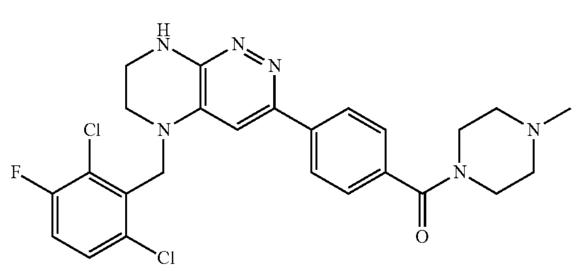 [SMILES: CN1CCN(C(=O)c2ccc(-c3cc4c(nn3)NCCN4Cc3c(Cl)ccc(F)c3Cl)cc2)CC1] | 514.15 |

-continued

| No. | Structure | m/z |
|-----|-----------|------|
| 144 | 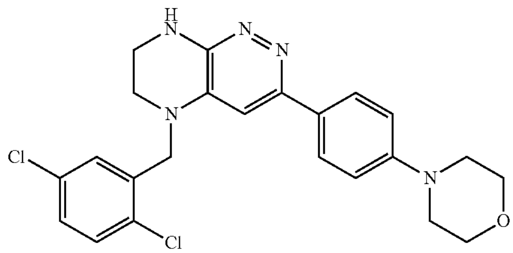 [SMILES: Clc1ccc(Cl)c(CN2CCNc3nnc(-c4ccc(N5CCOCC5)cc4)cc32)c1] | 455.13 |
| 145 | 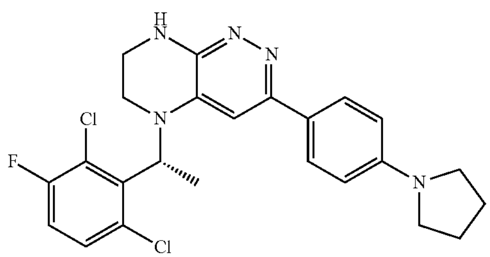 [SMILES: C[C@H](c1c(Cl)ccc(F)c1Cl)N1CCNc2nnc(-c3ccc(N4CCCC4)cc3)cc21] | 471.14 |
| 146 | 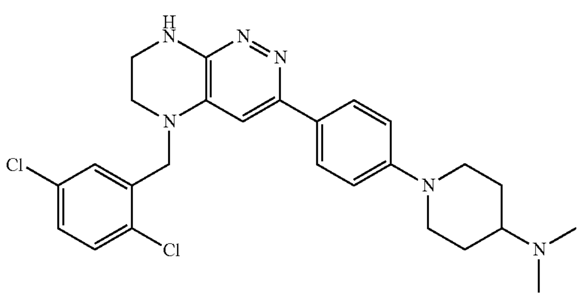 [SMILES: CN(C)C1CCN(c2ccc(-c3cc4c(nn3)NCCN4Cc3cc(Cl)ccc3Cl)cc2)CC1] | 496.19 |
| 147 | 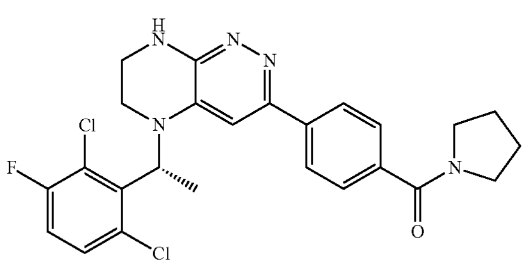 [SMILES: C[C@H](c1c(Cl)ccc(F)c1Cl)N1CCNc2nnc(-c3ccc(C(=O)N4CCCC4)cc3)cc21] | 499.13 |
| 148 | 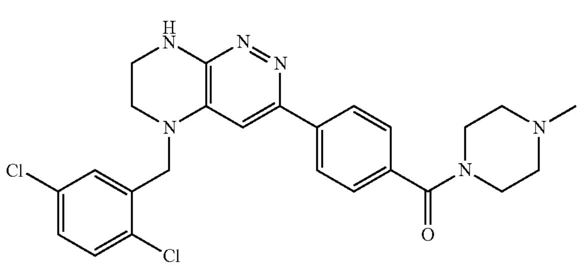 [SMILES: CN1CCN(C(=O)c2ccc(-c3cc4c(nn3)NCCN4Cc3cc(Cl)ccc3Cl)cc2)CC1] | 496.15 |

| No. | Structure | m/z |
|---|---|---|
| 149 | 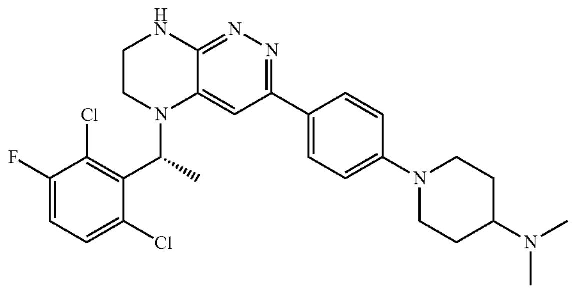 [SMILES: C[C@H](c1c(Cl)ccc(F)c1Cl)N1CCNc2nnc(-c3ccc(N4CCC(N(C)C)CC4)cc3)cc21] | 528.20 |
| 150 | 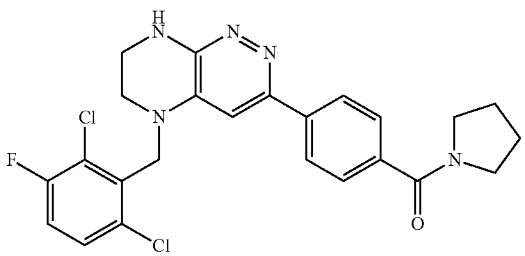 [SMILES: O=C(c1ccc(-c2cc3c(nn2)NCCN3Cc2c(Cl)ccc(F)c2Cl)cc1)N1CCCC1] | 485.12 |
| 151 | 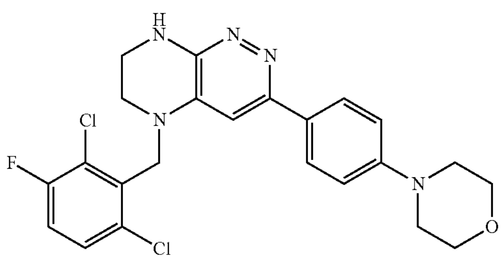 [SMILES: Fc1ccc(Cl)c(CN2CCNc3nnc(-c4ccc(N5CCOCC5)cc4)cc32)c1Cl] | 473.12 |
| 152 | 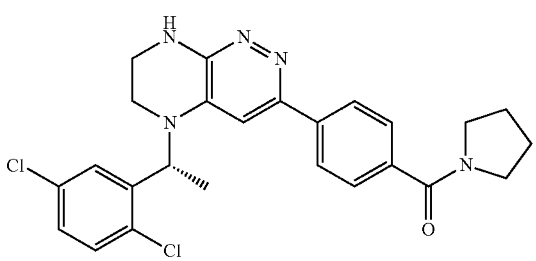 [SMILES: C[C@H](c1cc(Cl)ccc1Cl)N1CCNc2nnc(-c3ccc(C(=O)N4CCCC4)cc3)cc21] | 481.14 |
| 153 | 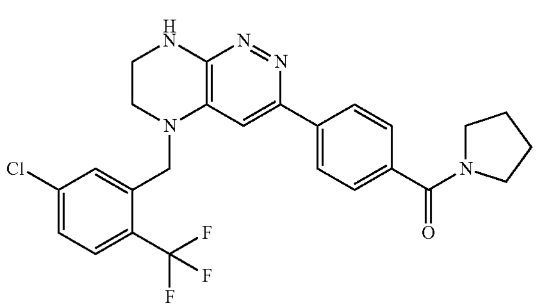 [SMILES: O=C(c1ccc(-c2cc3c(nn2)NCCN3Cc2cc(Cl)ccc2C(F)(F)F)cc1)N1CCCC1] | 501.15 |

| No. | Structure | m/z |
|---|---|---|
| 154 | 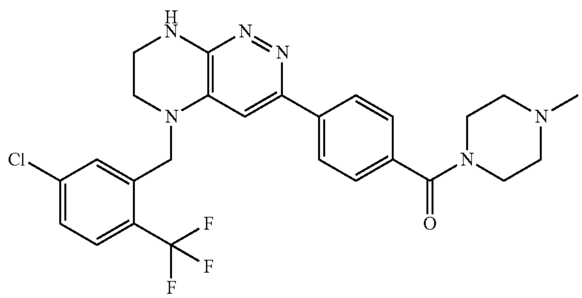 [SMILES: CN1CCN(C(=O)c2ccc(-c3cc4c(nn3)NCCN4Cc3cc(Cl)ccc3C(F)(F)F)cc2)CC1] | 530.18 |
| 155 | 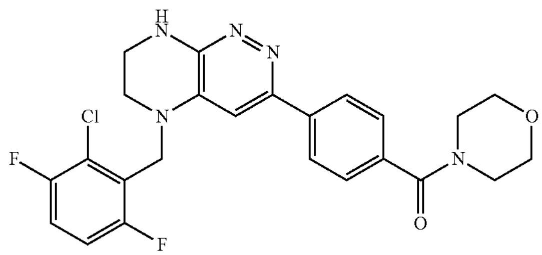 [SMILES: O=C(c1ccc(-c2cc3c(nn2)NCCN3Cc2c(F)ccc(F)c2Cl)cc1)N1CCOCC1] | 585.14 |
| 156 | 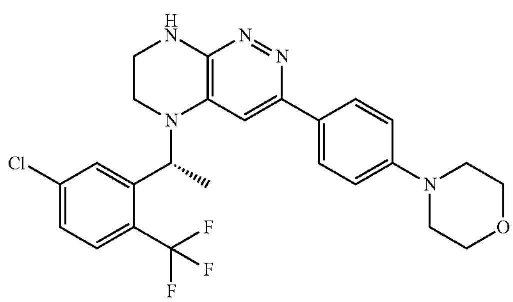 [SMILES: C[C@H](c1cc(Cl)ccc1C(F)(F)F)N1CCNc2nnc(-c3ccc(N4CCOCC4)cc3)cc21] | 503.17 |
| 157 | 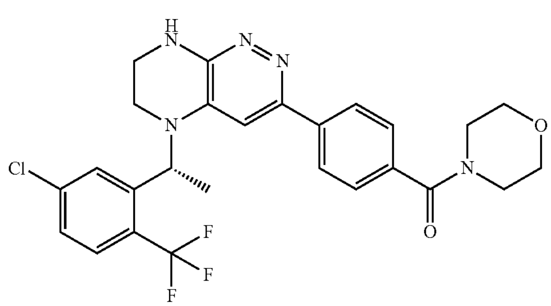 [SMILES: C[C@H](c1cc(Cl)ccc1C(F)(F)F)N1CCNc2nnc(-c3ccc(C(=O)N4CCOCC4)cc3)cc21] | 531.16 |

24. Characteristics of the Biological Activity of Compounds

The biological activity of the compounds of the present invention has been studied by various methods. For example, the inhibition of kinase activity by these compounds has been studies. Some of the compounds showed significant inhibitory activity at nanomolar concentrations toward kinase ALK, ALK L1196M, EGFR, ROS1, MET. In addition, some compounds showed a significant antiproliferative activity on cells Karpas-299, SU-DHL-1, NCI-H2228, NCI-H3122 at concentrations of 1-1000 nM.

Illustrative examples of compounds having inhibitory and antiproliferative activity are shown below.

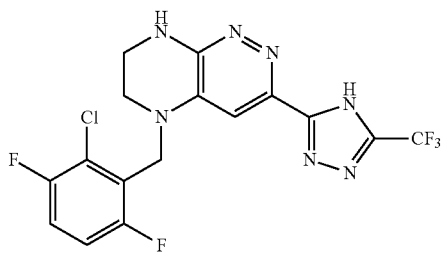 [SMILES: Fc1ccc(Cl)c(CN2CCNc3nnc(-c4nnc(C(F)(F)F)[nH]4)cc32)c1Cl]

119
-continued
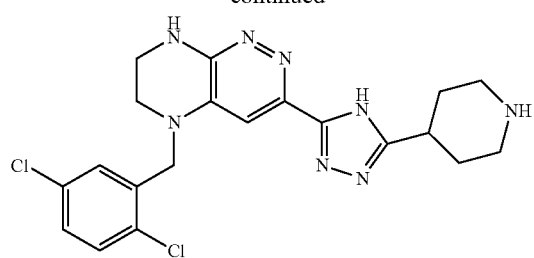
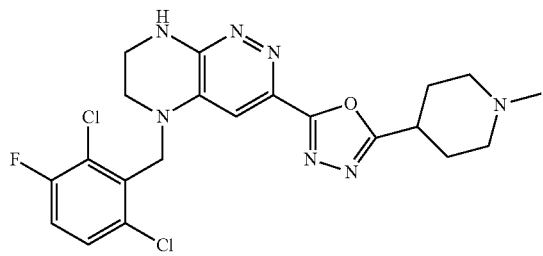
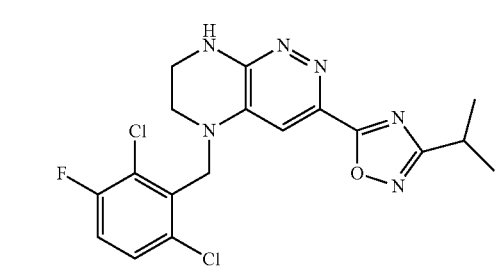
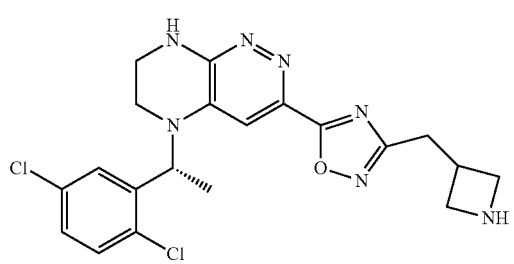
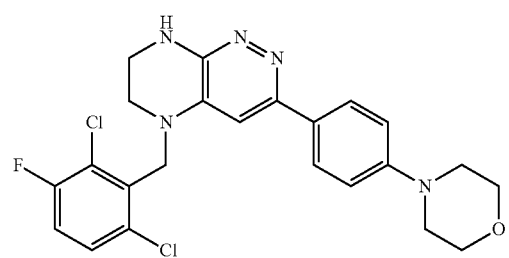 [SMILES: Fc1ccc(Cl)c(CN2CCNc3nnc(-c4ccc(N5CCOCC5)cc4)cc32)c1Cl]
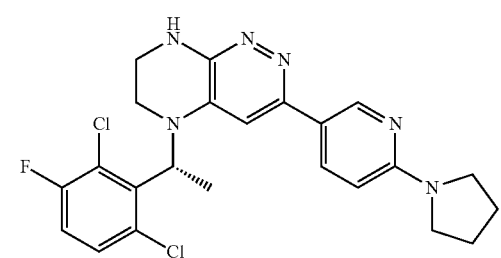 [SMILES: C[C@H](c1c(Cl)ccc(F)c1Cl)N1CCNc2nnc(-c3ccc(N4CCCC4)nc3)cc21]
120
-continued
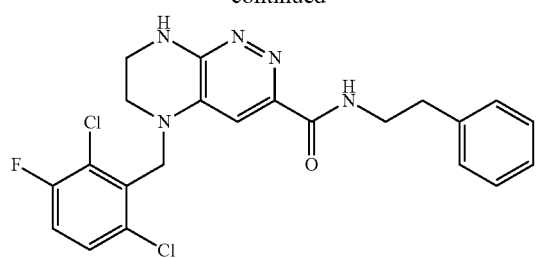
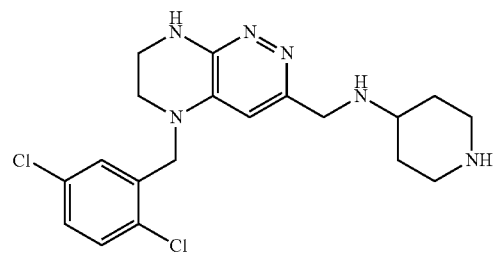
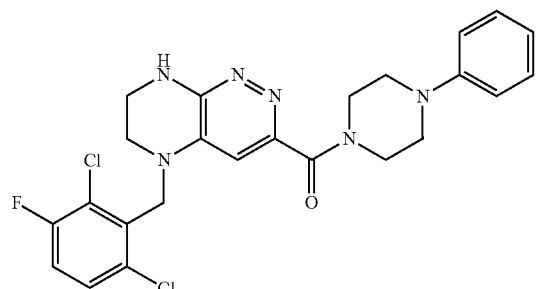
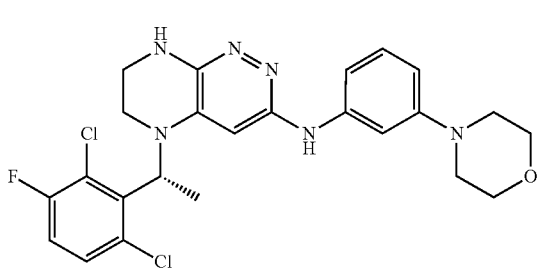
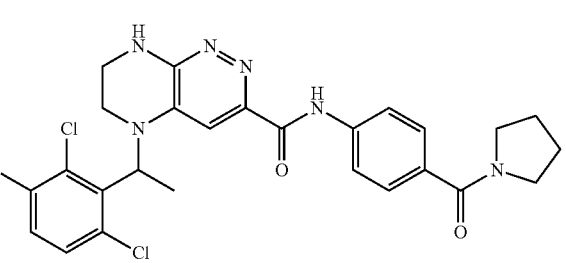
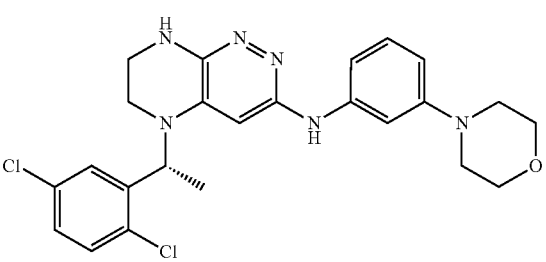

-continued

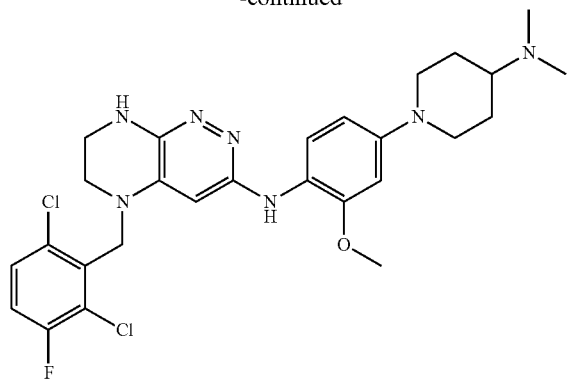
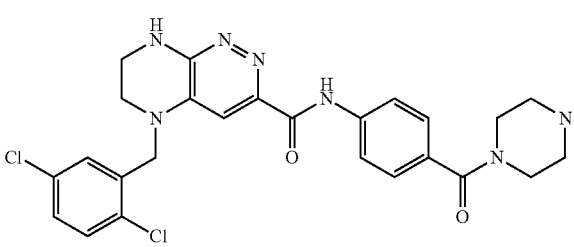
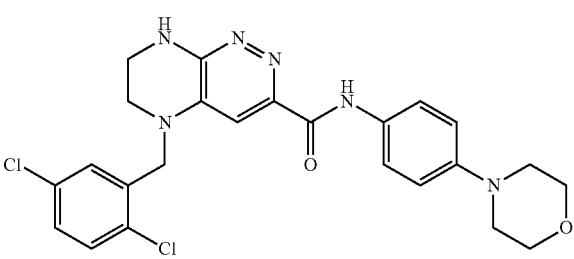
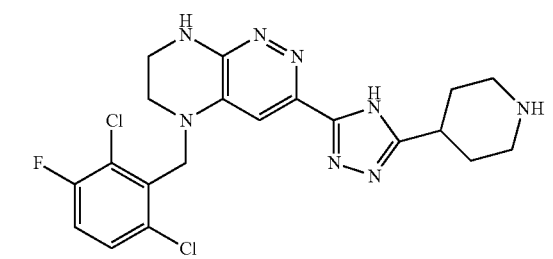
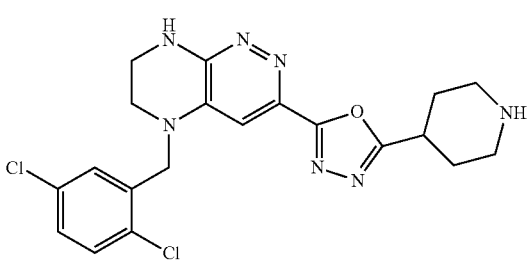
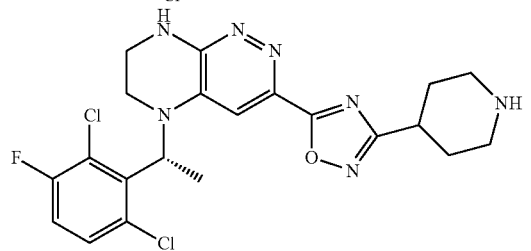

-continued

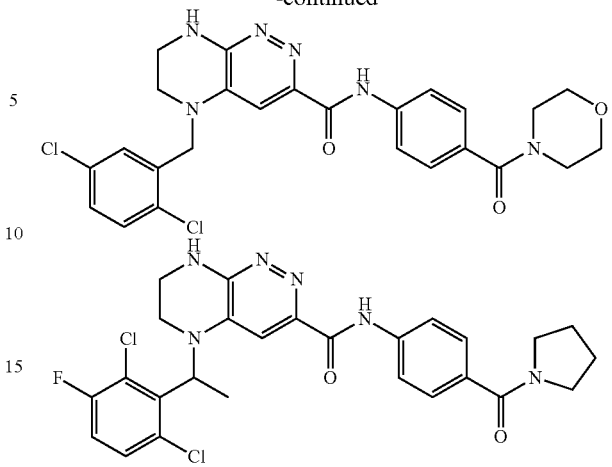

The invention is further illustrated by the following non-limiting examples.

24.1. Inhibition of Kinases

The compounds of the present invention have been studied with respect to the kinase inhibition ability being of interest for the treatment of oncological, chronic inflammatory and other diseases. List of kinases which inhibition was investigated in accordance with the described method includes, (but is fundamentally not limited to) kinases ALK, JAK2, BRAF, MET, TIE-2, FLT3, ABL, LCK, LYN, SRC, FYN, SYK, ZAP70, ITK, TEC, BTK, EGFR, ERB2, PDG-FRa, PDGFRb, KFR, IGF-1R, FLT1, TEK, AKT, ROS1, EPHA1, as well as mutant forms, including those conferring resistance to existing methods of the treatment of oncological diseases, e.g., mutant forms ALK L1196M, C1156Y, F1174L, G1269A (Choi, Y. L. et. al., *N Engl J Med*, 2010, 363, 1734-9; Sasaki, T. et. al., *Cancer Res*, 2010, 70, 10038-43; Doebele, R. C. et. al., *Clin Cancer Res*, 2012).

Kinases, in the form of a kinase domain or full length protein, attached to glutathione-S-transferase (GST) or polyhistidine fragments, were expressed in insect cells infected with baculovirus (e.g., Sf21) or *E. Coli* cells. After isolation from the cells, the proteins were purified to almost complete homogeneity by affinity chromatography according to known methods. In some cases the kinases were co-expressed or mixed with purified or partially purified regulatory polypeptides prior to the activity measurement.

Activity and inhibition of kinases were determined in accordance with known protocols. The transfer rate of labeled $^{33}PO_4$ with ATP on synthetic substrates of poly (Glu, Tyr) 4:1 or poly (Arg, Ser) 3:1, attached to the bioactive surface of microtiter carrying base, served as measure of enzyme activity. After a period of incubation (120 min), the carrying base was washed with 0.5% phosphoric acid, liquid scintillant was added, and the amount of the transferred phosphate was determined based on the amount of scintillation counting in a liquid scintillation detector. $IC_{50}$ corresponded to the concentration of the substance which reduced the amount of $^{33}P$, transferred to the substrate, connected with carrying base by 50%.

Other methods can also be used to determine the inhibition of kinases, based on measuring the degree of transfer of phosphate to a peptide or polypeptide comprising a tyrosine, serine or threonine, and present in dissolved or immobilized form.

The compounds described in this invention have nanomolar values of $IC_{50}$ for various kinases, including ALK, MET, EGFR, and ROS1. Also, the compounds described herein are selective, and do not significantly inhibit kinases such as ABL, AKT2, AURA, AURC, AXL, CDK2, CTK, FAK, IGF1R, IR, IRR, ITK, mTOR, MUSK, PKA, PKCθ, RON, SYK, SRC, TYRO3, ZAP70 in concentrations up to 1000 nM.

Below there is a list of compounds inhibiting ALK kinase with value of $IC_{50}$ less than 100 nM

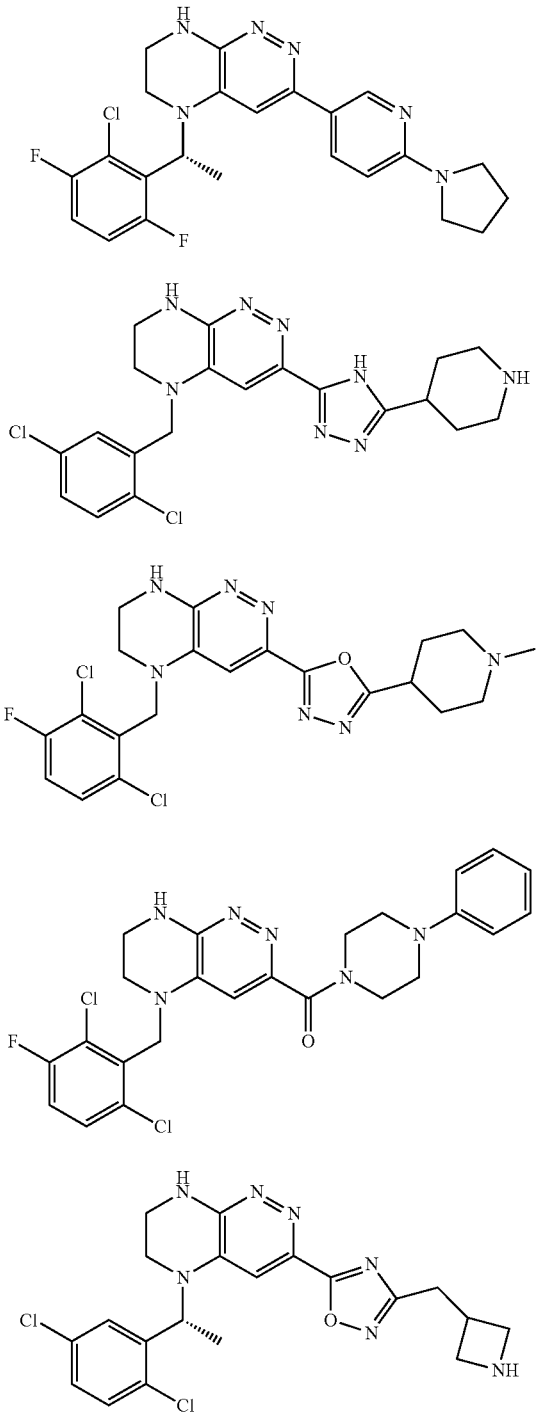

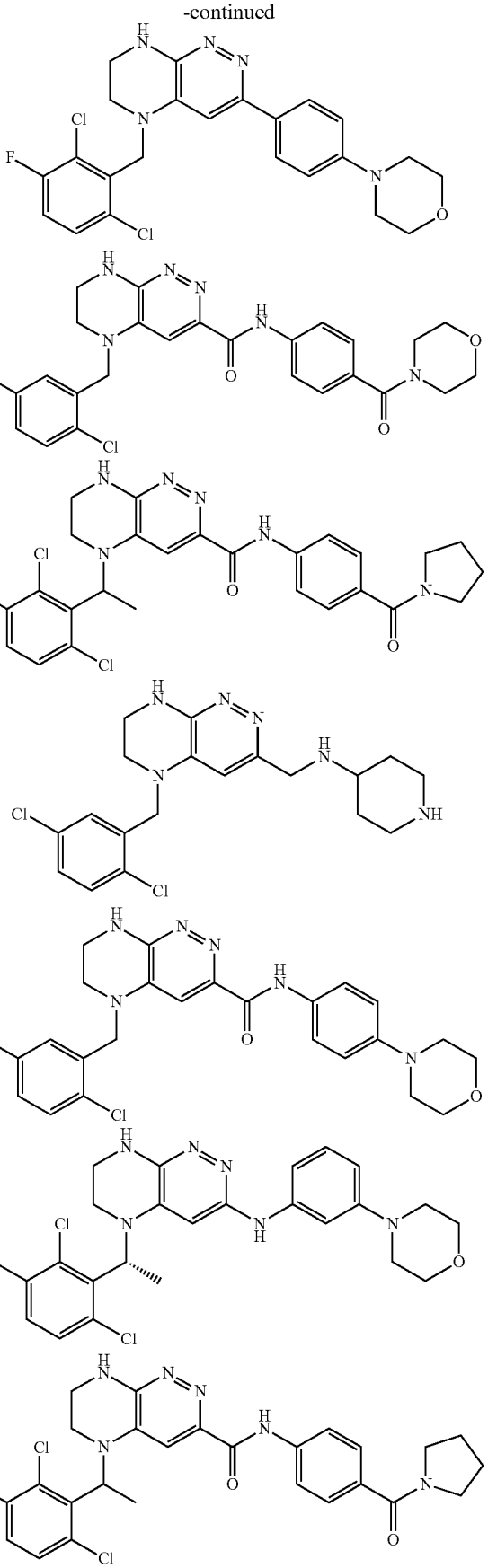

125
-continued
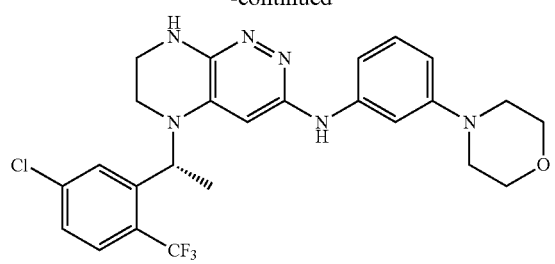
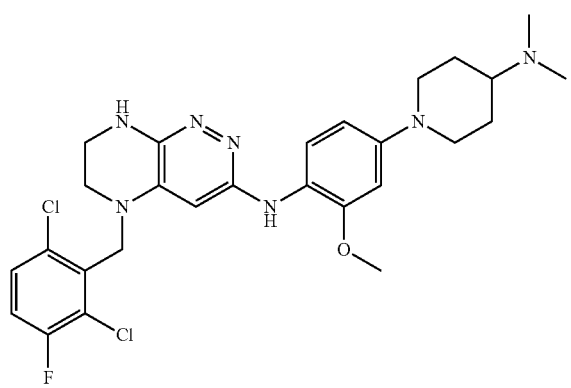
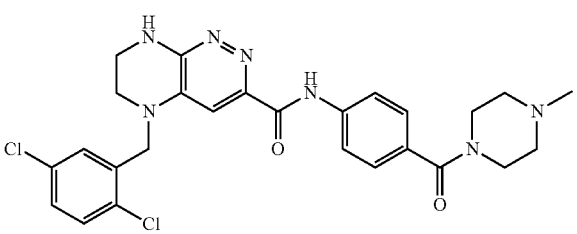
The list of compounds, inhibiting mutant form of kinase ALK L1196M with the value of IC$_{50}$ less than 100 nM
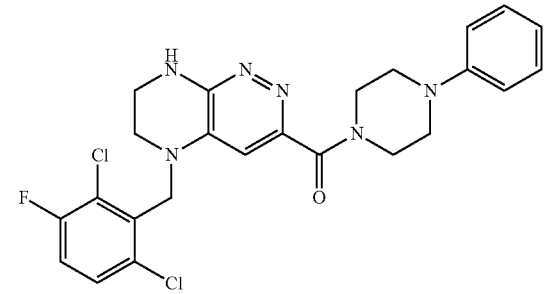
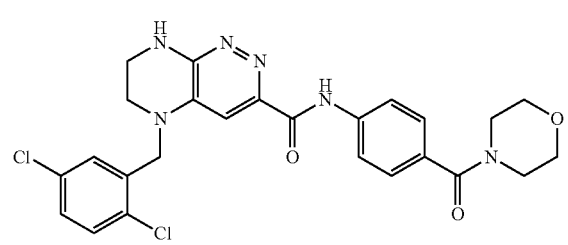
126
-continued
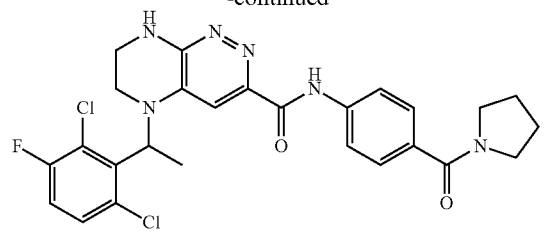
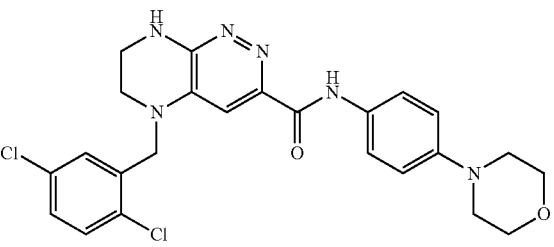
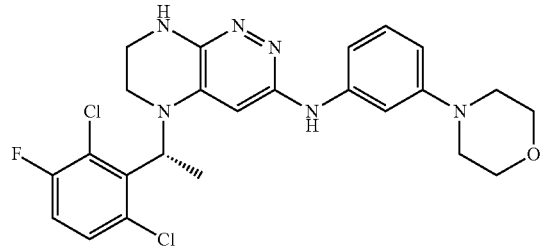
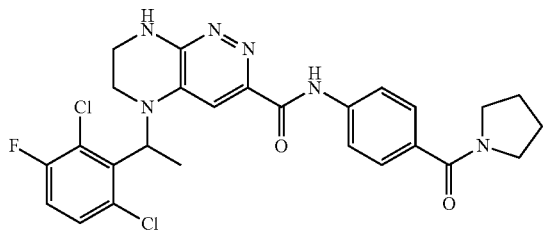
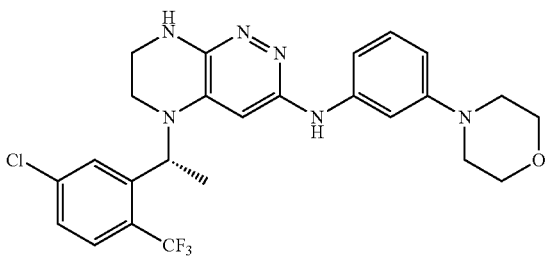
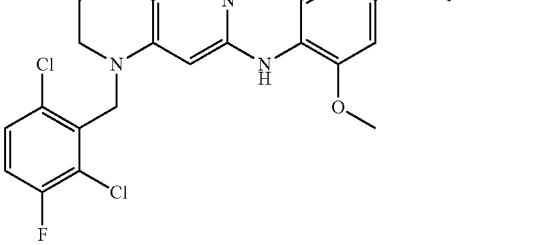

127
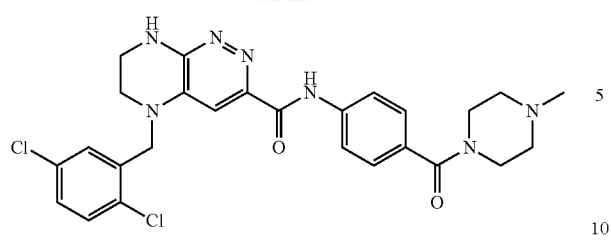
The list of compounds, inhibiting kinase ROS1 with the value of $IC_{50}$ less than 1 μM
128
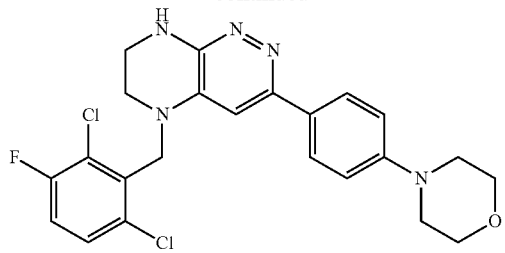
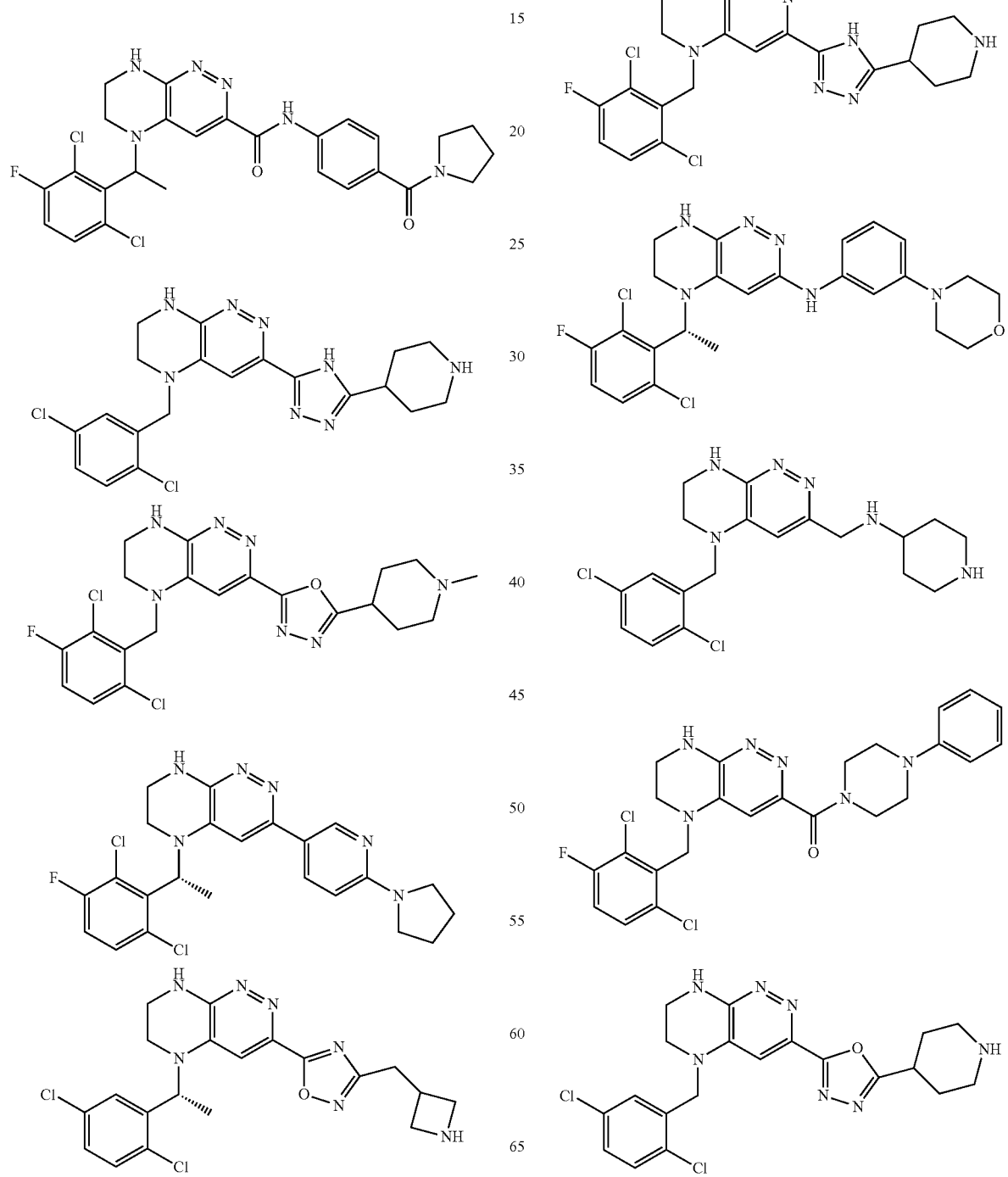

129
-continued
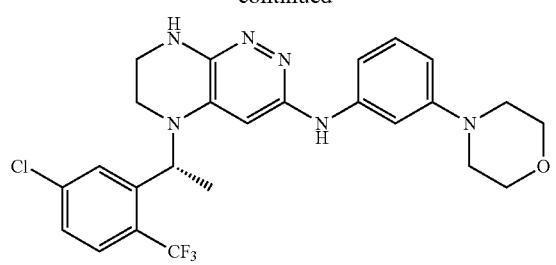
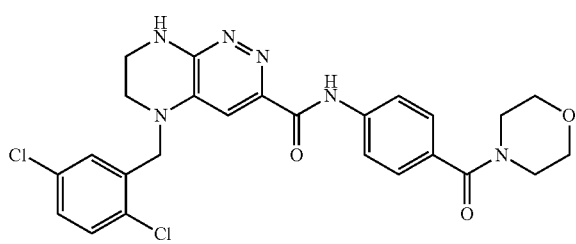
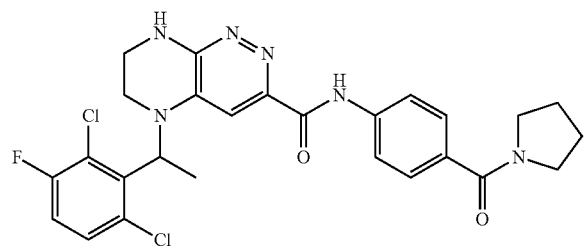
130
-continued
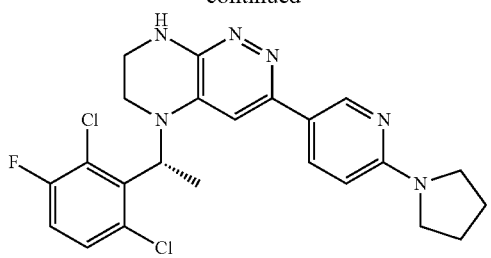
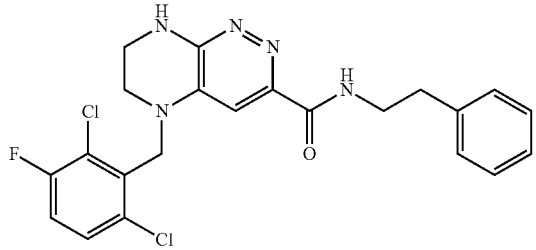 [SMILES: O=C(NCCc1ccccc1)c1cc2c(nn1)NCCN2Cc1c(Cl)ccc(F)c1Cl]
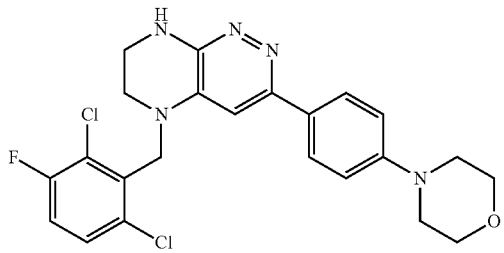
The list of compounds, inhibiting mutant form of kinase EGFR (d746-750) with the value of IC$_{50}$ less than 10 μM
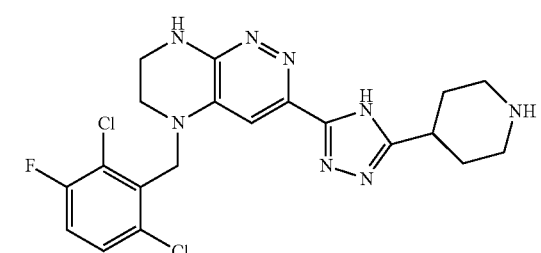
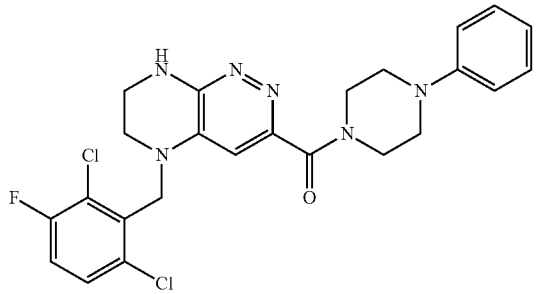 [SMILES: O=C(c1cc2c(nn1)NCCN2Cc1c(Cl)ccc(F)c1Cl)N1CCN(c2ccccc2)CC1]
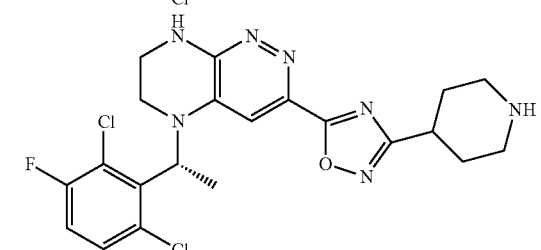
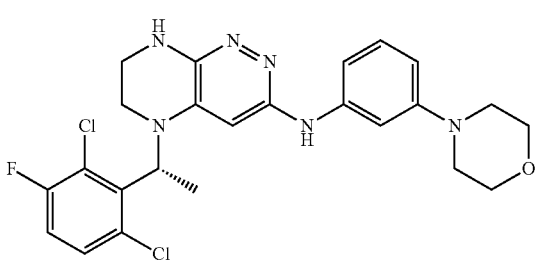 [SMILES: C[C@H](c1c(Cl)ccc(F)c1Cl)N1CCNc2nnc(Nc3cccc(N4CCOCC4)c3)cc21]
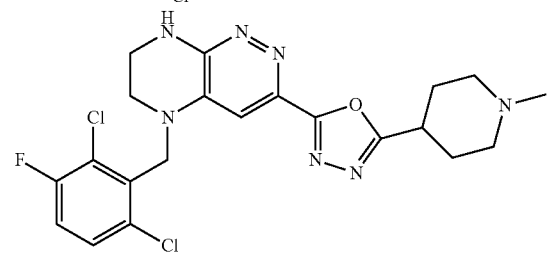
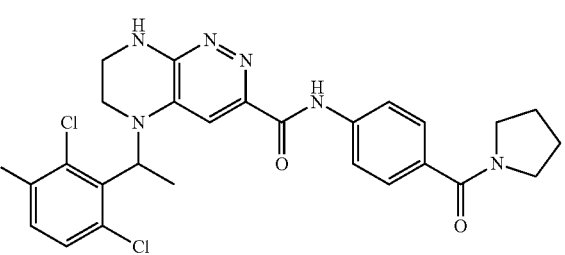

131
-continued

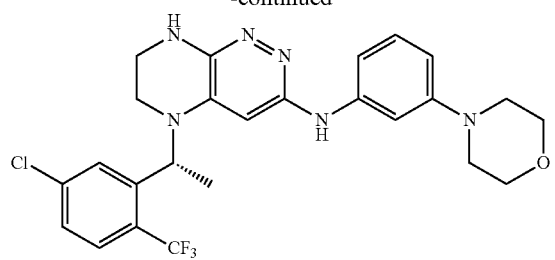

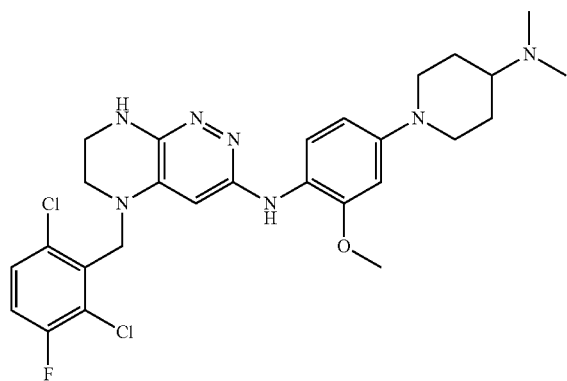

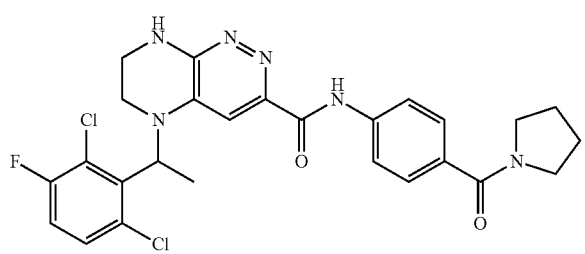

The list of compounds, inhibiting kinase MET with the value of $IC_{50}$ less than 10 μM

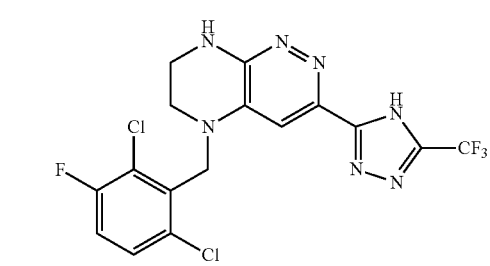

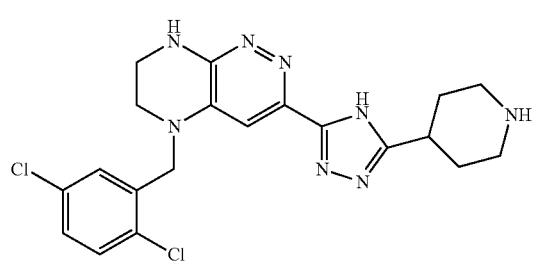

132
-continued

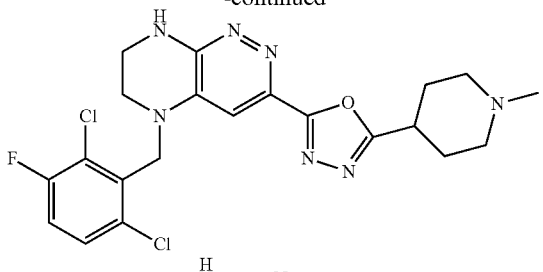

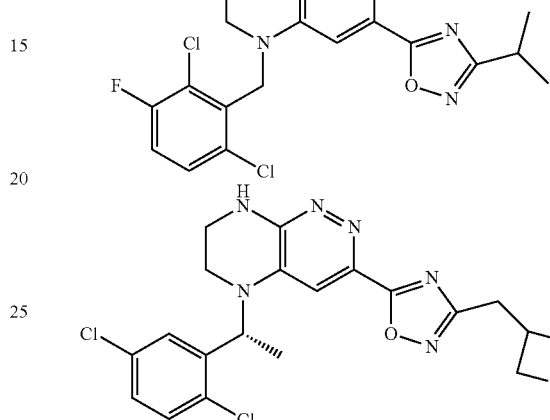

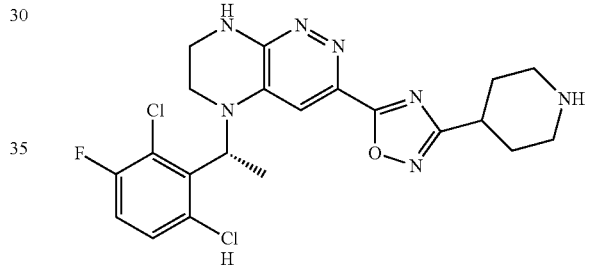

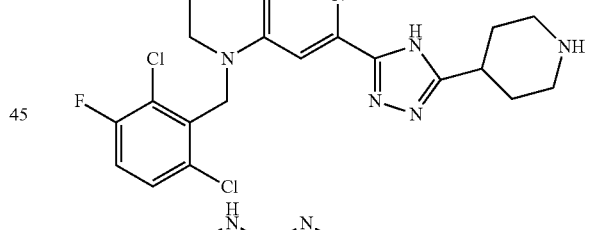

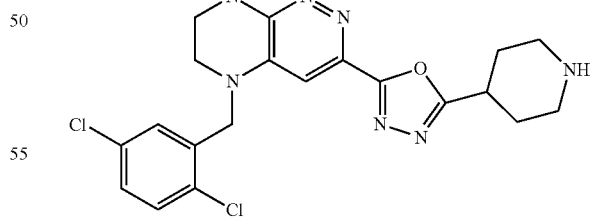

24.2. Experiments with Cell Cultures

Certain compounds of the present invention exhibit cytotoxicity or inhibit the growth of tumor and other cancer cell lines, and thus can be used for the treatment of cancer and other proliferative diseases.

Cellular methods for determining the antitumor activity are well known and can be used for comparing the characteristics of the compounds described herein. In general, the experiments on the proliferation of cells and the number of viable cells produce a detectable signal that is proportional to the number of metabolically active cells. Antitumor activity of compounds may be determined using any characteristic, reflecting a decrease in metabolic activity of cells after exposure to the compound. Conventionally, the methods in which membrane integrity (e.g., analysis of elimination of trypan blue) and DNA synthesis (e.g., determination of BrdU or $^3$H-thymidine incorporation) are used as a measure of cell viability.

Some methods for determining cell proliferation use reagents, which are converted to the compounds detected in the course of cell proliferation. Preferred reagents for such determination are tetrazolium salts, including, for example, MTT (3-(4,5-dimethylthiazole-2-yl)-2,5-diphenyltetrazolium bromide), MTS (3-(4,5-dimethylthiazole-2-yl)-5-(3-carboxymethoxyphenyl)-2-(4-sulfophenyl)-2H-tetrazolium), XTT (2,3-bis(2-methoxy-4-nitro-5-sulfophenyl)-2H-tetrazolium-5-carboxanilide), INT (2-(4-iodophenyl)-3-(4-nitrophenyl)-5-phenyl tetrazolium), NBT (2H-tetrazolium, 2,2'-(3,3'-dimethoxy[1,1'-biphenyl]-4,4'-diyl)bis[3-(4-nitrophenyl)-5-phenyl, dichloride) (Bernas, T. et. al., *Biochim Biophys Acta*, 1999, 1451, 73-81). The measurement of the amount of product of the enzymatic conversion of tetrazolium salts into blue formazan derivatives, which are easily detected spectroscopically, is carried out to determine cell proliferation.

In general, the preferred methods of determining cell proliferation include cells incubation in the medium selected for growth in the presence of test substance or without it. Growth conditions for various prokaryotic and eukaryotic cells are described in detail (Ausubel et al. Current Protocols in Molecular Biology. Wiley and Sons. 2003). A tetrazolium salt is added to cells to determine cell proliferation after incubation and then the number of formed formazan is determined. Number of formed formazan derivatives is determined by optical density of treated cells.

The cancer cell lines such as COLO 205, DLD-1, HCT-15, HT29 (colon cancer); HEP G2 (hepatoma); K-562 (leukemia); A549, NCI-H249, NCI-H2228, NCI-H3122 (lung cancer); Karpas-299, SU-DHL-1 (lymphoma); MCF7, MDA-MB-231 (breast cancer); SAOS-2 (osteosarcoma); OVCAR-3 (ovarian cancer); PANC-1 (pancreatic cancer); DU-145, PC-3 (prostate cancer); ACHN, CAKI-1 (renal cancer); MG-63 (sarcoma) may be used to determine the antiproliferative activity of the compounds.

Although mammalian cells are preferable used to determine the antiproliferative activity of the compounds, lower eukaryotic cells such as yeast, can also be used for this purpose. Preferably, the cell lines of human, rats, mice, rabbits, lower monkeys, hamsters and guinea pigs shall be used, as the cell lines of these organisms are the most well studied and fully characterized.

Below, there is an example of determining the activity of the compound on the cells. In this experiment, a cell line Ba/F3 (mice pro-B-cells) was used, stably transfected by vector pClneo™ (Promega Corp., Madison Wis.), encoding the chimeric protein NPM-ALK, and which passed the selection for resistance to G418. Interleukin IL-3 was required for control line cells survival, in which transfection was not performed. At the same time, Ba/F3 cells expressing NPM-ALK (Ba/F3-NPM-ALK), were viable in the absence of IL-3 because the kinase activity of NPM-ALK leaded to activation of signaling pathways responsible for cell proliferation. Expected inhibition of NPM-ALK kinase therefore blocks cell growth signals, which manifests itself in antiproliferative activity of the compounds. The antiproliferative activity, however, can be overcome by adding excess amounts of IL-3, inducing cellular growth under the mechanism independent of ALK. Example of similar experiments using FLT3 kinase is described in (Weisberg, E. et. al., *Cancer Cell*, 2002, 1, 433-43).

The inhibitory capacity of the compounds was determined as follows: cells Ba/F3-NPM-ALK were transferred in duplicate to a 96-well plate (15,000 per well). Analytes were dissolved in DMSO, then solution was diluted with DMSO and nutrient medium to the desired concentration, for the final concentration of DMSO did not exceed 1% by volume, and was transferred to the well with cells. The final concentration of compounds ranged from 0.5 nM to 10 µM. DMSO was used as a control in the same amount as in the addition of solution agents. After cells incubation with compounds for 3 days, the number of viable cells was determined. Thereto MTT solution was added to them, incubation was carried out and the optical density at 540 and 620 nm was determined (the number of viable cells was proportional to the ratio of optical densities at these wavelengths). $IC_{50}$ was determined from the curves, most adequately describing the experimental data, selected by the computer processing.

The used cell lines where the recombinant kinase activity is essential for survival, and inhibition of the kinase activity leads to cells death, which can be fixed by changing the concentration of ATP, can be used to determine the antiproliferative activity. The antiproliferative activity of the compounds is determined by the following procedure: cells expressing the receptor tyrosine kinase, e.g., ALK are cultured in a nutrient medium RPMI-1640, containing 10% of fetal calf serum and antibiotics. Reinoculation of cells is performed in the logarithmic growth phase. Cells are transferred in duplicate to 384-well culture plate (5,000 cells per well) in 50 µl of growth medium. 50 nl of solution of the test compound are added to each well and the cells are incubated for 48 hours at 37° C. in a humidified atmosphere containing 5% of CO2. The number of surviving cells is determined by adding 15 µl of reagent CellTiter-Glo and measuring luminescence. $IC_{50}$ is determined from the curves, most adequately describing the experimental data, selected by the computer processing.

Furthermore, antiproliferative activity of the compounds of this invention can be studied on cell lines KARPAS-299 of anaplastic large cell lymphoma according to the following procedure. KARPAS-299 cells cultured in RPMI 1640 growth medium, are transferred in duplicate to 96-well culture plate (10,000 cells per well) and a solution of the analytes in a growth medium is added to them at various concentrations (final volume in each well—100 µl). The solids were dissolved in DMSO and then the solution was diluted with DMSO to the desired concentration, mixed with an equal volume of growth medium and transferred to wells with the cells. The final concentration of compounds ranged from 0.5 nM to 10 µM. DMSO was used as a control (in the same amount as that of adding solutions of substances). After the cells incubation with the compounds for 72 hours, the number of viable cells was determined. For this purpose, old medium was removed, 100 µl of fresh medium and 40 µl of MTS solution, containing 5 mg/ml PBS were added to each well. The plate was incubated for 2 hours at 37° C., then 100 µl of DMSO was added to each well and mixed for 1 minute. Then, the optical density was determined at 490 nm and percentage of inhibition of proliferation was calculated in comparison with the control (containing no analytes).

Illustrative examples of compounds having antiproliferative activity, are as follows:

| Structure | Karpas-299 IC$_{50}$, nM [a] | Structure | Karpas-299 IC$_{50}$, nM |
|---|---|---|---|
| | <1000 | | <100 |
| | <100 | | <1000 |
| | <1000 | | <100 |
| | <100 | | <1000 |
| | <1000 | | <100 |
| | <100 | | <100 |

| Structure | Karpas-299 IC$_{50}$, nM [a] | Structure | Karpas-299 IC$_{50}$, nM |
|---|---|---|---|
| | <100 | | <100 |
| | <100 | | <100 |
| | <100 | | <100 |
| | <100 | | |

[a] concentration of compound at which the number of living cells in the experimental conditions is reduced 2-fold compared with the absence of compound.

24.3. Experiments with Animals

The compounds, which showed anti-proliferative activity in cell experiments, are then studied in vivo in mammalian organisms. Most experiments are conducted in vivo in rodents, such as mice and rats. Typically, a tumor is transplanted into a mouse with reduced immunity to reduce the likelihood of rejection. These mice are, for example, athymic nude mice and SCID-mice (mice with severe combined immunodeficiency).

Typically, the tumor is implanted subcutaneously, and the test animal is injected pharmaceutical preformulation in a certain dose and under certain regimen. The effectiveness of the test compound is determined by the tumor size reduction, which is measured at regular intervals. Some tumors are implanted in other points of the body (e.g., intraperitoneal), and the effectiveness criterion is the average time of survival of the organism. Typically, different tumor models, methods of administration and dosage regimens of pharmaceutical preformulations are compared in the course of the animal studies.

The Efficacy in Animal Model of Non-Small Cell Lung Cancer

The male athymic mice were used for the studies. NCI-H3122 cells in an amount of $1 \times 10^7$ were administered in the form of 0.2 ml Matrigel solution (BD Pharmingen) in the left leg of the mouse under ketamine-xylazine anesthesia. One week after cells injection mice were divided into the treatment and control groups and randomized by tumor size. Tumor volume was calculated according to the formula $V=0.5 \times W^2 \times L$. The control animals received daily 0.3 ml of 0.5% of methylcellulose solution, animals of the treatment group −0.3 ml of 0.5% of methylcellulose suspension containing the drug in a test dose. The solutions were administered by gavage. The treatment continued for 20 days. The ratio of the average volume for the treatment/control groups (% T/C) was calculated after treatment to determine the effectiveness of inhibition of tumor growth. The analysis of the statistical significance using Dunnett's test was performed for the data collection. Effectiveness of the test compounds in a dose of 30 mg/kg is introduced below.

| Substance | % T/C |
|---|---|
| 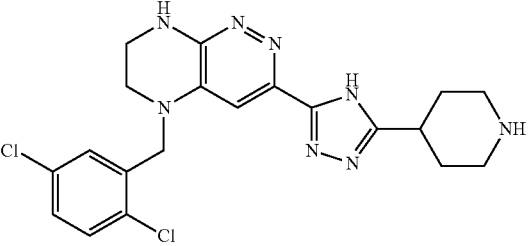 [SMILES: Clc1ccc(Cl)c(CN2CCNc3nnc(-c4nnc(C5CCNCC5)[nH]4)cc32)c1] | <40 |
| 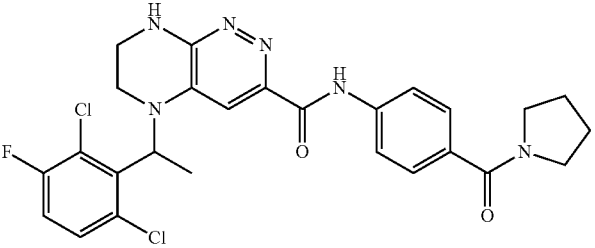 [SMILES: CC(c1c(Cl)ccc(F)c1Cl)N1CCNc2nnc(C(=O)Nc3ccc(C(=O)N4CCCC4)cc3)cc21] | <40 |
| 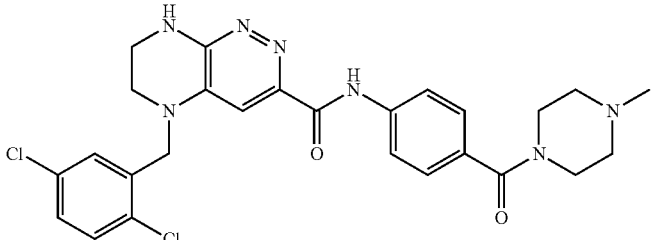 | <40 |
| 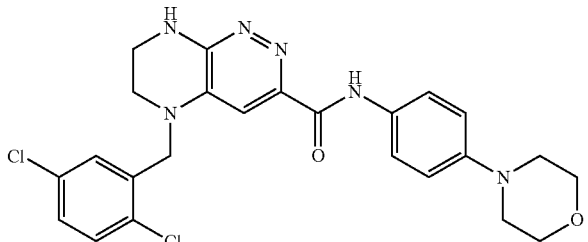 | <40 |
| 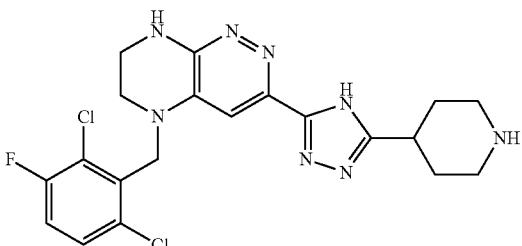 | <40 |
| 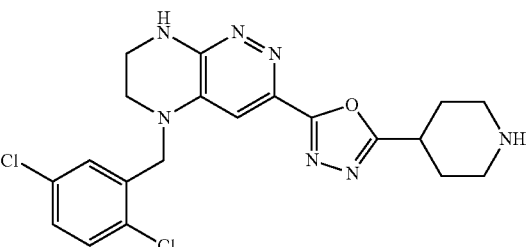 | <40 |

The Efficacy in Animal Model of Anaplastic Large Cell Lymphoma

SCID-mice with tumors that have developed as a result of the introduction of Karpas-299 cells were used for the studies. When tumor size reached 220 mm³ animals were divided into the treatment and control groups and were randomized by tumor size. The control animals received daily 0.3 ml of 0.5% of methylcellulose solution, animals of the treatment group—0.3 ml of 0.5% of methylcellulose suspension containing the drug in a test dose. The solutions were administered by gavage. The treatment continued for 23 days. The ratio of the average volume for the treatment/control groups (% T/C) was calculated after treatment to determine the effectiveness of inhibition of tumor growth. The analysis of the statistical significance using Dunnett's test was performed for the data collection. Effectiveness of the test compounds in a dose of 30 mg/kg is introduced below.

| Substance | % T/C |
|---|---|
| 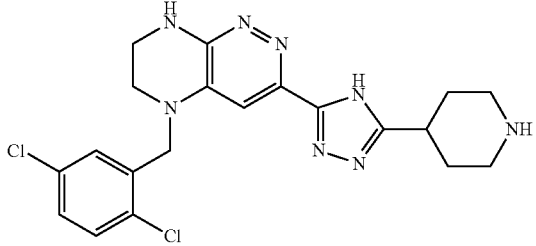 [SMILES: Clc1ccc(Cl)c(CN2CCNc3nnc(-c4nnc(C5CCNCC5)[nH]4)cc32)c1] | <40 |
| 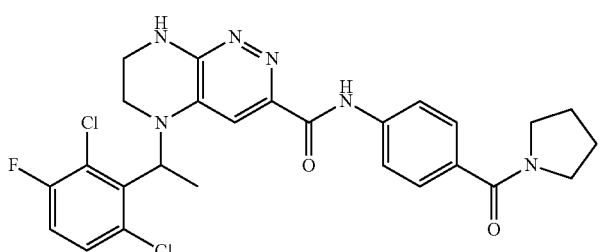 | <40 |
| 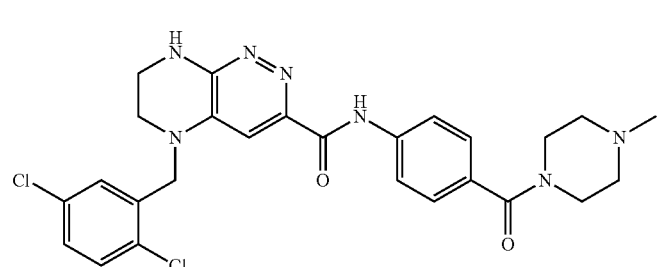 | <40 |
| 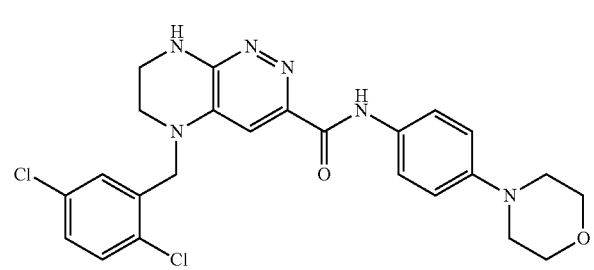 [SMILES: O=C(Nc1ccc(N2CCOCC2)cc1)c1cc2c(nn1)NCCN2Cc1cc(Cl)ccc1Cl] | <40 |
| 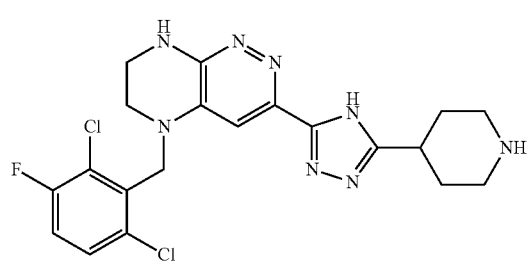 [SMILES: Fc1ccc(Cl)c(CN2CCNc3nnc(-c4nnc(C5CCNCC5)[nH]4)cc32)c1Cl] | <40 |

| Substance | % T/C |
|---|---|
| 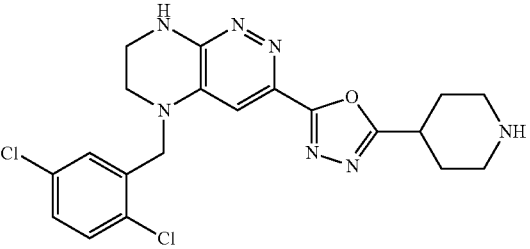 [SMILES: Clc1ccc(Cl)c(CN2CCNc3nnc(-c4nnc(C5CCNCC5)o4)cc32)c1] | <40 |

25. Examples of Pharmaceutical Formulation

The substances referred to in the present invention can be used for prevention and treatment of human diseases in the form of the following compositions (a "substance" means an active ingredient):

| Tablet I | mg/tablet |
|---|---|
| Substance | 100 |
| Lactose Ph. Eur | 182.75 |
| Croscarmellose sodium | 12.0 |
| Corn starch (5% w/v pasta) | 2.25 |
| Magnesium stearate | 3.0 |

| Tablet II | mg/tablet |
|---|---|
| Substance | 50 |
| Lactose Ph. Eur | 223.75 |
| Croscarmellose sodium | 6.0 |
| Corn starch | 15 |
| Polyvinylpyrrolidone (5% w/v pasta) | 2.25 |
| Magnesium stearate | 3.0 |

| Tablet III | mg/tablet |
|---|---|
| Substance | 1.0 |
| Lactose Ph. Eur | 93.25 |
| Croscarmellose sodium | 4.0 |
| Corn starch (5% w/v pasta) | 0.75 |
| Magnesium stearate | 1.0-76 |

| Capsule | mg/capsule |
|---|---|
| Substance | 10 |
| Lactose Ph. Eur | 488.5 |
| Magnesium | 1.5 |

| Composition for injections I | (50 mg/ml) |
|---|---|
| Substance | 5.0% w/v |
| 1M sodium hydroxide solution | 15.0% w/v |
| 1M chlorine hydride solution to pH 7.6 | |
| Polyethylene glycol 400 | 4.5% w/v |
| Injection water to 100% | |

| Composition for injections II | (10 mg/ml) |
|---|---|
| Substance | 1.0% w/v |
| Sodium phosphate BP | 3.6% w/v |
| M sodium hydroxide solution | 15.0% w/v |
| Injection water to 100% | |

| Composition for injections III | (1 mg/ml, buffer with pH 6) |
|---|---|
| Substance | 0.1% w/v |
| Sodium phosphate BP | 2.26% w/v |
| Citric acid | 0.38% w/v |
| Polyethylene glycol 400 | 3.5% w/v |

| Aerosol I | mg/ml |
|---|---|
| Substance | 10 |
| Sorbitan trioleate | 13.5 |
| Trichlorfluormethane | 910.0 |
| Dichloro-difluoro-methane | 490.0 |

| Ointment | ml |
|---|---|
| Substance | 40 mg |
| Ethanol | 300 μl |
| Water | 300 μl |
| 1-dodecylazacycloheptanone | 50 μl |
| Propylene glycol | up to 1 ml |

These compositions can be prepared according to conventional pharmaceutical techniques. Tablets (1)-(3) may be coated with enteric coating using, for example, cellulose acetate phthalate. The spray composition (8) may be used in conjunction with conventional dispensers; sorbitan monooleate, sorbitan poluoleat, polysorbate 80, polyglycerol oleate or oleic acid may be used as suspending agents instead of sorbitan trioleate.

The invention claimed is:

1. A compound of Formula I, a tautomer, isomer, enantiomer or pharmaceutically acceptable salt, solvate or hydrate thereof:

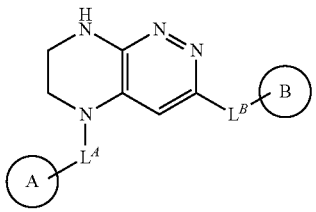

Formula I wherein:
$L^A$ is $CH_2$ or $CH(CH_3)$;
$L^B$ is a covalent chemical bond, $OC_{0-3}$-alkylene, $SC_{0-3}$-alkylene, $NHC(O)C_{0-3}$-alkylene, $C(O)NHC_{0-3}$-alkylene, $C(O)C_{0-3}$-alkylene, $NHC_{0-3}$-alkylene, $CH_2O$, $CH_2S$, $CH_2C(O)NH$ or $CH_2NH$;
cycle A is phenyl or a 5-6 membered heteroaryl containing 0-3 N atoms and 0-1 O or S atoms, and optionally substituted by 1-4 $R^A$ groups;
$R^A$ is independently selected from halogen, partially or fully halogenated $C_{1-5}$-alkyl, $C_{2-5}$alkenyl, $C_{2-5}$alkynyl, $(CH_2)_mO(CH_2)_nH$, $(CH_2)_mNH(CH_2)_nH$, $(CH_2)_mC(O)O(CH_2)_nH$, $(CH_2)_mOC(O)(CH_2)_nH$, $(CH_2)_mC(O)NH(CH_2)_nH$, $(CH_2)_mNHC(O)(CH_2)_nH$, CN, $P(O)(R^F)_2$, $P(O)_2(R^F)$, $P(O)_2OH$, $SR^E$, $S(O)R^E$, $S(O)_2R^E$ or $S(O)_2OH$;
cycle B is phenyl, $C_{3-8}$cycloalkyl, 4-8-membered saturated or partially saturated heterocycle containing 0-3 N atoms, and 0-1 O or S atoms; or a 5-6 membered heteroaryl ring containing 0-3 N atoms, and 0-1 O or S atoms; ring B is optionally substituted with 1-5 $R^B$ groups;
$R^B$ is independently selected from $L^C$-$R^C$, $L^C$-H, halogen, partially or completely halogenated $C_{1-5}$-alkyl, $C_{2-5}$-alkenyl, $C_{2-5}$-alkynyl or CN;
$L^C$ is a covalent chemical bond, $C_{1-3}$-alkyl, $(CH_2)_mO(CH_2)_n$, $(CH_2)_mNH(CH_2)_n$, $(CH_2)_mC(O)(CH_2)_n$, $(CH_2)_mC(O)O(CH_2)_n$, $(CH_2)_mOC(O)(CH_2)_n$, $(CH_2)_mC(O)NH(CH_2)_n$ or $(CH_2)_mNHC(O)(CH_2)_n$;
$R^C$ is independently selected from phenyl, $C_{1-6}$-alkyl, $C_{3-7}$ cycloalkyl or 3-7 membered heteroalicyclyl containing 0-3 N atoms, 0-2 O atoms and 0-2 S atoms; $R^C$ is optionally substituted by 1-5 $R^D$ or $CH_2R^D$ substituents;
$R^D$ is independently selected from halogen, $(CH_2)_mCH_3$, $(CH_2)_mO(CH_2)_nH$, $(CH_2)_mC(O)NH(CH_2)_nH$, $(CH_2)_mC(O)(CH_2)_nH$, $(CH_2)_mNH_2$, $NHR^F$, $N(R^F)_2$ or 3-7 membered heteroalicyclyl containing 0-3 N atoms, 0-2 O atoms, 0-2 S atoms, and optionally substituted by 1-3 $R^F$ substituents;
$R^E$ is independently selected from the group consisting of $C_{1-3}$-alkyl, $NHC_{1-3}$-alkyl or $N(C_{1-3}$-alkyl$)_2$;
$R^F$ is independently selected and represents $C_{1-3}$-alkyl;
m and n are selected independently from 0, 1, 2, 3.

2. The compound of claim 1 in which:
$L^A$ is $CH_2$ or $CH(CH_3)$;
$L^B$ is a covalent chemical bond, $OC_{0-3}$-alkylene, $SC_{0-3}$-alkylene, $NHC(O)C_{0-3}$-alkylene, $C(O)NHC_{0-3}$-alkylene, $C(O)C_{0-3}$-alkylene, $NHC_{0-3}$-alkylene, $CH_2O$, $CH_2S$, $CH_2C(O)NH$ or $CH_2NH$;
cycle A is phenyl, optionally substituted with by 1-3 $R^A$ groups;
$R^A$ is halogen, partially or fully halogenated $C_{1-3}$-alkyl, $OC_{1-3}$-alkyl, $S(O)C_{1-3}$-alkyl, $S(O)_2C_{1-3}$-alkyl, $S(O)NHC_{1-3}$-alkyl, $S(O)_2NHC_{1-3}$-alkyl, $S(O)N(C_{1-3}$-alkyl$)_2$, $S(O)_2N(C_{1-3}$-alkyl$)_2$ or $P(O)(C_{1-3}$-alkyl$)_2$;
cycle B is phenyl; $C_{3-7}$ cycloalkyl; 4-6-membered saturated or partially saturated heterocycle containing 0-3 N atoms, and 0-1 O or S atoms; or a 5-6 membered heteroaryl containing 0-3 N atoms, and 0-1 O or S atoms; ring B is optionally substituted with 1-5 $R^B$ substituents;
$R^B$ is independently selected from $L^C$-$R^C$, $L^C$-H, halogen or partially or completely halogenated $C_{1-3}$-alkyl;
$L^C$ is a covalent chemical bond, $C_{1-3}$-alkyl, $(CH_2)_mC(O)(CH_2)_n$, $(CH_2)_mC(O)NH(CH_2)_n$ or $(CH_2)_mO(CH_2)_n$;
$R^C$ is independently selected from phenyl, $C_{1-6}$-alkyl, or 4-6 membered heteroalicyclyl containing 0-2 N atoms, 0-1 O atom; $R^C$ is optionally substituted by 1-5 $R^D$ or $CH_2R^D$ substituents;
$R^D$ is independently selected from the group consisting of $(CH_2)_mCH_3$, $(CH_2)_mO(CH_2)_nH$, $(CH_2)_mC(O)NH(CH_2)_nH$, $(CH_2)_mC(O)(CH_2)_nH$, $(CH_2)_mNH_2$, $N(R^F)_2$ or 4-6 membered heteroalicyclyl containing 0-2 of N atoms, 0-1 of O atom; $R^D$ is optionally substituted by 1-3 $C_{1-3}$-alkyl substituents;
m and n are independently selected from 0, 1, 2, 3.

3. The compound of claim 1 in which:
$L^A$ is $CH_2$ or $CH(CH_3)$;
$L^B$ is a covalent chemical bond, $C(O)NH$ or NH;
cycle A is phenyl, optionally substituted with 1-3 $R^A$ groups;
$R^A$ is Cl, F, $CF_3$ or $OCH_3$;
cycle B is phenyl; 5-membered heteroaryl ring containing 1-3 of N atom; 5-membered heteroaryl ring containing 1-2 N atoms and 1 O atom or 6-membered heteroaryl ring containing 1-3 N atoms; ring B is optionally substituted with 1-3 $R^B$ substituents;
$R^B$ is independently selected from $L^C$-$R^C$ or $L^C$-H;
$L^C$ is a covalent chemical bond, $CH_2$, $C(O)$, $C(O)NH$, $CH_2C(O)NH$, $C(O)NHCH_2$, $C(O)NH(CH_2)_2$ or $OCH_2$;
$R^C$ is independently selected from phenyl, $C_{1-3}$-alkyl, 4-6 membered heteroalicyclyl containing 0-2 N atoms and 0-1 O atom; $R^C$ is optionally substituted by 1-3 $R^D$ or $CH_2R^D$ substituents;
$R^D$ is independently selected from $CH_3$, $OCH_3$, OH, $CH_2C(O)NH_2$, $C(O)CH_3$, $N(R^F)_2$ or 4-6 membered heteroalicyclyl containing 0-2 N atoms, 0-1 O atom; $R^D$ is optionally substituted by 1-3 $R^F$ substituents;
$R^F$ is $CH_3$.

4. The compound of claim 1 in which $L^B$ is a covalent chemical bond, NH or C(O)NH.

5. The compound of claim 1 in which ring A is phenyl.

6. A pharmaceutical composition for treatment and/or prevention of a disease associated with aberrant activity of protein kinases, comprising an effective amount of a compound according to claim 1 and a pharmaceutically acceptable carrier, diluent and/or excipient.

* * * * *